US012624100B2

(12) United States Patent
Bammert et al.

(10) Patent No.: US 12,624,100 B2
(45) Date of Patent: May 12, 2026

(54) HUMANIZED CLDN18.2 ANTIBODIES

(71) Applicant: SOTIO BIOTECH A.S., Prague (CZ)

(72) Inventors: Lukas Bammert, Basel (CH); Lenka Kyrych Sadilkova, Horomerice (CZ); Lorenz Waldmeier, Basel (CH); Roger Beerli, Adlikon bei Regensdorf (CH); Ulrich Moebius, Gauting (DE)

(73) Assignee: SOTIO BIOTECH A.S., Prague (CZ)

( * ) Notice: Subject to any disclaimer, the term of this patent is extended or adjusted under 35 U.S.C. 154(b) by 998 days.

(21) Appl. No.: 17/782,417

(22) PCT Filed: Dec. 7, 2020

(86) PCT No.: PCT/EP2020/084831
§ 371 (c)(1),
(2) Date: Jun. 3, 2022

(87) PCT Pub. No.: WO2021/111003
PCT Pub. Date: Jun. 10, 2021

(65) Prior Publication Data
US 2023/0030674 A1     Feb. 2, 2023

(30) Foreign Application Priority Data

Dec. 6, 2019   (EP) .................................... 19214104

(51) Int. Cl.
*C07K 16/28*        (2006.01)

(52) U.S. Cl.
CPC .......... *C07K 16/28* (2013.01); *C07K 2317/24* (2013.01); *C07K 2317/41* (2013.01); *C07K 2317/55* (2013.01); *C07K 2317/56* (2013.01); *C07K 2317/565* (2013.01); *C07K 2317/622* (2013.01); *C07K 2317/72* (2013.01); *C07K 2317/73* (2013.01); *C07K 2317/732* (2013.01); *C07K 2317/734* (2013.01); *C07K 2317/92* (2013.01); *C07K 2317/94* (2013.01); *C07K 2319/40* (2013.01)

(58) Field of Classification Search
CPC ............................ C07K 16/28; C07K 16/3076
USPC ....................................................... 424/130.1
See application file for complete search history.

(56) References Cited

U.S. PATENT DOCUMENTS

| | | | | |
|---|---|---|---|---|
| 9,334,331 | B2 * | 5/2016 | Igawa ........................ | A61P 7/00 |
| 10,421,807 | B2 * | 9/2019 | Gonzales ................ | A61P 43/00 |
| 10,421,817 | B1 | 9/2019 | Hu et al. | |
| 2024/0034783 | A1 * | 2/2024 | Bammert ................ | A61P 35/00 |
| 2024/0100180 | A1 * | 3/2024 | Bammert ........... | A61K 47/6849 |
| 2024/0294594 | A1 * | 9/2024 | Adkins ................... | A61P 35/02 |
| 2024/0350589 | A1 * | 10/2024 | Kyrych Sadilkova ....................... | |
| | | | | A61K 47/68033 |

FOREIGN PATENT DOCUMENTS

| | | |
|---|---|---|
| CN | 109762067 A | 5/2019 |
| WO | 00/15659 A2 | 3/2000 |
| WO | 2004/047863 A2 | 7/2004 |
| WO | 2005/113587 A2 | 12/2005 |
| WO | 2007059997 A1 | 5/2007 |
| WO | 2008145338 A1 | 12/2008 |
| WO | 2013/167259 A1 | 11/2013 |
| WO | 2013/174509 A1 | 11/2013 |
| WO | 2014/075788 A1 | 5/2014 |
| WO | 2014/127906 A1 | 8/2014 |
| WO | 2014146672 A1 | 9/2014 |
| WO | 2016/165762 A1 | 10/2016 |
| WO | 2016/166122 A1 | 10/2016 |
| WO | 2018/006882 A1 | 1/2018 |
| WO | 2019/174617 A1 | 9/2019 |
| WO | 2019/175617 A1 | 9/2019 |
| WO | 2019173420 A1 | 9/2019 |
| WO | 2019/219089 A1 | 11/2019 |
| WO | 2022122709 A1 * | 6/2022 |
| WO | 2025078686 A1 * | 4/2025 |

OTHER PUBLICATIONS

George et al. (Circulation. 1998; 97: 900-906).*
Edwards et al. (2003, JMB 334:103-118).*
Lloyd et al. (2009, Protein Engineering, Eng. Design & Selection 22(3): 159-168).*
Goel et al. (2004, J. Immunol. 173: 7358-7367).*
Khan et al. (2014, J. Immunol. 192: 5398-5405).*
Poosarla et al. (2017, Biotechn. Bioeng. 114(6): 1331-1342).*
Trademark Status & Document Retrieval (TSDR)—nanobody (pp. 1-2; Dec. 12, 2025)).*
Alegre et al., "Effect of a single amino acid mutation on the activating and immunosuppressive properties of a "humanized" OKT3 monoclonal antibody," Journal of Immunology, vol. 148, No. 11, Jun. 1992, pp. 3461-3468. (Abstract Only).
An et al., "IgG2m4, an engineered antibody isotype with reduced Fc function,", mAbs, vol. 1, No. 6, Nov.-Dec. 2009, pp. 572-579.
Bolt et al., "The generation of a humanized, non-mitogenic CD3 monoclonal antibody with retains in vitro immunosuppressive properties," European Journal of Immunology, vol. 23, No. 2, Feb. 1993, pp. 403-411. (Abstract Only).
Chang et al., "CARs: Synthetic Immunoreceptors for Cancer Therapy and Beyond," Trends in Molecular Medicine, vol. 23, No. 5, Apr. 2017, pp. 430-450.
Chu et al., "Inhibition of B cell receptor-mediated activation of primary human B cells by coengagement of CD19 and FcgammaRIIb with Fc-engineered antibodies," Molecular Immunology, vol. 45, No. 15, Aug. 2008, pp. 3926-3933. (Abstract Only).
Dall'Acqua et al., "Increasing the Affinity of a Human IgG1 for the Neonatal Fc Receptor: Biological Consequences," The Journal of Immunology, vol. 169, No. 9, Nov. 2002, pp. 5171-5180.
(Continued)

*Primary Examiner* — Lynn A Bristol
(74) *Attorney, Agent, or Firm* — Kagan Binder, PLLC

(57) ABSTRACT

The invention provides humanized antibodies binding to CLDN18.2 with a high affinity. Further, the antibodies do not exhibit cross-reactivity to CLDN18.1. The invention also provides nucleic acids, vectors, host cells and medical uses.

17 Claims, 21 Drawing Sheets
Specification includes a Sequence Listing.

(56) References Cited

OTHER PUBLICATIONS

Diebolder et al., "Complement Is Activated by IgG Hexamers Assembled at the Cell Surface," Science, vol. 343, No. 6176, Mar. 2014, pp. 1260-1263.

Ellerman, D., "Bispecific T-cell engagers: Towards understanding variables influencing the in vitro potency and tumor selectivity and their modulation to enhance their efficacy and safety," Methods, vol. 154, Nov. 2018, pp. 102-117.

Hashimoto et al., "Engineered membrane protein antigens successfully induce antibodies against extracellular regions of claudin-5," Scientific Reports, vol. 8, No. 8383, May 2018, pp. 12.

Hewitt et al., "The claudin gene family: expression in normal and neoplastic tissues," BMC Cancer, vol. 6, No. 186, Jul. 2006, pp. 8.

Idusogie et al., "Engineered antibodies with increased activity to recruit complement," The Journal of Immunology, vol. 166, No. 4, Feb. 2001, pp. 2571-2575.

Jiang et al., "Claudin 18.2-Specific Chimeric Antigen Receptor Engineered T Cells for the Treatment of Gastric Cancer," Journal of the National Cancer Institute, vol. 111, No. 4, Sep. 2018, pp. 409-418.

June et al., "Chimeric Antigen Receptor Therapy," The New England Journal of Medicine, vol. 379, No. 1, Jul. 2018, pp. 64-73.

Lazar et al., "Engineered antibody Fc variants with enhanced effector function," Proceedings of the National Academy of Sciences of the United States of America, vol. 103, No. 11, Mar. 2006, pp. 4005-4010.

Leabman et al., "Effects of altered FcgammaR binding on antibody pharmacokinetics in cynomolgus monkeys," Mabs, vol. 5, No. 6, Sep. 2013, pp. 896-903.

Lo et al., "Effector-attenuating Substitutions That Maintain Antibody Stability and Reduce Toxicity in Mice," Journal of Biological Chemistry, vol. 292, No. 9, Mar. 2017, pp. 3900-3908.

Mimoto et al., "Novel asymmetrically engineered antibody Fc variant with superior FcgammaR binding affinity and specificity compared with afucosylated Fc variant," mAbs, vol. 5, No. 2, Feb. 2013, pp. 229-236.

Moore et al., "Engineered Fc variant antibodies with enhanced ability to recruit complement and mediate effector functions,", mAbs, vol. 2, No. 2, Mar. 2010, pp. 181-189.

Natsume et al., "Engineered Antibodies of IgG1/IgG3 Mixed Isotype with Enhanced Cytotoxic Activities," Cancer Research, vol. 68, No. 10, May 2008, pp. 3863-3872.

Niimi et al., "claudin-18, a Novel Downstream Target Gene for the T/EBP/NKX2.1 Homeodomain Transcription Factor, Encodes Lung- and Stomach-Specific Isoforms through Alternative Splicing," Molecular and Cellular Biology, vol. 21, No. 21, Nov. 2001, pp. 7380-7390.

Richards et al., "Optimization of antibody binding to FcgammaRIIa enhances macrophage phagocytosis of tumor cells," Molecular Cancer Therapeutics, vol. 7, No. 8, Aug. 2008, pp. 2517-2527.

Rother et al., "Discovery and development of the complement inhibitor eculizumab for the treatment of paroxysmal nocturnal hemoglobinuria,", Nature Biotechnology, vol. 25, No. 11, Nov. 2007, pp. 1256-1264 and Erratum of vol. 25, No. 12, Dec. 2007, pp. 1.

Shang et al., "Selective Antibody Intervention of Toll-like Receptor 4 Activation through Fc gamma Receptor Tethering," The Journal of Biological Chemistry, vol. 289, No. 22, Apr. 2014, pp. 15309-15318.

Shields et al., "High Resolution Mapping of the Binding Site on Human IgG1 for Fc gamma RI, Fc gamma RII, Fc gamma RIII, and FcRn and Design of IgG1 Variants with Improved Binding to the Fc gamma R," Journal of Biology Chemistry, vol. 276., No. 9, Mar. 2001, pp. 6591-6604.

Stavenhagen et al., "Fc Optimization of Therapeutic Antibodies Enhances Their Ability to Kill Tumor Cells In vitro and Controls Tumor Expansion In vivo via Low-Affinity Activating Fcgamma Receptors," Cancer Research, vol. 67, No. 18, Sep. 2007, pp. 8882-8890.

Tao et al., "Studies of aglycosylated chimeric mouse-human IgG. Role of carbohydrate in the structure and effector functions mediated by the human IgG constant region," The Journal of Immunology, vol. 143, No. 8, Oct. 1989, pp. 2595-2601. (Abstract Only).

Vafa et al., "An engineered Fc variant of an IgG eliminates all immune effector functions via structural perturbations," Methods, vol. 65, No. 1, Jul. 2013, pp. 114-126.

Waldmeier et al., "Transpo-mAb display: Transposition-mediated B cell display and functional screening of full-length IgG antibody libraries," mAbs, vol. 8, No. 4, Apr. 2016, pp. 726-740.

Walker et al., "Aglycosylation of human IgG1 and IgG3 monoclonal antibodies can eliminate recognition by human cells expressing Fc gamma RI and/or Fc gamma RII receptors," Biochemical Journal, vol. 259, No. 2, Apr. 1989, pp. 347-353.

Wang et al., "IgG Fc engineering to modulate antibody effector functions," Protein & Cell, vol. 9, No. 1, Oct. 2017, pp. 63-73.

Xu et al., "In vitro Characterization of Five Humanized OKT3 Effector Function Variant Antibodies,", Cell Immunology, vol. 200, No. 1, Feb. 2000, pp. 16-26. (Abstract Only).

Yu et al., "Stimulus-induced reorganization of tight junction structure: the role of membrane traffic," Biochimica et Biophysica Acta (BBA), vol. 1778, No. 3, Aug. 2007, pp. 709-716.

Zalevsky et al., "Enhanced antibody half-life improves in vivo activity," Nature Biotechnology, vol. 28, No. 2, Jan. 2010, pp. 157-159.

International Search Report and Written Opinion for International Application No. PCT/EP2020/084831, mailed Mar. 3, 2021 (17 pages).

Extended European Search Report for European Application No. 19214104.2, mailed Feb. 28, 2020 (10 pages).

Sahin et al., (2008) "Claudin-18 Splice Variant 2 Is a Pan-Cancer Target Suitable for Therapeutic Antibody Development", Clinical Cancer Research, 14(23):7624-7634.

* cited by examiner

A    IMAB362

B    hGBA-1

C        hGBA-2

D        hGBA-3

G    hGBA-6

H    hGBA-7

I    hGBA-8

J    hGBA-9

K    secondary only

L    pan-CLDN18

A

B

HUMANIZED CLDN18.2 ANTIBODIES

CROSS-REFERENCE TO RELATED APPLICATIONS

This application claims priority to International Application No. PCT/EP2020/084831, filed Dec. 7, 2020 and titled "HUMANIZED CLDN18.2 ANTIBODIES," which in turn claims priority from a European Patent Application having Ser. No. 19/214,104.2, filed Dec. 6, 2019, both applications of which are incorporated herein by reference in their entireties.

REFERENCE TO SEQUENCE LISTING

This application contains a Sequence Listing submitted via EFS-Web. The entire contents of the sequence listing in ASCII text file entitled "S12415_PCT_Sequence_Listing.txt" created on Dec. 3, 2020, and having a size of 110 kilobytes, is incorporated herein by reference.

BACKGROUND

Tight junctions are multiprotein complexes connecting adjacent epithelial or endothelial cells to form a barrier, preventing molecules from passing in between the cells, and helping to maintain the cell and tissue polarity. Tight junctions consist of three main groups of transmembrane proteins: claudins and occludin, cytoplasmic plaque proteins, and cingulin. They also contain cytoskeletal and signaling proteins, e.g. actin, myosin II, and PKCζ. These proteins interact to maintain tight junction structure (Yu and Turner 2008).

Claudins form a family of 23 proteins (Hewitt, Agarwal, and Morin 2006). Claudin 18 is human protein encoded by the CLDN18 gene, which forms tight junction strands in epithelial cells. The human CLDN18 can be alternatively spliced with two alternative first exons, resulting in two protein isoforms, CLDN18.1 (or Claudin 18.1) and CLDN18.2 (or Claudin 18.2). CLDN18.2 was first disclosed as Zsig28 protein in WO2000/015659. The two isoforms differ in the N-terminal 69 amino acids, encompassing the first extracellular loop. The first extracellular domain spans from amino acid 28 to amino acid 80. Within this stretch there are 8 amino acid differences between CLDN18.1 and CLDN18.2. The two different isoforms are expressed in different tissues, with CLDN18.1 being predominantly expressed in lung tissue whereas CLDN18.2 displays stomach specificity (Niimi et al. 2001). CLDN18.2 expression in normal stomach is restricted to the differentiated short-lived cells of stomach epithelium. CLDN18.2 expression has further been identified in various tumor tissues. For example, CLDN18.2 has been found to be expressed in pancreatic, esophageal, ovarian, and lung tumors, correlating with distinct histologic subtypes (Sahin et al. 2008).

In view of its restricted expression pattern in normal tissues, and its ectopic expression in human cancers, CLDN18.2 is an attractive pan-cancer target for antibody therapy of epithelial tumors. A number of studies have been made towards such an antibody therapy. WO2004/047863 identified the splice variants of CLDN18 and screened antibodies against different peptides derived from CLDN18.2: peptide DQWSTQDLYN (SEQ ID NO: 68), N-terminal extracellular of CLDN18.2, independent of glycosylation; peptide NNPVTAVFNYQ (SEQ ID NO: 69), N-terminal extracellular of CLDN18.2, mainly unglycosylated; and peptide STQDLYNNPVTAVF (SEQ ID NO: 70), N-terminal extracellular domain of CLDN18.2, unglycosylated. It also disclosed polyclonal rabbit antibodies screened with a pan-CLDN18 peptide TNFWMSTANMYTG (SEQ ID NO: 71) in the C-terminal extracellular domain common to both CLDN18.1 and CLDN18.2 isoforms. WO2005/113587 discloses antibodies against specific epitopes on CLDN18.2 defined by the following peptide sequences: ALMIVGIVLGAIGLLV (SEQ ID NO: 72) and RIGSMED-SAKANMTLTSGIMFIVS (SEQ ID NO: 73). WO200/7059997 discloses CLDN18.2 specific monoclonal antibodies obtained by immunization with the peptide METDTLLLWVLLLWVPGSTGDAAQPARRARRTKLG-TELGSTPVWWNSADGRMDQ WSTQD-LYNNPVTAVFNYQGLWRSCVRESSGFTECR-GYFTLLGLPAMLQAVRAAIQH SGGRSRRARTKTHLRRGSE (SEQ ID NO: 74), including the first extracellular domain of CLDN18.2 with N- and C-terminal extensions. Antibodies obtained by this immunization mediate cell killing by complement dependent cytotoxicity (CDC) and antibody-dependent cell-mediated cytotoxicity (ADCC). Antibody IMAB362, also known as Claudiximab or Zolbetuximab, is disclosed in WO2007/059997 and WO2016/165762. IMAB362 is an IgG1 antibody derived from a murine monoclonal antibody and has been chimerized to display the human IgG1 constant region for clinical use. WO2008/145338 also discloses antibodies binding to overlapping peptides within the first extracellular domain (MDQWSTQDLYNNPVT (SEQ ID NO: 75), LYNNPVTAVFNYQGL (SEQ ID NO: 76), VFNYQGLWRSCVRES (SEQ ID NO: 77), QGLWRSCVRESSGFT (SEQ ID NO: 78), and RSCVRESSGFTECRG (SEQ ID NO: 79)). In an effort to produce antibodies targeting the C-terminal portion of CLDN18.2 for diagnostic purposes to detect CLDN18.2 expression in cells of cancer tissue sections, WO2013/167259 discloses antibodies binding to C-terminal epitopes of CLDN18.2. The sequences of the two epitopes are TEDEVQSYPSKHDYV (SEQ ID NO: 80) and EVQSYPSKHDYV (SEQ ID NO: 81). WO2013/174509 presents combinations of anti-CLDN18.2 antibodies with agents stabilizing γδ T cells or with agents stabilizing or increasing the expression of CLDN18.2. Antibodies may be conjugated to a therapeutic moiety such as a cytotoxin, a drug (e.g. an immunosuppressant) or a radioisotope. WO2014075788 discloses a method of treatment a cancer disease using a bispecific antibody binding CLDN18.2 and CD3. WO2014/127906 discloses combination agents stabilizing or increasing the expression of CLDN18.2. WO2016/166122 discloses anti-CLDN18.2 monoclonal antibodies that can be highly efficiently internalized upon CLDN18.2 binding and therefore, are suitable for antibody-drug conjugate (ADC) development. Furthermore, the conjugation of such antibodies to the drugs DM4 and MMAE using cleavable SPDB or Valine-Citrulline linkers, respectively, is disclosed. However, despite all the antibodies disclosed in the patent applications, only the chimeric IMAB362, disclosed in WO2007/059997 and WO2016/165762, is currently tested in clinical trial. In addition to these antibodies and ADCs, WO2018/006882 discloses chimeric antigen receptor (CAR) based on anti-CLDN18.2 monoclonal antibodies. Antibodies of WO2018/006882 have been humanized and their sequence is disclosed in in the Supplementary Materials section associated with Jiang et al. (2018). CAR T-cells based on the humanized antibody are currently tested in a phase I clinical trial (ClinicalTrials.gov Identifier: NCT03159819) in patients with advanced gastric adenocarcinoma and pancreatic adenocarcinoma. CN109762067 discloses other anti-CLDN18.2 monoclonal antibodies mediating cell killing by CDC and ADCC. WO2019/173420 discloses anti-CLDN18.2 humanized monoclonal antibodies with ADCC activity. WO2019/175617 discloses anti-CLDN18.2 monoclonal antibodies binding to a different epitope than IMAB362. WO2019/219089 discloses monoclonal antibodies binding to a mutant of CLDN18.2.

Chimeric antibodies, having mouse variable regions grafted on human constant domains, are often still immunogenic and this may result in enhanced clearance of the antibody and other safety implications (Sauerborn 2014). Therefore, further modification of the antibody sequence is required to reduce patient immune response and improve its therapeutic activity. Humanization is a process by which xenogeneic antibody sequences are modified to reduce this immunogenicity (Saldanha 2014). However, humanization of an antibody often also leads to loss of affinity. IMAB362, currently the clinically most advanced anti-CLDN18.2 antibody, is a chimeric antibody. Therefore, there is still a need for better anti-CLDN18.2 antibodies. The instant invention is directed to addressing these and other needs, by disclosing humanized IMAB362 antibodies with, surprisingly, higher affinity to CLDN18.2 than IMAB362.

DESCRIPTION OF THE INVENTION

Definitions

"Antibodies" or "antibody", also called "immunoglobulins" (Ig), generally comprise four polypeptide chains, two heavy (H) chains and two light (L) chains, and are therefore multimeric proteins, or comprise an equivalent Ig homologue thereof (e.g., a camelid antibody comprising only a heavy chain, single-domain antibodies (sdAb) or Nanobody® small-antigen binding fragments which can either be derived from a heavy or a light chain). The term "antibodies" includes antibody-based binding proteins, modified antibody formats retaining its target binding capacity. The term "antibodies" also includes full length functional mutants, variants, or derivatives thereof (including, but not limited to, murine, chimeric, humanized and fully human antibodies) which retain the essential epitope binding features of an Ig molecule, and includes dual specific, bispecific, multispecific, and dual variable domain Igs. Ig molecules can be of any class (e.g., IgG, IgE, IgM, IgD, IgA, and IgY), or subclass (e.g., IgG1, IgG2, IgG3, IgG4, IgA1, and IgA2) and allotype. Ig molecules may also be mutated e.g. to enhance or reduce affinity for Fcy receptors or the neonatal Fc receptor (FcRn).

An "antibody fragment", as used herein, relates to a molecule comprising at least one polypeptide chain derived from an antibody that is not full length and exhibits target binding, including, but not limited to (i) a Fab fragment, which is a monovalent fragment consisting of the variable light (VL), variable heavy (VH), constant light (CL) and constant heavy 1 (CH1) domains; (ii) a F(ab')₂ fragment, which is a bivalent fragment comprising two Fab fragments linked by a disulfide bridge at the hinge region (reduction of a F(ab')₂ fragment result in two Fab' fragment with a free sulfhydryl group); (iii) a heavy chain portion of a Fab (Fa) fragment, which consists of the VH and CH1 domains; (iv) a variable fragment (Fv) fragment, which consists of the VL and VH domains of a single arm of an antibody; (v) a domain antibody (dAb) fragment, which comprises a single variable domain; (vi) an isolated complementarity determining region (CDR); (vii) a single chain Fv fragment (scFv); (viii) a diabody, which is a bivalent, bispecific antibody in which VH and VL domains are expressed on a single polypeptide chain, but using a linker that is too short to allow for pairing between the two domains on the same chain, thereby forcing the domains to pair with the complementarity domains of another chain and creating two antigen binding sites; (ix) a linear antibody, which comprises a pair of tandem Fv segments (VH-CH1-VH-CH1) which, together with complementarity light chain polypeptides, form a pair of antigen binding regions; (x) Dual-Variable Domain Immunoglobulin (xi) other non-full length portions of immunoglobulin heavy and/or light chains, or mutants, variants, or derivatives thereof, alone or in any combination.

An "antibody-based binding protein", as used herein, may represent any protein that contains at least one antibody-derived VH, VL, or CH immunoglobulin domain in the context of other non-immunoglobulin, or non-antibody derived components. Such antibody-based proteins include, but are not limited to (i) Fc-fusion proteins of binding proteins, including receptors or receptor components with all or parts of the immunoglobulin CH domains, (ii) binding proteins, in which VH and or VL domains are coupled to alternative molecular scaffolds, or (iii) molecules, in which immunoglobulin VH, and/or VL, and/or CH domains are combined and/or assembled in a fashion not normally found in naturally occurring antibodies or antibody fragments.

The term "modified antibody format", as used herein, encompasses polyalkylene oxide-modified scFv, monobodies, diabodies, camelid antibodies, domain antibodies, bi- or trispecific antibodies, IgA, or two IgG structures joined by a J chain and a secretory component, shark antibodies, new world primate framework and non-new world primate CDR, IgG4 antibodies with hinge region removed, IgG with two additional binding sites engineered into the CH3 domains, antibodies with altered Fc region to enhance or reduce affinity for Fc gamma receptors, dimerized constructs comprising CH3, VL, and VH, and the like.

The Kabat numbering scheme (Martin and Allemn 2014) has been applied to the disclosed antibodies.

The term "selectively binds to CLDN18.2" or "selective binding to CLDN18.2" as referred to herein refers to an antibody exhibiting binding to CLDN18.2, while exhibiting no (specific) binding to CLDN18.1. Hence, the antibodies selectively binding to CLDN18.2 do not exhibit cross-reactivity to CLDN18.1.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

Where an indefinite or definite article is used when referring to a singular noun, e.g. "a", "an" or "the", this includes a plural of that noun unless something else is specifically stated.

Technical terms are used by their common sense. If a specific meaning is conveyed to certain terms, definitions of terms will be given in the following in the context of which the terms are used.

Description

The inventors have surprisingly identified novel anti-CLDN18.2 antibodies as further described in the following embodiments. These antibodies bind to CLDN18.2 with a higher affinity than the IMAB362 antibody.

Therefore, in one embodiment, the invention provides an antibody or fragment thereof binding to CLDN18.2, which comprises the heavy chain complementarity determining regions (HCDR) HCDR1, HCDR2 and HCR3 consensus sequences of SEQ ID NO: 1, SEQ ID NO: 2 and SEQ ID NO: 3, respectively and the light chain complementary regions (LCDR) LCDR1, LCDR2 and LCDR3 consensus sequences of SEQ ID NO: 4, SEQ ID NO: 5 and SEQ ID NO: 6, respectively. The respective consensus sequences can be found in Table 1. It is understood that any antibody or fragment thereof based on any combination of CDRs derived from the consensus sequences and binding to CLDN18.2 is part of the invention.

In a preferred embodiment, the isolated antibody or functional fragment thereof binds to CLDN18.2 but not to CLDN18.1. Hence, the provided antibodies specifically bind CLDN18.2.

TABLE 1 isolated antibody CDR consensus sequences

| CDR | Sequences | SEQ ID |
|---|---|---|
| HCDR1 | GYXFTSYWIG<br>X in 3rd position is T or S | SEQ ID NO: 1 |
| HCDR2 | GXIYPXXXXTXYX<br>X in 2nd position is N or I;<br>X in 6th position is S or G;<br>X in 7th position is A, E or D;<br>X in 8th position is A or S;<br>X in 9th position is Y or D;<br>X in 11th position is N or R;<br>X in last position is A or S | SEQ ID NO: 2 |
| HCDR3 | XRXWRGNSFDX<br>X in 1st position is A or T;<br>X in 3rd position is L, M, I or Q;<br>X in last position is A or Y | SEQ ID NO: 3 |
| LCDR1 | KSSQSXLNSGNQKNYLX<br>X in 6th position is L or V;<br>X in last position is T or A | SEQ ID NO: 4 |
| LCDR2 | WASTRES | SEQ ID NO: 5 |
| LCDR3 | QXDYSYPXT<br>X in 2nd position is N or Q;<br>X in 8th position is L or F | SEQ ID NO: 6 |

Antibody binding or binding affinity is generally expressed n terms of equilibrium association or dissociation constants ($K_a$ or $K_d$, respectively), which are in turn reciprocal ratios of dissociation and association rate constants ($k_{off}$ and $k_{on}$, respectively). Thus, equivalent affinities may correspond to different rate constants, so long as the ratio of the rate constants remains the same. Binding affinities and/or rate constants can be determined using techniques well known in the art or described herein, such as ELISA, flow cytometry (FC) titration, isothermal titration calorimetry (ITC), Biacore™ (SPR), biolayer inferometry or fluorescent polarization. In some cases, due to the nature of the antigen, the $K_a$ or $K_d$ of antibodies may be difficult to measure. This is especially true for integral membrane proteins such as Claudins (Hashimoto et al. 2018). In such cases, the integral membrane protein may be expressed as proteoliposomes or lipoparticles. Such lipoparticles may be immobilized on plastic and used in ELISA assay to determine the binding affinity of antibodies to the immobilized antigen. Instead of $K_a$ or $K_d$ values, half maximal effective concentration (EC50) values may thus be calculated for each tested antibody or functional fragment thereof, reflecting its binding affinity to the antigen. Example 3 below and FIG. 2 exemplify ELISA assay binding affinity curves of antibodies with CDRs comprised in the consensus sequences of Table 1. Therefore, binding can be determined as in Example 4, where binding is quantified using ECSO values (Table 4 in Example 4) and the upper curve values (FIG. 4). The ECSO values and upper curves values (maxMFI) show surprisingly that the humanized antibodies of the present invention have a higher binding affinity. i.e. they exhibit increased binding to CLDN18.2 than the IMAB362 antibody. Maximum mean fluorescent intensity (maxMFI) can also be used to quantify the binding of antibodies. When comparing two antibodies binding to the same target, a higher maxMFI is indicative of a higher affinity and/or of a lower off rate. MaxMFI can be determined as shown in Example 4 and maxMFI values for the antibodies of the invention are shown in Table 4, when binding is measured by FC on HEK293T cells expressing CLDN18.2 or PA-TU-8988S-High cells.

Accordingly, preferably the antibodies of the invention or fragments thereof, bind with a higher affinity to CLDN18.2 than the IMAB362 antibody. In turn, FIG. 1D shows that all tested antibodies do not bind to HEK293T cells expressing CLDN18.1, and accordingly, all tested antibodies selectively bind to CLDN18.2. Further, in a preferred embodiment, such antibodies or fragments thereof are humanized.

In another embodiment, the invention provides an antibody or fragment thereof that binds to CLDN18.2, comprising:

a. the HCDR1, HCDR2 and HCDR3 sequences of SEQ ID NO: 7, SEQ ID NO: 9 and SEQ ID NO: 18, respectively and
the LCDR1, LCDR2 and LCDR3 sequences of SEQ ID NO: 25, SEQ ID NO: 5 and SEQ ID NO: 29, respectively;

b. the HCDR1, HCDR2 and HCDR3 sequences of SEQ ID NO: 7, SEQ ID NO: 10 and SEQ ID NO: 19, respectively and
the LCDR1, LCDR2 and LCDR3 sequences of SEQ ID NO: 25, SEQ ID NO: 5 and SEQ ID NO: 29, respectively;

c. the HCDR1, HCDR2 and HCDR3 sequences of SEQ ID NO: 7, SEQ ID NO: 10 and SEQ ID NO: 20, respectively and
the LCDR1, LCDR2 and LCDR3 sequences of SEQ ID NO: 25, SEQ ID NO: 5 and SEQ ID NO: 30, respectively;

d. the HCDR1, HCDR2 and HCDR3 sequences of SEQ ID NO: 7, SEQ ID NO: 12 and SEQ ID NO: 21, respectively and
the LCDR1, LCDR2 and LCDR3 sequences of SEQ ID NO: 26, SEQ ID NO: 5 and SEQ ID NO: 30, respectively;

e. the HCDR1, HCDR2 and HCDR3 sequences of SEQ ID NO: 7, SEQ ID NO: 13 and SEQ ID NO: 18, respectively and
the LCDR1, LCDR2 and LCDR3 sequences of SEQ ID NO: 25, SEQ ID NO: 5 and SEQ ID NO: 31, respectively;

f. the HCDR1, HCDR2 and HCDR3 sequences of SEQ ID NO: 8, SEQ ID NO: 14 and SEQ ID NO: 22, respectively and
the LCDR1, LCDR2 and LCDR3 sequences of SEQ ID NO: 25, SEQ ID NO: 5 and SEQ ID NO: 29, respectively;

g. the HCDR1, HCDR2 and HCDR3 sequences of SEQ ID NO: 7, SEQ ID NO: 15 and SEQ ID NO: 23, respectively and the LCDR1, LCDR2 and LCDR3 sequences of SEQ ID NO: 27, SEQ ID NO: 5 and SEQ ID NO: 29, respectively;

h. the HCDR1, HCDR2 and HCDR3 sequences of SEQ ID NO: 7, SEQ ID NO: 16 and SEQ ID NO: 23, respectively and the LCDR1, LCDR2 and LCDR3 sequences of SEQ ID NO: 25, SEQ ID NO: 5 and SEQ ID NO: 29, respectively; or i. the HCDR1, HCDR2 and HCDR3 sequences of SEQ ID NO: 8, SEQ ID NO: 17 and SEQ ID NO: 24, respectively and the LCDR1, LCDR2 and LCDR3 sequences of SEQ ID NO: 28, SEQ ID NO: 5 and SEQ ID NO: 31 respectively.

In a preferred embodiment, the antibody is humanized. As described above, these novel humanized antibodies bind with higher affinity to CLDN18.2 than the IMAB362 antibody, as for example shown by EC50 and maxMFI values. Further, the provided antibodies selectively bind to CLDN18.2.

In yet another embodiment, the invention provides for an antibody or fragment thereof that binds CLDN18.2, comprising:

a. a VH sequence of SEQ ID NO: 32;
b. a VH sequence of SEQ ID NO: 34;
c. a VH sequence of SEQ ID NO: 35;
d. a VH sequence of SEQ ID NO: 37;
e. a VH sequence of SEQ ID NO: 39;
f. a VH sequence of SEQ ID NO: 41;
g. a VH sequence of SEQ ID NO: 42;
h. a VH sequence of SEQ ID NO: 44; or
i. a VH sequence of SEQ ID NO: 45;
and
j. a VL sequence of SEQ ID NO: 33;
k. a VL sequence of SEQ ID NO: 36;
l. a VL sequence of SEQ ID NO: 38;
m. a VL sequence of SEQ ID NO: 40;
n. a VL sequence of SEQ ID NO: 43; or
o. a VL sequence of SEQ ID NO: 46.

In a preferred embodiment, the antibody is humanized. As described above, these novel humanized antibodies bind with higher affinity to CLDN18.2 than the IMAB362 antibody, as for example shown by EC50 and maxMFI values. Further, the provided antibodies selectively bind to CLDN18.2. It is understood that any isolated antibody or fragment thereof based on any combination of VH and VL regions and binding to CLDN18.2 is part of the invention. In a preferred embodiment, the antibody or functional fragment thereof binds to CLDN18.2 but not to CLDN18.1.

In another embodiment, the invention relates to an antibody or fragment thereof that binds CLDN18.2, comprising:

a. a VH sequence of SEQ ID NO: 32 and a VL sequence of SEQ ID NO: 33;
b. a VH sequence of SEQ ID NO: 34 and a VL sequence of SEQ ID NO: 33;
c. a VH sequence of SEQ ID NO: 35 and a VL sequence of SEQ ID NO: 36
d. a VH sequence of SEQ ID NO: 37 and a VL sequence of SEQ ID NO: 38;
e. a VH sequence of SEQ ID NO: 39 and a VL sequence of SEQ ID NO: 40;
f. a VH sequence of SEQ ID NO: 41 and a VL sequence of SEQ ID NO: 33;
g. a VH sequence of SEQ ID NO: 42 and a VL sequence of SEQ ID NO: 43;

h. a VH sequence of SEQ ID NO: 44 and a VL sequence of SEQ ID NO: 33; or
i. a VH sequence of SEQ ID NO: 45 and a VL sequence of SEQ ID NO: 46.

In a preferred embodiment, the antibody is humanized. Again, as described above, these novel humanized antibodies bind with higher affinity to CLDN18.2 than the IMAB362 antibody, as for example shown by EC50 and maxMFI values. Further, the provided antibodies selectively bind to CLDN18.2.

In a further embodiment, the invention provides an antibody or fragment thereof binding to CLDN18.2, consisting of:

a. the heavy chain sequence of SEQ ID NO: 49 and light chain sequence of SEQ ID NO: 50;
b. the heavy chain sequence of SEQ ID NO: 51 and light chain sequence of SEQ ID NO: 50;
c. the heavy chain sequence of SEQ ID NO: 52 and light chain sequence of SEQ ID NO: 53;
d. the heavy chain sequence of SEQ ID NO: 54 and light chain sequence of SEQ ID NO: 55;
e. the heavy chain sequence of SEQ ID NO: 56 and light chain sequence of SEQ ID NO: 57;
f. the heavy chain sequence of SEQ ID NO: 58 and light chain sequence of SEQ ID NO: 50;
g. the heavy chain sequence of SEQ ID NO: 59 and light chain sequence of SEQ ID NO: 60;
h. the heavy chain sequence of SEQ ID NO: 61 and light chain sequence of SEQ ID NO: 50; or
i. the heavy chain sequence of SEQ ID NO: 62 and light chain sequence of SEQ ID NO: 63.

In a preferred embodiment, the antibody is humanized. Again, as described above, these novel humanized antibodies bind with higher affinity to CLDN18.2 than the IMAB362 antibody, as for example shown by EC50 and maxMFI values. Further, the provided antibodies selectively bind to CLDN18.2.

In another embodiment, the invention provides an antibody or fragment thereof binding to CLDN18.2, wherein the antibody or fragment thereof is humanized. Humanization of monoclonal antibodies has been well-established. The Handbook of Therapeutic Antibodies, Second Edition, gives ample information on humanization of monoclonal antibodies (Saldanha 2014), bioinformatics tools for analysis of such antibodies (Martin and Allemn 2014) or development and manufacture of therapeutic antibodies (Jacobi et al. 2014). When used as human therapeutics, humanized antibodies have a lower risk, compared to chimeric antibodies, of inducing anti-drug antibodies, which would limit the therapeutic benefit and increase the risk of side effects of the antibody of the invention especially after repeated administration.

In another embodiment, the invention provides an isolated antibody or functional fragment thereof binding to CLDN18.2.

In one embodiment, the antibody of the invention does not bind to CLDN18.1. Hence, it does not exhibit cross-reactivity.

In another embodiment, the invention provides an antibody or functional fragment thereof binding to CLDN18.2, consisting of the heavy chain sequence of SEQ ID NO: 58 and light chain sequence of SEQ ID NO: 50.

In yet another embodiment, the invention relates to an antibody having an amino acid sequence with at least 80% identity, at least 85% identity, at least 90% identity, at least 95% identity or at least 98% identity to the amino acid sequence of an antibody described herein. Preferably, the antibody binds with higher affinity to CLDN18.2 than the IMAB362 antibody, as for example shown by EC50 and maxMFI values and/or selectively binds to CLDN18.2. In one embodiment, the antibody is humanized.

In one embodiment, the invention provides an antibody or fragment thereof binding to CLDN18.2 that competes for binding with an antibody or fragment thereof as described herein. In a preferred embodiment, the antibody or fragment thereof competes for binding with an antibody consisting of the heavy chain sequence of SEQ ID NO: 58 and the light chain sequence of SEQ ID NO: 50. In one embodiment, the antibody is humanized. In a further preferred embodiment, the antibody exhibits a binding affinity that is identical or increased as compared to the binding affinity of IMAB362. In another preferred embodiment, the antibody exhibits a binding affinity that is identical or increased as compared to the binding affinity of an antibody consisting of the heavy chain sequence of SEQ ID NO: 58 and the light chain sequence of SEQ ID NO: 50. The binding affinity may be measured by any suitable means. For example, the binding of the antibody may be measured as EC50 value or maxMFI by flow cytometry titration on HEK295T cells or PA-TU-8988S-High cell expressing CLDN18.2.

In another embodiment, the Fc domain of the antibody (or antibody fragment when present) may comprise modifications or mutations, such as the modifications or mutations listed in Table 2 below. Such a modification or mutation may be introduced to modulate the effector activity of the Fc domain of the antibody. Modification of antibodies may also include peptide tags added to the C-terminal end of the antibody HC and/or LC chain. Such tags may be used e.g. for protein purification or protein conjugation.

In another embodiment, the invention provides an isolated humanized antibody or fragment thereof that binds CLDN18.2, the antibody being in the format selected from an IgA1, IgA2, IgD, IgE, IgG1, IgG2, IgG3, IgG4, synthetic IgG, IgM, F(ab)$_2$, Fv, scFv, IgGACH2, F(ab')$_2$, scFvCH3, Fab, VL, VH, scFv4, scFv3, scFv2, dsFv, Fv, scFv-Fc, (scFv)$_2$, a non-depleting IgG, a diabody, a bivalent antibody or Fc-engineered versions thereof.

In a preferred embodiment, the antibody is an IgG1 type of antibody. The Fc region of immunoglobulins interacts with multiple Fcγ receptors (FcγR) and complement proteins (e.g. C1q), and mediates immune effector functions, such as elimination of targeted cells via antibody-dependent cellular cytotoxicity (ADCC), antibody-dependent cellular phago-cytosis (ADCP) or complement-dependent cytotoxicity (CDC). For therapeutic approaches, it may be beneficial to enhance or silence Fc related effector functions. The type of immunoglobulin (IgA, IgD, IgE, IgG, IgM) may be selected according to the desired effector function of the antibody related to the Fc domain given their known activities. One may also employ a synthetic immunoglobulin, such as an immunoglobulin with the IgG2 amino acids 118 to 260 and the IgG4 amino acids 261 to 447 or an IgG2 variant with point mutations from IgG4 (e.g. H268Q/V309L/A30S/P331S). Such synthetic immunoglobulins reduce effector functions of the antibody. Fc-engineered immunoglobulins may also be employed to modulate antibody effector function. Table 2 shows examples of such Fc engineering. Expression in production cell lines with altered fucosylation may also impact FcγR binding in order to modulate phar-macokinetics of the antibody.

TABLE 2

Examples of modifications to modulate antibody effector function. Unless otherwise noted, the mutations are on the IgG1 subclass (Wang, Mathieu, and Brezski 2018).

| Engineering and intended function | Mutation | Reference |
|---|---|---|
| Enhance ADCC | | |
| Increased FcγRIIIa binding | F243L/R292P/Y300L/V305I/P396L S239D/I332E S298A/E333A/K334A in one heavy chain: L234Y/L235Q/G236W/S239M/H268 D/D270E/S298A, in the opposing heavy chain: D270E/K3 26D/A3 3 0M/K3 3 4E | (Stavenhagen et al. 2007) (Lazar et al. 2006) (Shields et al. 2001) (Mimoto et al. 2013) |
| Increased FcγRIIIa binding, decreased FcγRIIb binding Enhance ADCP | S239D/I332E/A330L | (Lazar et al. 2006) |
| Increased FcγRIIa binding, Increased FcγRIIIa binding Enhance CDC | G236A/S239D/I332E | (Richards et al. 2008) |
| Increased C1q binding | K326W/E333S S267E/H268F/S324T IgG1/IgG3 cross subclass | (Idusogie et al. 2001) (Moore et al. 2010) (Natsume et al. 2008) |
| Hexamerization Reduce effector function | E345R/E430G/S440Y | (Diebolder et al. 2014) |
| Aglycosylated | N297A or N297Q or N297G | (Bolt et al. 1993; Leabman et al. 2013; Tao and Morrison 1989; Walker et al. 1989) |

TABLE 2-continued

Examples of modifications to modulate antibody effector function. Unless otherwise noted, the mutations are on the IgG1 subclass (Wang, Mathieu, and Brezski 2018).

| Engineering and intended function | Mutation | Reference |
|---|---|---|
| Reduced FcγR and C1q binding | L235E<br>IgG1: L234A/L235A or L234A/L235A/P329G<br>IgG4:F234A/L235A<br>IgG2/IgG4 cross isotype<br>IgG2: H268Q/V309L/A330S/P331S<br>IgG2: V234A/G23 7A/P23 8 S/H268A/V3 09 L/A330S/P331S | (Alegre et al. 1992)<br>(Xu et al. 2000; Lo etal. 2017)<br>(Xu et al. 2000)<br>(Rother et al. 2007)<br>(An et al. 2009)<br>(Vafa etal. 2014) |
| Increase half-life | | |
| Increased FcRn Binding at pH 6.0 | M252Y/S254T/T256E<br>M428L/N434S | (Dall'Acqua et al. 2002)<br>(Zalevsky et al. 2010) |
| Increased coengagement | | |
| Increased FcγRIIb binding | S267E/L328F | (Chuetal. 2008) |
| Increased FcγRIIa binding, decreased FcγRIIIa binding | N325S/L328F | (Shang et al. 2014) |

In vivo half-life of antibodies may also be modulated. The Fc domain plays a central role in the stability and serum half-life on antibodies. For therapeutic approaches, antibody half-life may be reduced by using an antibody fragment missing the Fc domain or with truncated Fe domains, such as F(ab)$_2$, scFv, IgGΔCH2, F(ab')$_2$, scFvCH3, Fab, VL, VH, scFv4, scFv3, scFv2, dsFv, Fv, scFv-Fc or (scFv)$_2$. The antibodies may also be in the form of diabodies or bivalent antibodies, Diabodies or bivalent antibodies may be used to increase the affinity to the target allowing lower dosage. Functional fragments missing the Fc domain or with truncated Fc domains may also be used in the development of other therapeutic approaches such as chimeric antigen receptor T cell (CART cells) or bispecific T cell engagers (BiTEs™). In CAR constructs, one VH and one VL domain are typically connected by a short peptide linker to form a single-chain variable fragment (scFv), and the scFv fragment is further linked to a transmembrane domain and an intracytoplasmic T cell immunoreceptor tyrosine-based activation motif (from e.g. CD3ζ) and further domains of co-stimulatory molecules (from e.g. CD28, 4-1BB (CD127), or OX40) (Chang and Chen 2017). The VH and VL domains used in the scFv fragment may be the ones of the antibodies listed in Table 3. BiTEs™ typically consist of the on of two scFv of two different antibodies. One scFv domain may be of the isolated antibodies binding CLDN18.2 listed in Table 3, while the other scFv domain is from an antibody that binds e.g. to CD3, CD16, NKG2D, NKp46, CD2, CD28 or CD25. Ample guidance on BiTEs™ antibody formats and other bispecific antibody formats used for T-cell redirecting may be found in the review by Diego Ellerman (2019).

In another embodiment, the invention provides a humanized antibody or fragment thereof that binds to CLDN18.2, the antibody having the constant light chain region (CL) of SEQ ID NO: 65 and preferably the constant heavy chain region CH1 and Fc region of SEQ ID NO: 66 with reduced FcγR binding having the L234A/L235A mutations in the constant heavy chain region CH2. More preferably, the invention provides for an antibody with the constant heavy chain region CH1 and Fc region of SEQ ID NO: 67 having the L234A/L235A/P329G mutations in the constant heavy chain region CH1 and Fc region with even further reduced FcγR binding.

In another embodiment, the invention provides an isolated humanized antibody or fragment thereof that binds to CLDN18.2 with a VH sequence of SEQ ID NO: 41 associated to the constant heavy chain region CH1 and Fc region of SEQ ID NO: 66 and the VL sequence of SEQ ID NO: 33 associated to having the constant light chain region (CL) of SEQ ID NO: 65.

In yet another embodiment, the invention provides an antibody or fragment thereof binding to CLDN18.2, wherein the antibody or fragment thereof does not bind to CLDN18.1. Hence, the antibody does not exhibit cross-reactivity or cross-binding to CLDN18.1. Binding of an antibody to a target protein can be tested by flow cytometry on cells expressing the target protein. Specific binding of a tested antibody to its target protein can be visualized on a histogram plot. Such plot results in a peak with high fluorescent signal when the antibody specifically binds to the expressed target protein, and in a peak with low fluorescent signal when the antibody does not, or only very weakly bind to the expressed target protein. Such histogram can be seen in FIG. 1, showing binding of antibodies of the invention to CLDN18.2 but not to CLDN18.1 expressed in HEK293T cells. The degree of binding can also be expressed in a bar graph showing the maximal mean fluorescent intensity (maxMFI) measured by flow cytometry, with high maxMFI reflecting strong binding and low/no maxMFI reflecting non-binding. Examples of such binding assays can be found in Example 4.

In another embodiment, the invention provides an antibody or fragment thereof binding to CLDN18.2, the antibody being bound to another moiety. This moiety may include radioisotopes, fluorescent tags, histological markers, cytotoxins or cytokines. Binding of the moiety may be facilitated by linkers known in the art.

In yet another embodiment, the invention provides an antibody or fragment binding to CLDN18.2, wherein the antibody or fragment thereof exhibits stronger binding to CLDN18.2 than antibody IMAB362. Preferably, the invention provides an antibody or fragment binding to CLDN18.2, wherein the antibody or fragment thereof binds with a higher affinity to CLDN18.2 than antibody IMAB362. Binding affinities and/or rate constants can be determined using techniques well known in the art or described herein, such as ELISA, flow cytometry titration, isothermal titration calorimetry (ITC). Biacore™ (SPR), biolayer inferometry or fluorescent polarization. The inventors have determined the affinity of the antibodies to CLDN18.2 by ELISA as shown for example in Example 3 or by FC titration experiments as shown in Example 4. In ELSA on lipoparticles containing CLDN18.2, all the humanized antibodies hGBA-1 to hGBA-9 have a higher maximum binding values (expressed in MFI) than IMAB362. In FC titration experiments on HEK293T cells overexpressing CLDN18.2 or PA-TU-8988S cells endogenously expressing CLDN18.2, all the humanized antibodies hGBA-1 to hGBA-9 have higher maximum binding values (expressed in MFI units) and lower EC50 values (expressed in µg/ml) than the antibody IMAB362, indicative of higher affinity of the humanized antibodies of the present invention to CLDN18.2 than antibody IMAB362. In one embodiment, the antibodies provided in the invention have a measured EC50 value at least 10% lower, at least 20% lower, at least 40% lower, at least 50% lower or at least 75% lower than the EC50 value measured for antibody IMAB362. In one embodiment, the antibodies provided have a measured maxMFI value at least 10% higher, at least 20% higher, at least 40% higher, at least 50% higher or at least 75% higher than the maxMFI value measured for antibody IMAB362.

The heavy and light chain sequences of the IMAB362 antibody are e.g. provided herein as SEQ ID NO: 47 and SEQ ID NO: 48.

According to one embodiment, the invention provides nucleic acid sequences encoding the antibodies or fragments thereof binding to CLDN18.2. The nucleic acid sequences may encode for the CDRs alone, for the VH and VL regions, or for the entire heavy and light chains of the antibodies. These nucleic acid sequences may be found in Table 3. The nucleic acid sequence may also encode for F(ab)$_2$, Fv, scFv, IgGACH2, F(ab')$_2$, scFvCH3, Fab, VL, VH, scFv4, scFv3, scFv2, dsFv, Fv, scFv-Fc, (scFv)$_2$, a non-depleting IgG, a diabody, a bivalent antibody or Fc-engineered versions thereof. The encoded immunoglobin may be an IgA1, IgA2, IgD, IgE, IgG1, IdG2, IgG3, IgG4, synthetic IgG, IgM or mutated and Fc-engineered versions thereof.

In yet another embodiment, the invention provides an antibody-based binding protein that binds to CLDN18.2, e.g. a protein comprising at least a CLDN18.2 binding domain of the disclosed antibodies and another protein domain not related to antibodies. The invention also provides for a modified humanized antibody format that binds to CLDN18.2. In a preferred embodiment, the antibody-based binding protein does not bind to CLDN18.1.

In another embodiment, the invention provides for a nucleic acid encoding the antibody or fragment thereof. Such nucleic acid sequence may further encode for other elements and may be part of a chimeric antigen receptor (CAR) that binds to CLDN18.2. Ample guidance on construction of CAR T cells may be found in Chang and Chen (2017) or June and Sadelain (2018). In one embodiment, the invention provides a T cell that has been genetically engineered to produce an artificial T-cell receptor, wherein the artificial T-cell receptor comprises the antibody or functional fragment thereof of the present invention that binds to CLDN18.2. In a preferred embodiment, the CAR construct does not bind to CLDN18.1.

The invention also provides expression vectors comprising such nucleic acids. The expression vectors may be expression vectors aimed for mammalian cells, bacteria, fungal or insect cell expression, and chosen for the type of host cell bearing the expression vector comprising the nucleic acid encoding the antibodies or functional fragments thereof. Ample guidance for the construction of such vectors may be found in Green and Sambrook (Green and Sambrook 2012). Preferred are expression vectors for mammalian cells, especially CHO cells.

In another embodiment, the invention provides for host cells comprising the expression vectors of encoding the antibodies or fragments thereof binding to CLDN18.2 or having the nucleic acids encoding the antibodies or fragments thereof binding to CLDN18.2 integrated into its genome. The host cell may be a mammalian cell or cell line, bacteria, fungal or insect cell. Preferred are mammalian cells, especially CHO cells.

In another embodiment, the invention relates to an antibody or fragment thereof binding to CLDN18.2, the nucleic acid encoding the antibody or fragment thereof, the vector comprising the nucleic acid or the host cells comprising the nucleic acid or the vector comprising the nucleic acid, as described herein, for use in the treatment of a subject that is suffering from a neoplastic disease, or is at risk of developing a neoplastic disease, and/or for the treatment of a subject being diagnosed for a neoplastic disease. The disclosed antibodies or fragments thereof may be used as monotherapy or preferably as combinations therapy with the established standard of care of the neoplastic disease.

In yet another embodiment, the invention provides for the use of an antibody or fragment thereof binding to CLDN18.2 as provided herein for the manufacture of a medicament for the treatment of the neoplastic disease.

The neoplastic disease may be at least one disease selected from the group consisting of pancreatic, gastric, esophageal, ovarian and lung cancer. It is understood that the neoplastic disease to be treated is characterized by overexpression of CLDN18.2.

Another embodiment of the invention provides a method to treat a neoplastic disease, including pancreatic, gastric, esophageal, ovarian or lung cancer, with an isolated humanized antibody or fragment thereof that binds to CLDN18.2 as provided herein, wherein the method comprises administering a therapeutically effective amount of the antibody or fragment thereof. The method of treatment may be a monotherapy or preferably a combination therapy with the established standard of care of the neoplastic disease.

Also provided is a pharmaceutical composition comprising the antibody or fragment thereof binding to CLDN18.2, the nucleic acid encoding the antibody or fragment thereof, the vector comprising the nucleic acid or the host cell comprising the nucleic acid or the vector comprising the nucleic acid and a pharmaceutically acceptable carrier.

Preferably, patients suffering from pancreatic, gastric, esophageal, ovarian or lung cancer may be treated with an isolated humanized antibody or fragment thereof that binds to CLDN18.2 as provided herein.

EXAMPLES

Example 1: Humanization of Fab Fragments

Figure 1A:
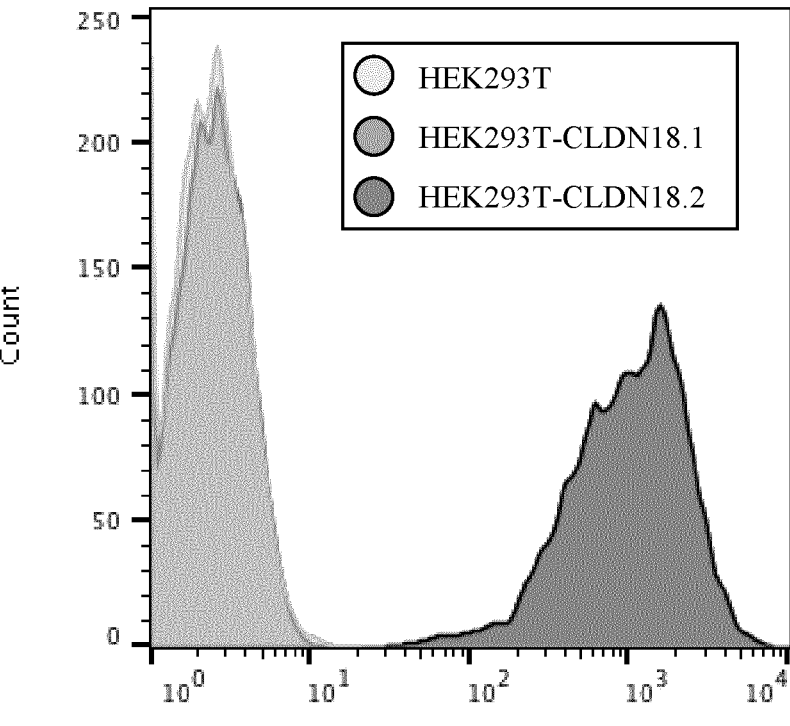
FIG. 1: FACS binding assay of humanized antibodies and IMAB362. Binding of selected antibodies to huCLDN1.2 and huCLDN18.1 was tested in HEK293T cells stably expressing huCLDN18.2 or huCLDN18.1. Parental HEK293T cells not expressing the target protein were used as negative control. 1A: A: IMAB362, B: hGBA-1, C: hGBA-2, D: hGBA-3, E: hGBA-4, F: hGBA-5, G: hGBA-6, H: hGBA-7, I: hGBA-8, J: GBA-9, K: secondary antibody alone, L: pan-CLDN18 antibody; 1B: Bar graph showing the Mean Fluorescent Intensity (MFI) of the FACS binding data for each humanized antibody, compared to IMAB362, on parental HEK293T cells and HEK293T cells expressing huCLDN18.2 or huCLDN18.1.
Figure 1A:
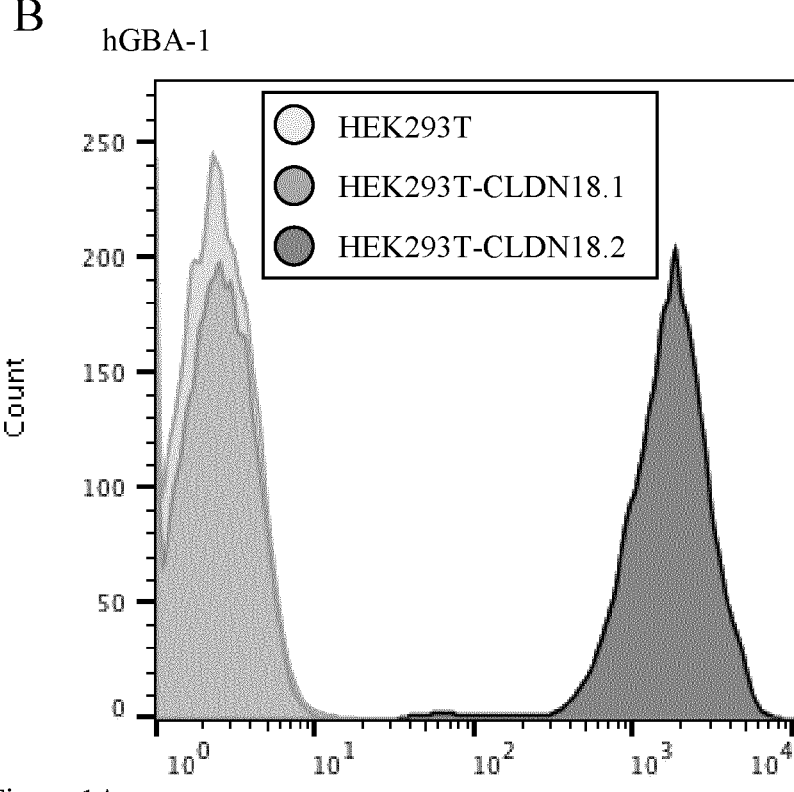
Figure 1A:
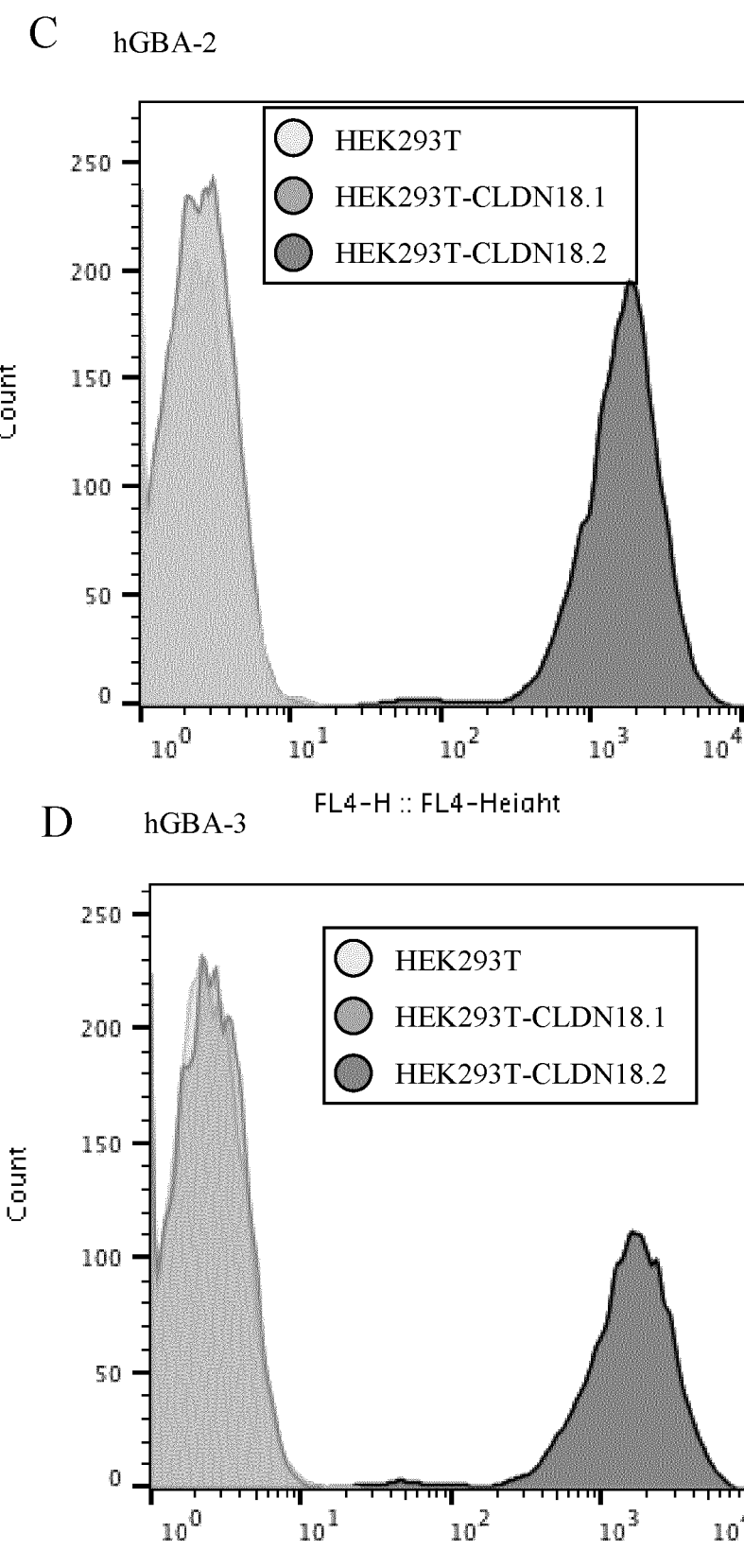
Figure 1A:
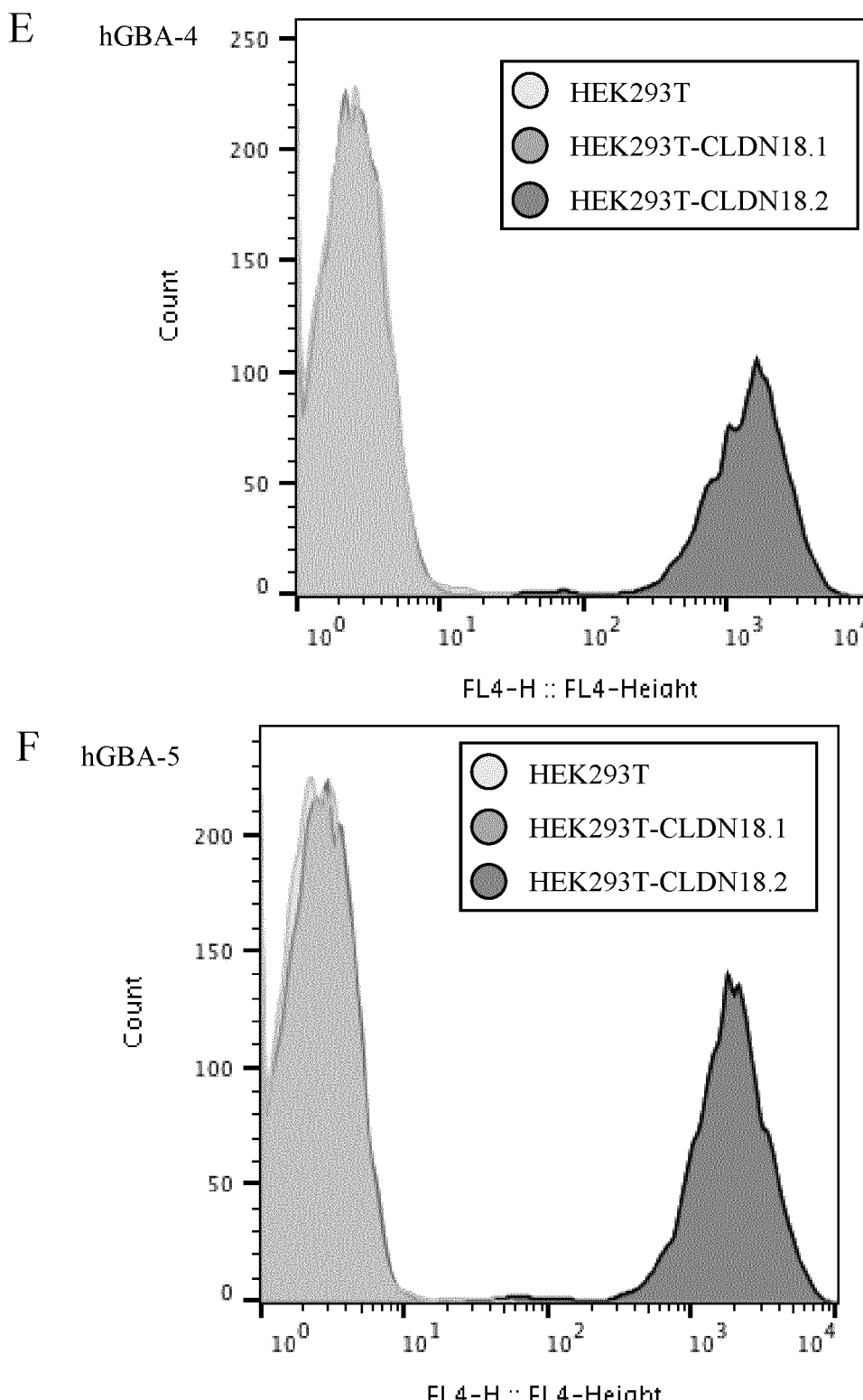
Figure 1A:
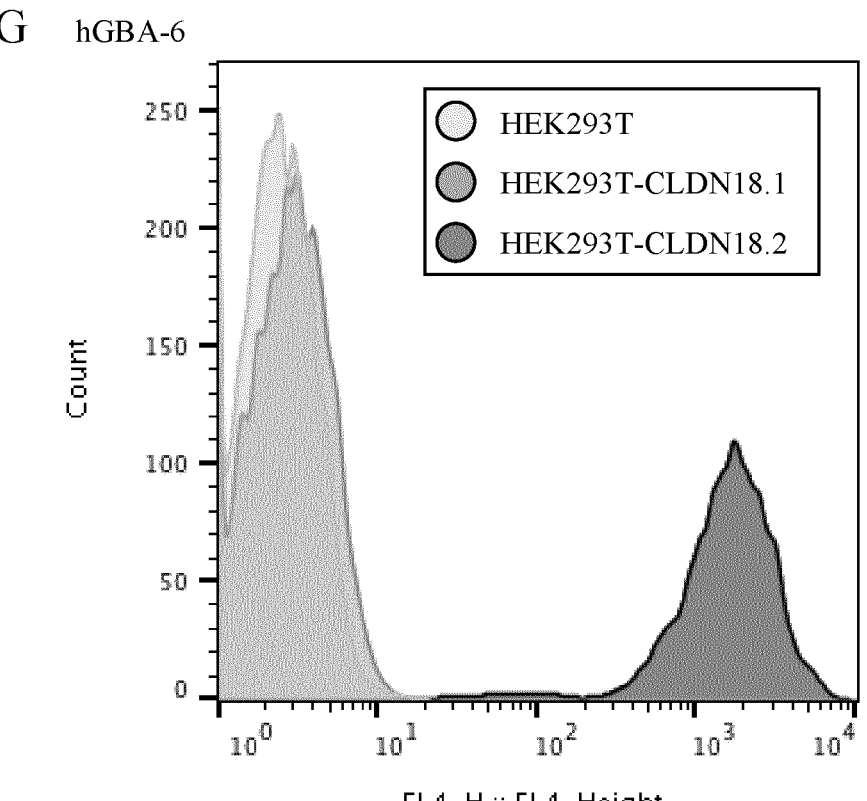
Figure 1A:
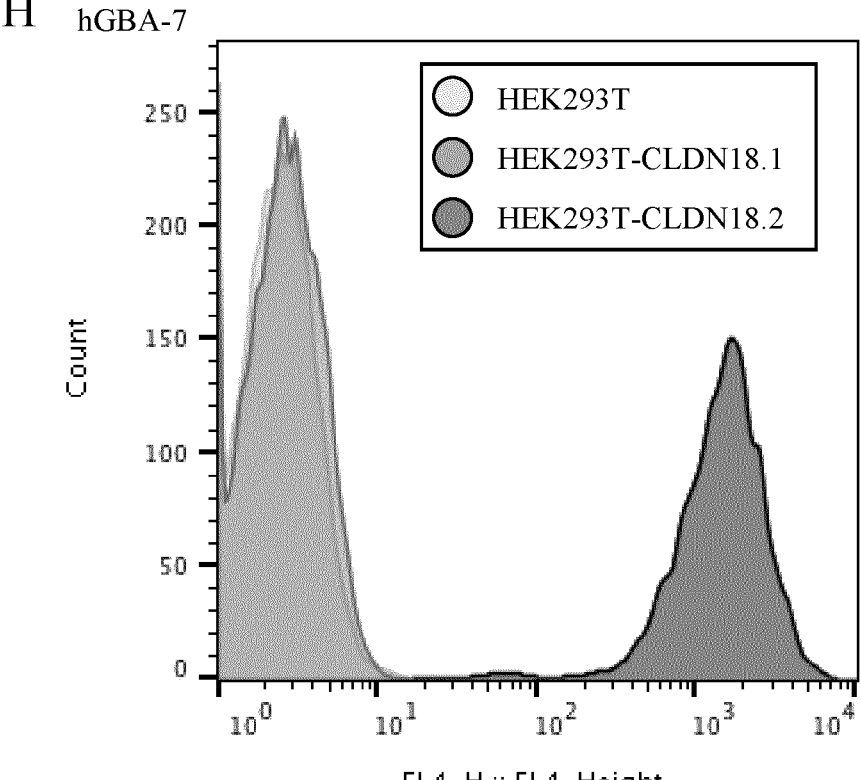
Figure 1A:
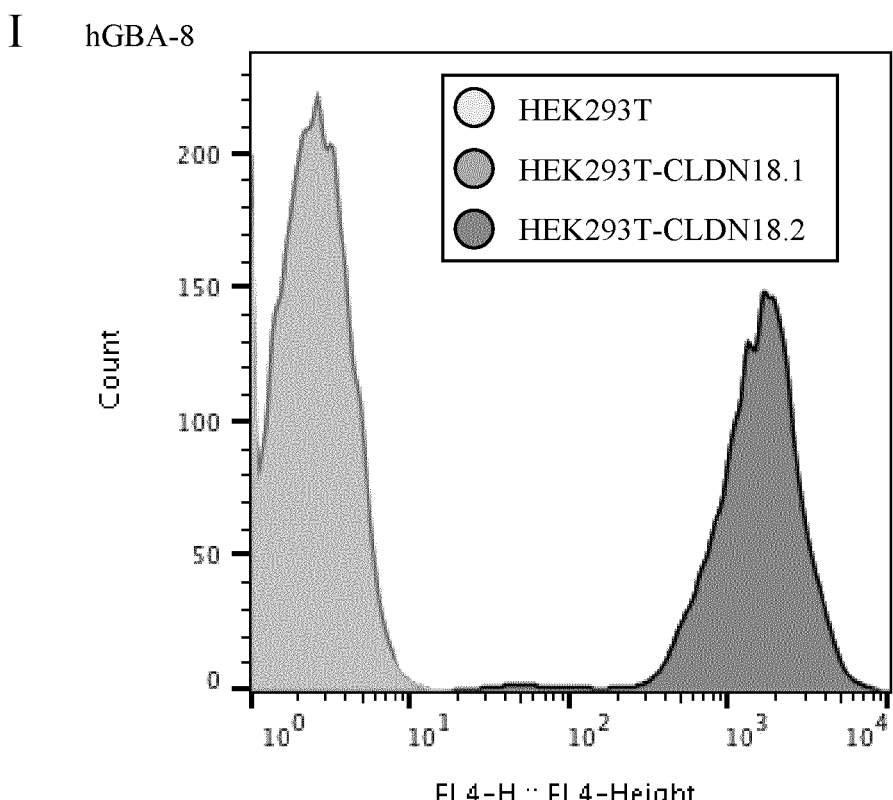
Figure 1A:
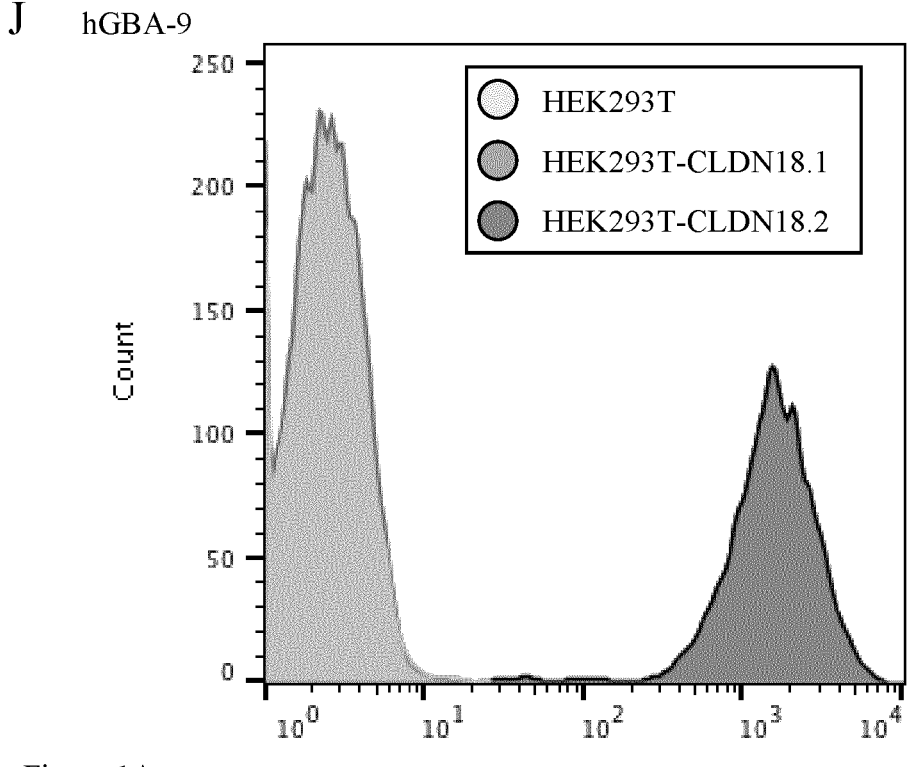
Figure 1A:
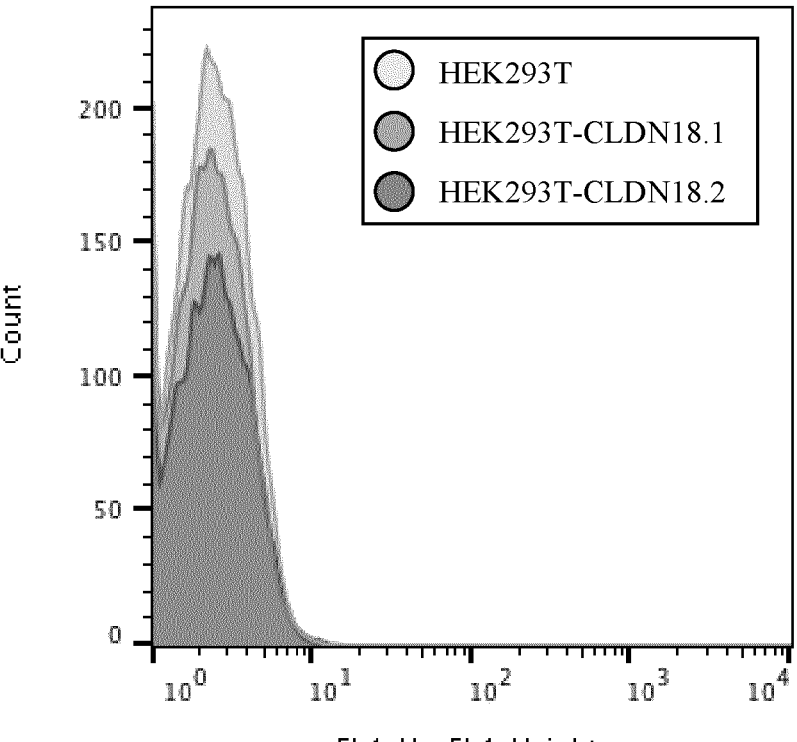
Figure 1A:
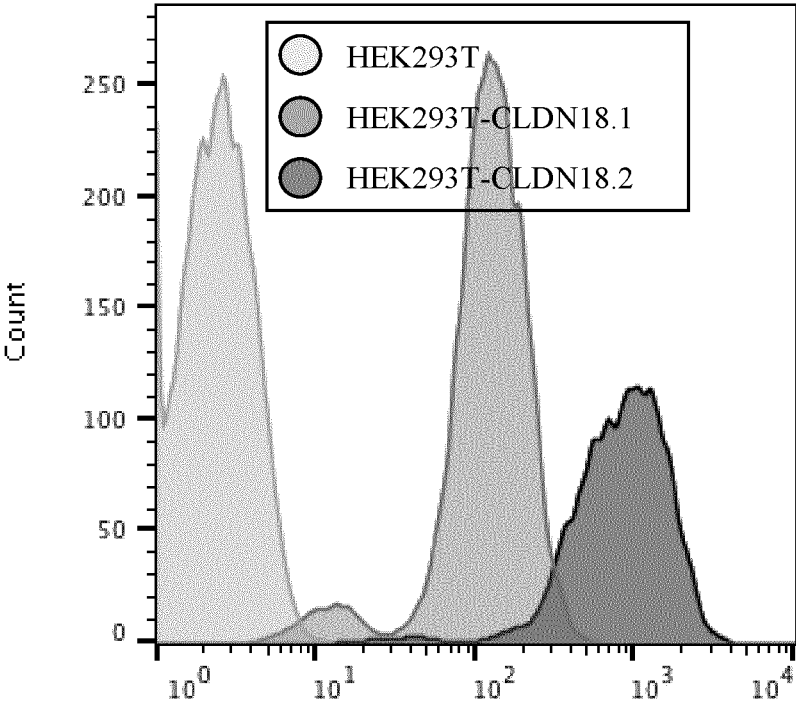
Figure 1B:
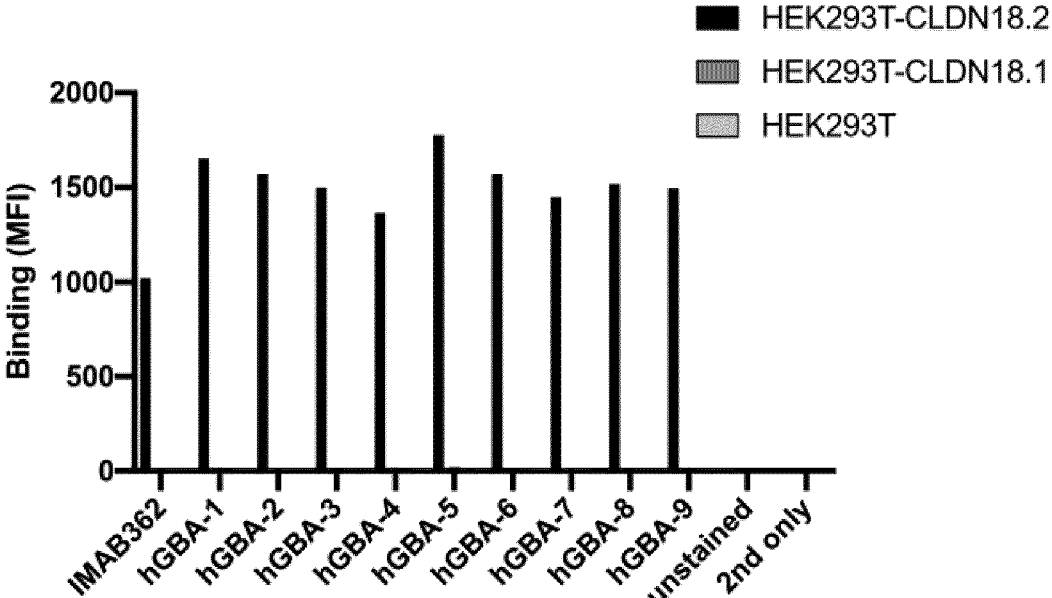
Figure 2A:
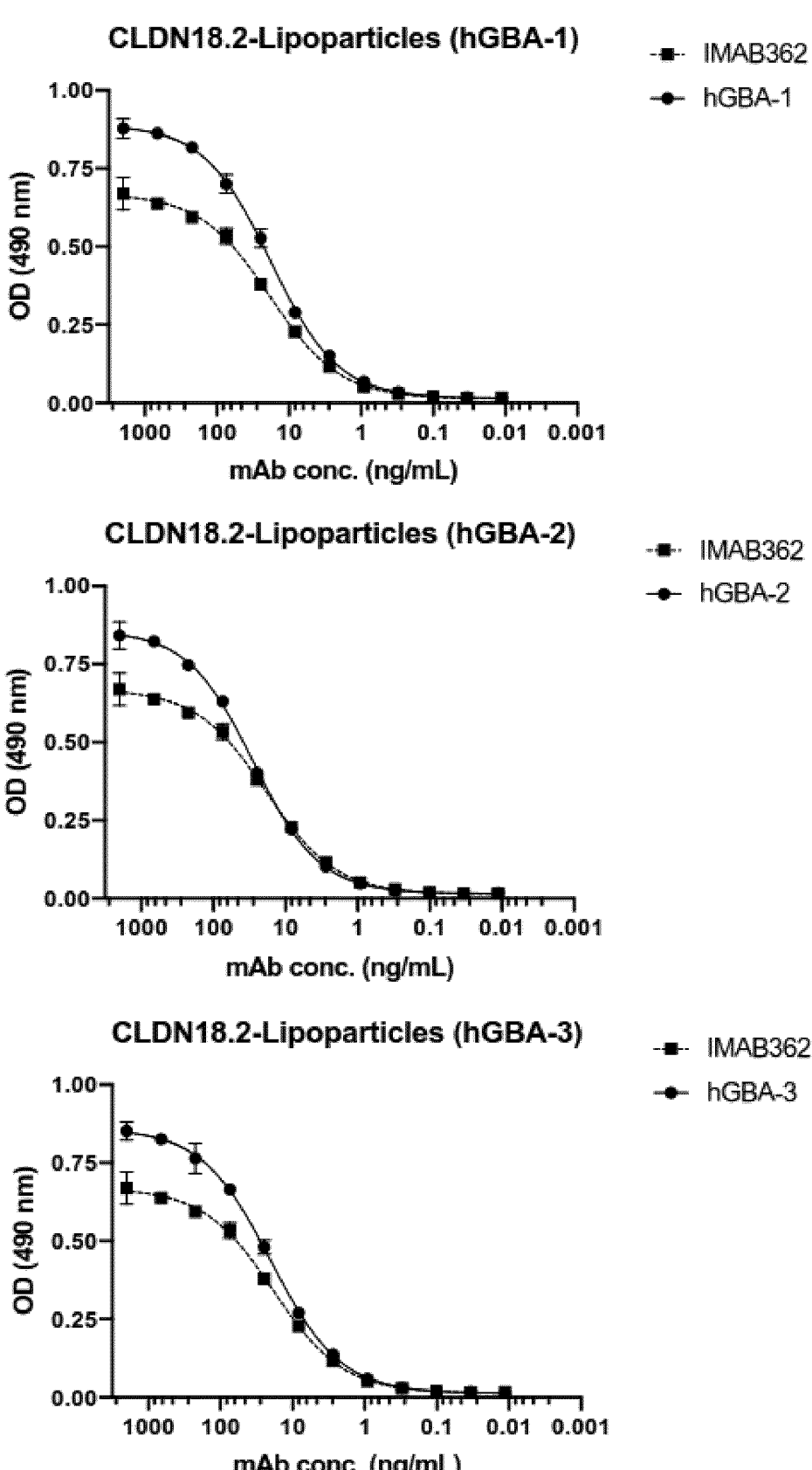
FIG. 2: 2A-D: ELISA binding assay on humanized antibodies, compared to IMAB362. The ELISA binding assay was performed on lipoparticles bearing CLDN18.2 or null-lipoparticles without CLDN18.2.
Figure 2B:
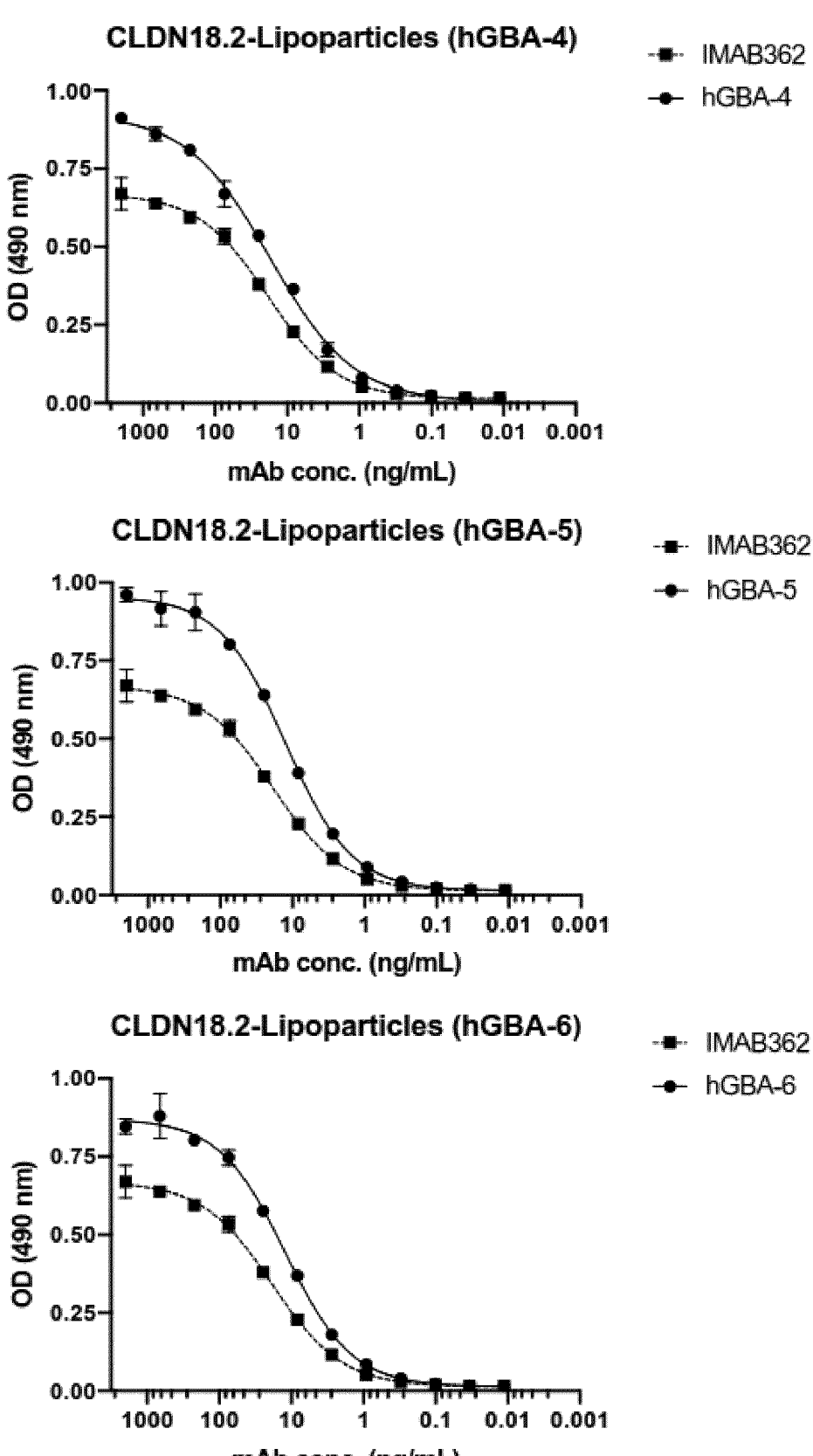
Figure 2C:
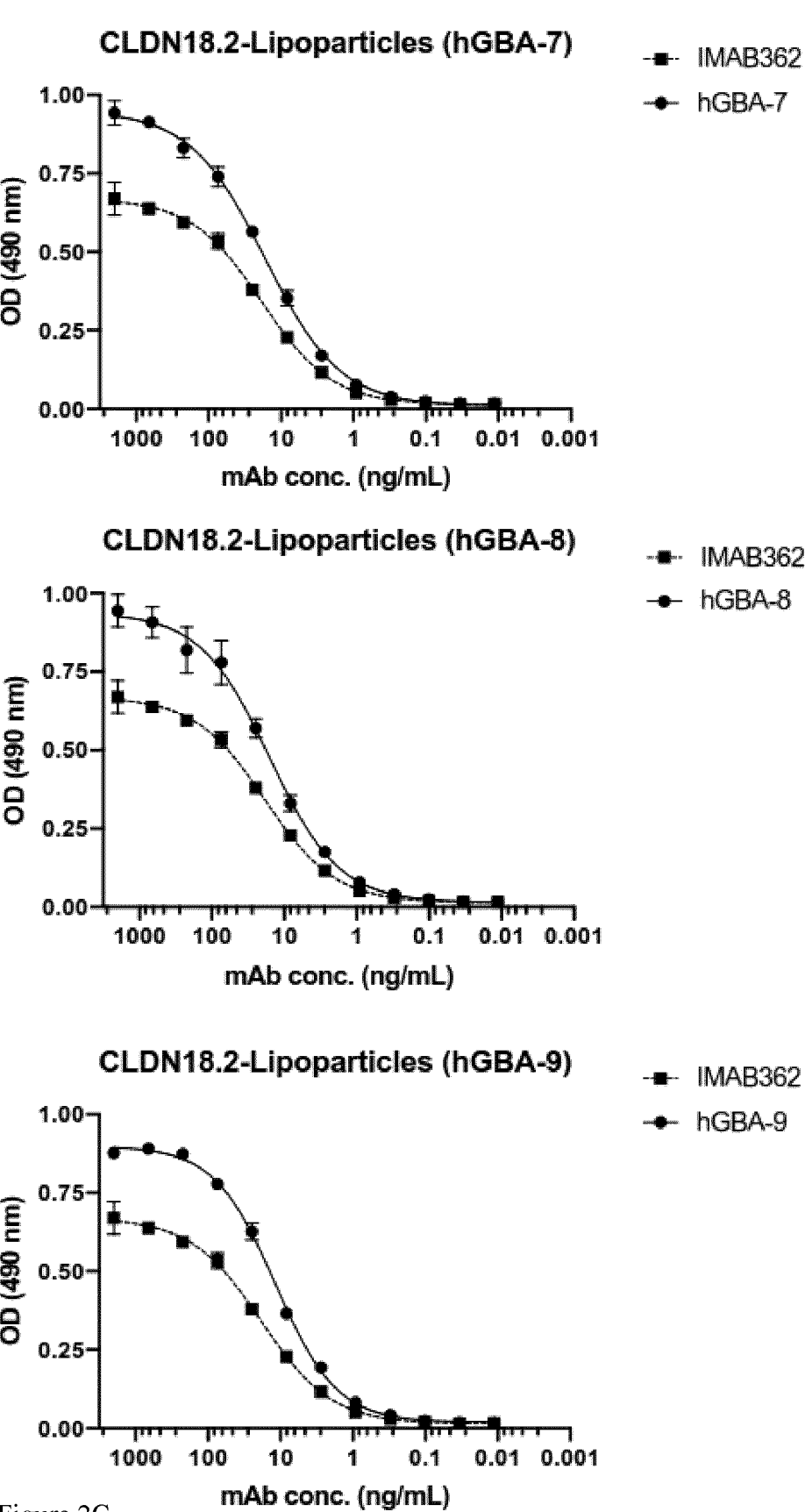
Figure 2D:
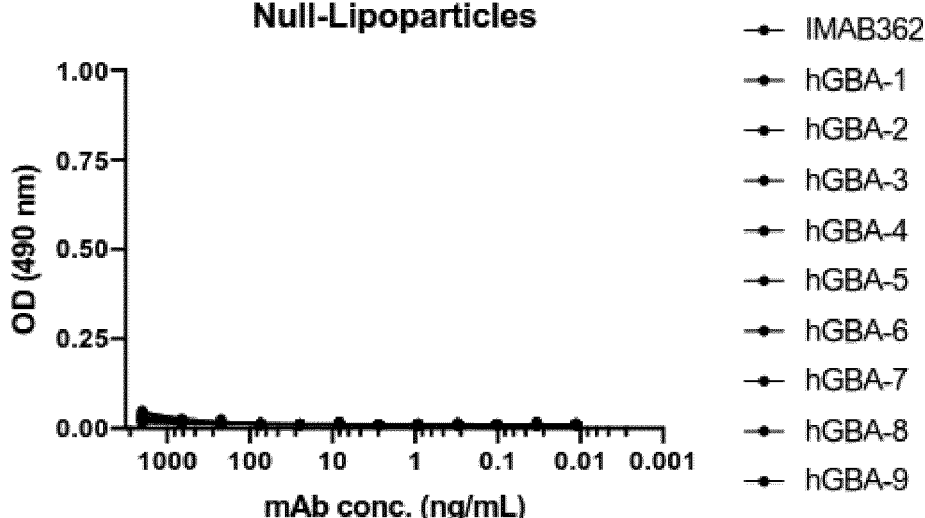

Techniques to humanize monoclonal antibodies have been well-established. The Handbook of Therapeutic Antibodies, Second Edition, gives ample information on humanization of monoclonal antibodies (Saldanha 2014), bioinformatic tools for analysis such antibodies (Martin and Allemn 2014) or development and manufacture of therapeutic antibodies (Jacobi et al. 2014), In brief, the variable domain sequences of the parental IMAB362 antibody were analyzed to reveal the closest human germlines. Next, a structural analysis of the variable regions of IMAB362 was performed to reveal the best fitting Fv model, followed by structural analysis of CDR grafting by in silico modeling. Based on these in-silico modeling, humanized VH and VL domains were designed. Combinations of the humanized VH and VL domains were cloned and produced as Fab and IgG1 antibodies and screened for their binding by ELISA and AlphaLISA™ to CLDN18.2-expressing lipoparticles and by flow cytometry with CLDN18.1- and CLDN18.2-expressing pre-B cell L11 (Waldmeier et al. 2016) and HEK293T (ATCC® CRL-3216™) cell lines. After testing and comparison to IMAB362, one VH and VL combination was selected and a library was designed in scFv format, performing further humanization including the CDRs. The scFv library was further screened by ELISA and AlphaLISA™ to CLDN18.2-expressing lipoparticles and by flow cytometry with CLDN18.1- and CLDN18.2-expressing pre-B cell L11 cell lines, Humanization of IMAB362 thus resulted in the humanized antibodies hGBA-1, hGBA-2, hGBA-3, hGBA-4, hGBA-5, hGBA-6, hGBA-7, hGBA-8 and hGBA-9 antibodies (see Table 3), collectively named hGBA antibodies herein.

TABLE 3

| nucleic acid and amino-acid sequences of selected antibodies | | |
|---|---|---|
| NAME | SEQUENCE | SEQ ID NO |
| | hGBA-1 | |
| HCDR1 | GYSFTSYWIG | SEQ ID NO: 7 |
| HCDR2 | GNIYPGASDTRYA | SEQ ID NO: 9 |
| HCDR3 | ARLWRGNSFDY | SEQ ID NO: 18 |
| VH | EVQLVQSGAEVKKPGESLKISCKGSGYSFTSYWIGWVRQMPGK GLEWMGNIYPGASDTRYAPSFQGQVTISADKSISTAYLQWSSL KASDTAMYYCARLWRGNSFDYWGQGTLVTVSS | SEQ ID NO: 32 |
| Heavy chain | EVQLVQSGAEVKKPGESLKISCKGSGYSFTSYWIGWVRQMPGK GLEWMGNIYPGASDTRYAPSFQGQVTISADKSISTAYLQWSSL KASDTAMYYCARLWRGNSFDYWGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSRDELTKNQVSLTCLVKGFYPSDIAVEWESNGQ PENNYKTTPPVLDSDGSFFLYSKLTVDKSRWQQGNVFSCSVMH EALHNHYTQKSLSLSPGK | SEQ ID NO: 49 |
| HCDR1 | ggctatagctttacatcatattggattgga | SEQ ID NO: 85 |
| HCDR2 | gggaacatttaccctggggcatcggatacgcgatacgca | SEQ ID NO: 86 |
| HCDR3 | gcgagactttggcgggggaatagcttcgactac | SEQ ID NO: 87 |
| VH | gaagtccaactggtccaatccggcgcggaggttaagaagcccg gagaatcgctgaagatctcatgcaaagggagcggctatagctt tacatcatattggattggatgggtcaggcaaatgccggggaag gggctggaatggatggggaacatttaccctggggcatcggata cgcgatacgcacctagctttcaagggcaagtcacaatttcggc ggacaagagcatctcaacggcatacctgcaatggtcgagcttg aaggcatctgatactgcaatgtactactgcgcgagactttggc gggggaatagcttcgactactggggcagggtaccctggttac ggtctcgagc | SEQ ID NO: 128 |
| LCDR1 | KSSQSLLNSGNQKNYLA | SEQ ID NO: 25 |
| LCDR2 | WASTRES | SEQ ID NO: 5 |
| LCDR3 | QNDYSYPFT | SEQ ID NO: 29 |
| VL | DIVMTQSPDSLAVSLGERATINCKSSQSLLNSGNQKNYLAWYQ QKPGQPPKLLIYWASTRESGVPDRFSGSGSGTDFTLTISSLQA EDVAVYYCQNDYSYPFTFGQGTKVEIK | SEQ ID NO: 33 |

TABLE 3-continued nucleic acid and amino-acid sequences of selected antibodies

| NAME | SEQUENCE | SEQ ID NO |
|---|---|---|
| Light chain | DIVMTQSPDSLAVSLGERATINCKSSQSLLNSGNQKNYLAWYQ QKPGQPPKLLIYWASTRESGVPDRFSGSGSGTDFTLTISSLQA EDVAVYYCQNDYSYPFTFGQGTKVEIKRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC | SEQ ID NO: 50 |
| LCDR1 | aaaagctcccaaagcctattgaactcgggaaaccaaaagaatt acttggca | SEQ ID NO: 88 |
| LCDR2 | tgggcaagcacccgagagagc | SEQ ID NO: 89 |
| LCDR3 | caaaacgactattcatacccattcaca | SEQ ID NO: 90 |
| VL | gacattgtgatgacgcaaagccccgattcgctggctgtatcgc taggggagcgcgctacgatcaattgcaaaagctcccaaagcct attgaactcgggaaaccaaaagaattacttggcatggtatcaa caaaaaccggggcaaccgccgaagctgctgatctattgggcaa gcacccgagagagcggtgtcccggaccgatttagcgggagcgg atcgggcaccgacttcacgctgacaataagctcattgcaagcc gaggatgtggcggtctattattgccaaaacgactattcatacc cattcacattcgggcaaggtaccaaggtcgagatcaag | SEQ ID NO: 129 | hGBA-2

| NAME | SEQUENCE | SEQ ID NO |
|---|---|---|
| HCDR1 | GYSFTSYWIG | SEQ ID NO: 7 |
| HCDR2 | GNIYPGDADTRYA | SEQ ID NO: 10 |
| HCDR3 | ARMWRGNSFDY | SEQ ID NO: 19 |
| VH | EVQLVQSGAEVKKPGESLKISCKGSGYSFTSYWIGWVRQMPGK GLEWMGNIYPGDADTRYAPSFQGQVTISADKSISTAYLQWSSL KASDTAMYYCARMWRGNSFDYWGQGTLVTVSS | SEQ ID NO: 34 |
| Heavy chain | EVQLVQSGAEVKKPGESLKISCKGSGYSFTSYWIGWVRQMPGK GLEWMGNIYPGDADTRYAPSFQGQVTISADKS1STAYLQWSSL KASDTAMYYCARMWRGNSFDYWGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSRDELTKNQVSLTCLVKGFYPSDIAVEWESNGQ PENNYKTTPPVLDSDGSFFLYSKLTVDKSRWQQGNVFSCSVMH EALHNHYTQKSLSLSPGK | SEQ ID NO: 51 |
| HCDR1 | ggatattcatttacaagctactggatcgga | SEQ ID NO: 91 |
| HCDR2 | ggaaatatataccccggagacgcggacacgagatacgca | SEQ ID NO: 92 |
| HCDR3 | gcgcggatgtggcgcggcaatagctttgactac | SEQ ID NO: 93 |
| VH | gaagtccaactggtccaatctggagcggaagtcaagaagcctg gggagagcctgaaaatttcatgcaaggggagcggatattcatt tacaagctactggatcggatgggtccggcaaatgccggggaag ggcttggaatggatgggaaatatataccccggagacgcggaca cgagatacgcaccgagctttcaagggcaggtcaccattagcgc tgataaatcgatttcaaccgcatatctgcaatggtcatcgctg aaggcctccgacaccgcgatgtactattgcgcgcggatgtggc gcggcaatagctttgactactggggggcagggtaccctcgtcac ggtctcgagc | SEQ ID NO: 130 |
| LCDR1 | KSSQSLLNSGNQKNYLA | SEQ ID NO: 25 |
| LCDR2 | WASTRES | SEQ ID NO: 5 |
| LCDR3 | QNDYSYPFT | SEQ ID NO: 29 |
| VL | DIVMTQSPDSLAVSLGERATINCKSSQSLLNSGNQKNYLAWYQ QKPGQPPKLLIYWASTRESGVPDRFSGSGSGTDFTLTISSLQA EDVAVYYCQNDYSYPFTFGQGTKVEIK | SEQ ID NO: 33 |
| Light chain | DIVMTQSPDSLAVSLGERATINCKSSQSLLNSGNQKNYLAWYQ QKPGQPPKLLIYWASTRESGVPDRFSGSGSGTDFTLTISSLQA EDVAVYYCQNDYSYPFTFGQGTKVEIKRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC | SEQ ID NO: 50 |
| LCDR1 | aaaagctcccaaagcctattgaactcgggaaaccaaaagaatt acttggca | SEQ ID NO: 88 |
| LCDR2 | tgggcaagcacccgagagagc | SEQ ID NO: 89 |
| LCDR3 | caaaacgactattcatacccattcaca | SEQ ID NO: 90 |
| VL | gacattgtgatgacgcaaagccccgattcgctggctgtatcgc taggggagcgcgctacgatcaattgcaaaagctcccaaagcct attgaactcgggaaaccaaaagaattacttggcatggtatcaa caaaaaccggggcaaccgccgaagctgctgatctattgggcaa gcacccgagagagcggtgtcccggaccgatttagcgggagcgg atcgggcaccgacttcacgctgacaataagctcattgcaagcc gaggatgtggcggtctattattgccaaaacgactattcatacc cattcacattcgggcaaggtaccaaggtcgagatcaag | SEQ ID NO: 129 |

TABLE 3-continued nucleic acid and amino-acid sequences of selected antibodies

| NAME | SEQUENCE | SEQ ID NO |
|---|---|---| hGBA-3

| NAME | SEQUENCE | SEQ ID NO |
|---|---|---|
| HCDR1 | GYSFTSYWIG | SEQ ID NO: 7 |
| HCDR2 | GIIYPGASDTNYA | SEQ ID NO: 11 |
| HCDR3 | ARIWRGNSFDY | SEQ ID NO: 20 |
| VH | EVQLVQSGAEVKKPGESLKISCKGSGYSFTSYWIGWVRQMPGK GLEWMGIIYPGASDTNYAPSFQGQVTISADKSISTAYLQWSSL KASDTAMYYCARIWRGNSFDYWGQGTLVTVSS | SEQ ID NO: 35 |
| Heavy chain | EVQLVQSGAEVKKPGESLKISCKGSGYSFTSYWIGWVRQMPGK GLEWMGIIYPGASDTNYAPSFQGQVTISADKSISTAYLQWSSL KASDTAMYYCARIWRGNSFDYWGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSRDELTKNQVSLTCLVKGFYPSDIAVEWESNGQ PENNYKTTPPVLDSDGSFFLYSKLTVDKSRWQQGNVFSCSVMH EALHNHYTQKSLSLSPGK | SEQ ID NO: 52 |
| HCDR1 | ggctatagctttacatcatattggattgga | SEQ ID NO: 85 |
| HCDR2 | gggatcatctatccgggggcatccgataccaactatgcg | SEQ ID NO: 94 |
| HCDR3 | gctaggatttggcgaggaaatagctttgattat | SEQ ID NO: 95 |
| VH | gaggtccaactggtccaaagcggcgcggaggtcaagaagccgg gagaatccctgaagattagctgcaaaggctccggctatagctt tacatcatattggatcggatgggtcagacaaatgccgggaaag ggacttgaatggatggggatcatctatccgggggcatccgata ccaactatgcgccgagcttccaagggcaggtcacgatatccgc ggataaatcgattagcaccgcatatctgcaatggagctcgctg aaggcatccgacaccgcgatgtactactgcgctaggatttggc gaggaaatagctttgattattgggggcagggtacccttgtcac ggtctcgagc | SEQ ID NO: 131 |
| LCDR1 | KSSQSLLNSGNQKNYLA | SEQ ID NO: 25 |
| LCDR2 | WASTRES | SEQ ID NO: 5 |
| LCDR3 | QNDYSYPLT | SEQ ID NO: 29 |
| VL | DIVMTQSPDSLAVSLGERATINCKSSQSLLNSGNQKNYLAWYQ QKPGQPPKLLIYWASTRESGVPDRFSGSGSGTDFTLTISSLQA EDVAVYYCQNDYSYPLTFGQGTKVEIK | SEQ ID NO: 36 |
| Light chain | DIVMTQSPDSLAVSLGERATINCKSSQSLLNSGNQKNYLAWYQ QKPGQPPKLLIYWASTRESGVPDRFSGSGSGTDFTLTISSLQA EDVAVYYCQNDYSYPLTFGQGTKVEIKRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC | SEQ ID NO: 53 |
| LCDR1 | aagagctcgcaaagtttgctgaactccgggaaccaaaagaatt acctggca | SEQ ID NO: 96 |
| LCDR2 | tgggcatcaacgcgggaaagc | SEQ ID NO: 97 |
| LCDR3 | caaaacgactactcctatccgctgacc | SEQ ID NO: 98 |
| VL | gacattgtcatgacgcaaagccccgactcgctggccgtctcac tggggagcgggcgacaatcaactgcaagagctcgcaaagtttt gctgaactccgggaaccaaaagaattacctggcatggtatcaa caaaagccggggcaacccccgaagctgctgatatattgggcat caacgcgggaaagcggagtcccggatagatttagcggatctgg atcggggaccgacttcacgctgacgatatctagccttcaagcc gaggatgtggctgtatattattgccaaaacgactactcctatc cgctgaccttcgggcaaggtaccaaggtcgagatcaag | SEQ ID NO: 132 | hGBA-4

| NAME | SEQUENCE | SEQ ID NO |
|---|---|---|
| HCDR1 | GYSFTSYWIG | SEQ ID NO: 7 |
| HCDR2 | GIIYPGDAYTRYS | SEQ ID NO: 12 |
| HCDR3 | TRLWRGNSFDA | SEQ ID NO: 21 |
| VH | EVQLVQSGAEVKKPGESLKISCKGSGYSFTSYWIGWVRQMPGK GLEWMGIIYPGDAYTRYSPSFQGQVTISADKSISTAYLQWSSL KASDTAMYYCTRLWRGNSFDAWGQGTLVTVSS | SEQ ID NO: 37 |
| Heavy chain | EVQLVQSGAEVKKPGESLKISCKGSGYSFTSYWIGWVRQMPGK GLEWMGIIYPGDAYTRYSPSFQGQVTISADKSISTAYLQWSSL KASDTAMYYCTRLWRGNSFDAWGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSRDELTKNQVSLTCLVKGFYPSDIAVEWESNGQ PENNYKTTPPVLDSDGSFFLYSKLTVDKSRWQQGNVFSCSVMH EALHNHYTQKSLSLSPGK | SEQ ID NO: 54 |

TABLE 3-continued

| nucleic acid and amino-acid sequences of selected antibodies |||
| --- | --- | --- |
| NAME | SEQUENCE | SEQ ID NO |
| HCDR1 | ggatactcatttacatcatactggatagga | SEQ ID NO: 99 |
| HCDR2 | gggattatataccccggcgacgcttacactcgatattcg | SEQ ID NO: 100 |
| HCDR3 | acgaggctatggaggggaatagctttgatgcc | SEQ ID NO: 101 |
| VH | gaagtccaactagtccaaagcggagccgaagtcaagaaaccgg | SEQ ID NO: 133 |
| | gggagagccttaagatctcatgcaaggggagcggatactcatt | |
| | tacatcatactggataggatgggtcagacaaatgcccggcaag | |
| | gggctggaatggatgggggattatataccccggcgacgcttaca | |
| | ctcgatattcgccatcattccaagggcaggtcacgatatcggc | |
| | cgataaatcgatatccacggcatacctgcaatggagctcactg | |
| | aaagcatctgatacggcaatgtattattgcacgaggctatgga | |
| | gggggaatagctttgatgcctgggggcagggtaccctggtcac | |
| | ggtctcgagc | |
| LCDR1 | KSSQSLLNSGNQKNYLT | SEQ ID NO: 26 |
| LCDR2 | WASTRES | SEQ ID NO: 5 |
| LCDR3 | QNDYSYPLT | SEQ ID NO: 30 |
| VL | DIVMTQSPDSLAVSLGERATINCKSSQSLLNSGNQKNYLTWYQ | SEQ ID NO: 38 |
| | QKPGQPPKLLIYWASTRESGVPDRFSGSGSGTDFTLTISSLQA | |
| | EDVAVYYCQNDYSYPLTFGQGTKVEIK | |
| Light chain | DIVMTQSPDSLAVSLGERATINCKSSQSLLNSGNQKNYLTWYQ | SEQ ID NO: 55 |
| | QKPGQPPKLLIYWASTRESGVPDRFSGSGSGTDFTLTISSLQA | |
| | EDVAVYYCQNDYSYPLTFGQGTKVEIKRTVAAPSVFIFPPSDE | |
| | QLKSGTASVVCLLNNFYPREAKVQWKVDNALQSGNSQESVTEQ | |
| | DSKDSTYSLSSTLTLSKADYEKHKVYACEVTHQGLSSPVTKSF | |
| | NRGEC | |
| LCDR1 | aagagctcccaaagcctattgaactcgggaaatcaaaagaatt | SEQ ID NO: 102 |
| | atctgaca | |
| LCDR2 | tgggcctcgacaagggagagc | SEQ ID NO: 103 |
| LCDR3 | caaaatgactactcatacccgctgaca | SEQ ID NO: 104 |
| VL | gacatagttatgacacaatcgccggatagcctcgcggtcagcc | SEQ ID NO: 134 |
| | ttggagagcgggcgacgatcaactgcaagagctcccaaagcct | |
| | attgaactcgggaaatcaaaagaattatctgacatggtatcaa | |
| | caaaagccggggcaaccaccgaaactgctgatctattgggcct | |
| | cgacaagggagagcggagtcccggaccgcttctctggatcggg | |
| | aagcgggactgacttcacgctgaccataagctcgctgcaagcc | |
| | gaggacgtcgccgtctattattgccaaaatgactactcatacc | |
| | cgctgacatttggccaaggtaccaaggtcgagatcaag | | hGBA-5

| | | |
| --- | --- | --- |
| HCDR1 | GYSFTSYWIG | SEQ ID NO: 7 |
| HCDR2 | GIIYPGAAYTRYA | SEQ ID NO: 13 |
| HCDR3 | ARLWRGNSFDY | SEQ ID NO: 18 |
| VH | EVQLVQSGAEVKKPGESLKISCKGSGYSFTSYWIGWVRQMPGK | SEQ ID NO: 39 |
| | GLEWMGIIYPGAAYTRYAPSFQGQVTISADKSISTAYLQWSSL | |
| | KASDTAMYYCARLWRGNSFDYWGQGTLVTVSS | |
| Heavy chain | EVQLVQSGAEVKKPGESLKISCKGSGYSFTSYWIGWVRQMPGK | SEQ ID NO: 56 |
| | GLEWMGIIYPGAAYTRYAPSFQGQVTISADKSISTAYLQWSSL | |
| | KASDTAMYYCARLWRGNSFDYWGQGTLVTVSSASTKGPSVFPL | |
| | APSSKSTSGGTAALGCLVKDYFPEPVTVSWNSGALTSGVHTFP | |
| | AVLQSSGLYSLSSVVTVPSSSLGTQTYICNVNHKPSNTKVDKK | |
| | VEPKSCDKTHTCPPCPAPELLGGPSVFLFPPKPKDTLMISRTP | |
| | EVTCVVVDVSHEDPEVKFNWYVDGVEVHNAKTKPREEQYNSTY | |
| | RVVSVLTVLHQDWLNGKEYKCKVSNKALPAPIEKTISKAKGQP | |
| | REPQVYTLPPSRDELTKNQVSLTCLVKGFYPSDIAVEWESNGQ | |
| | PENNYKTTPPVLDSDGSFFLYSKLTVDKSRWQQGNVFSCSVMH | |
| | EALHNHYTQKSLSLSPGK | |
| HCDR1 | ggatatagctttacgagctactggatcgga | SEQ ID NO: 105 |
| HCDR2 | gggataatataccccggagcggcatacacgagatatgcg | SEQ ID NO: 106 |
| HCDR3 | gcgagactatggcgcgggaactcatttgattac | SEQ ID NO: 107 |
| VH | gaggtgcaactggtacaatccggggcggaagtgaagaagccgg | SEQ ID NO: 135 |
| | gggaatcgctgaagataagctgcaaaggctctggatatagctt | |
| | tacgagctactggatcggatgggtcaggcaaatgccggggaag | |
| | ggactggaatggatggggataatataccccggagcggcataca | |
| | cgagatatgcgccgagcttccaagggcaagtgacaataagcgc | |
| | ggacaaatcgattagcacggcatatctgcaatggtcctcgctg | |
| | aaggcgagcgataccgcaatgtactattgcgcgagactatggc | |
| | gcgggaactcatttgattactggggcagggtaccctagtgac | |
| | ggtctcgagc | |
| LCDR1 | KSSQSLLNSGNQKNYLA | SEQ ID NO: 25 |
| LCDR2 | WASTRES | SEQ ID NO: 5 |
| LCDR3 | QQDYSYPFT | SEQ ID NO: 31 |
| VL | DIVMTQSPDSLAVSLGERATINCKSSQSLLNSGNQKNYLAWYQ | SEQ ID NO: 40 |
| | QKPGQPPKLLIYWASTRESGVPDRFSGSGSGTDFTLTISSLQA | |
| | EDVAVYYCQQDYSYPFTFGQGTKVEIK | |

TABLE 3-continued

| | nucleic acid and amino-acid sequences of selected antibodies | |
|---|---|---|
| NAME | SEQUENCE | SEQ ID NO |
| Light chain | DIVMTQSPDSLAVSLGERATINCKSSQSLLNSGNQKNYLAWYQ QKPGQPPKLLIYWASTRESGVPDRFSGSGSGTDFTLTISSLQA EDVAVYYCQQDYSYPFTFGQGTKVEIKRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC | SEQ ID NO: 57 |
| LCDR1 | aaatcatcgcaatcattgctaaattcggggaaccaaaagaatt atttggca | SEQ ID NO: 108 |
| LCDR2 | tgggcatccacgagagaatcg | SEQ ID NO: 109 |
| LCDR3 | caacaagattattcatacccatttaca | SEQ ID NO: 110 |
| VL | gacattgtcatgacgcaaagcccggatagcctggctgtatcgc tgggggagagagcgacgatcaactgcaaatcatcgcaatcatt gctaaattcggggaaccaaaagaattatttggcatggtatcaa caaaagccggggcaaccgccgaaactgctgatttactgggcat ccacgagagaatcgggagtcccggaccgatttagcggatctgg gagcgggaccgatttcacgctgaccattagctcgctgcaagcg gaggatgtggcggtctattactgccaacaagattattcatacc catttacatttgggcaaggtaccaaggtcgagatcaag | SEQ ID NO: 136 |
| hGBA-6 | | |
| HCDR1 | GYTFTSYWIG | SEQ ID NO: 8 |
| HCDR2 | GNIYPGASYTRYS | SEQ ID NO: 14 |
| HCDR3 | TRQWRGNSFDY | SEQ ID NO: 22 |
| VH | EVQLVQSGAEVKKPGESLKISCKGSGYTFTSYWIGWVRQMPGK GLEWMGNIYPGASYTRYSPSFQGQVTISADKSISTAYLQWSSL KASDTAMYYCTRQWRGNSFDYWGQGTLVTVSS | SEQ ID NO: 41 |
| Heavy chain | EVQLVQSGAEVKKPGESLKISCKGSGYTFTSYWIGWVRQMPGK GLEWMGNIYPGASYTRYSPSFQGQVTISADKS1STAYLQWSSL KASDTAMYYCTRQWRGNSFDYWGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSRDELTKNQVSLTCLVKGFYPSDIAVEWESNGQ PENNYKTTPPVLDSDGSFFLYSKLTVDKSRWQQGNVFSCSVMH EALHNHYTQKSLSLSPGK | SEQ ID NO: 58 |
| HCDR1 | ggatatacatttacatcttactggatcgga | SEQ ID NO: 111 |
| HCDR2 | gggaacatttatcctggcgcgagctatacgcgctat | SEQ ID NO: 112 |
| HCDR3 | acccggcaatggagggggcaatagctttgactac | SEQ ID NO: 113 |
| VH | gaagtacaattggttcaatcggggggccgaagtcaagaagccgg gggaatcgctgaagatatcctgcaaggggagcggatatacatt tacatcttactggatcggatgggtcagacaaatgcccggaaag gggcttgaatggatggggaacatttatcctggcgcgagctata cgcgctatagcccgagcttccaagggcaggtcacgattagcgc cgacaagagcatttcgacggcatacctgcaatggagctcgctg aaagcatcggatacggcaatgtattactgcacccggcaatgga gggcaatagctttgactactggggggcagggtaccctagtcac ggtctcgagc | SEQ ID NO: 137 |
| LCDR1 | KSSQSLLNSGNQKNYLA | SEQ ID NO: 25 |
| LCDR2 | WASTRES | SEQ ID NO: 5 |
| LCDR3 | QNDYSYPFT | SEQ ID NO: 29 |
| VL | DIVMTQSPDSLAVSLGERATINCKSSQSLLNSGNQKNYLAWYQ QKPGQPPKLLIYWASTRESGVPDRFSGSGSGTDFTLTISSLQA EDVAVYYCQNDYSYPFTFGQGTKVEIK | SEQ ID NO: 33 |
| Light chain | DIVMTQSPDSLAVSLGERATINCKSSQSLLNSGNQKNYLAWYQ QKPGQPPKLLIYWASTRESGVPDRFSGSGSGTDFTLTISSLQA EDVAVYYCQNDYSYPFTFGQGTKVEIKRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC | SEQ ID NO: 50 |
| LCDR1 | aaaagctcccaaagcctattgaactcgggaaaccaaaagaatt acttggca | SEQ ID NO: 88 |
| LCDR2 | tgggcaagcacccgagagagc | SEQ ID NO: 89 |
| LCDR3 | caaaacgactattcatacccattcaca | SEQ ID NO: 90 |
| VL | gacattgtgatgacgcaaagccccgattcgctggctgtatcgc taggggagcgcgctacgatcaattgcaaaagctcccaaagcct attgaactcgggaaaccaaaagaattacttggcatggtatcaa caaaaaccggggcaaccgccgaagctgctgatctattgggcaa gcacccgagagagcggtgtcccggaccgatttagcgggagcgg atcgggcaccgacttcacgctgacaataagctcattgcaagcc gaggatgtggcggtctattattgccaaaacgactattcatacc cattcacatttcgggcaaggtaccaaggtcgagatcaag | SEQ ID NO: 129 |

TABLE 3-continued nucleic acid and amino-acid sequences of selected antibodies

| NAME | SEQUENCE | SEQ ID NO |
|---|---|---| hGBA-7

| NAME | SEQUENCE | SEQ ID NO |
|---|---|---|
| HCDR1 | GYSFTSYWIG | SEQ ID NO: 7 |
| HCDR2 | GNIYPGEAYTRYS | SEQ ID NO: 15 |
| HCDR3 | TRLWRGNSFDY | SEQ ID NO: 23 |
| VH | EVQLVQSGAEVKKPGESLKISCKGSGYSFTSYWIGWVRQMPGK GLEWMGNIYPGEAYTRYSPSFQGQVTISADKS1STAYLQWSSL KASDTAMYYCTRLWRGNSFDYWGQGTLVTVSS | SEQ ID NO: 42 |
| Heavy chain | EVQLVQSGAEVKKPGESLKISCKGSGYSFTSYWIGWVRQMPGK GLEWMGNIYPGEAYTRYSPSFQGQVTISADKS1STAYLQWSSL KASDTAMYYCTRLWRGNSFDYWGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSRDELTKNQVSLTCLVKGFYPSDIAVEWESNGQ PENNYKTTPPVLDSDGSFFLYSKLTVDKSRWQQGNVFSCSVMH EALHNHYTQKSLSLSPGK | SEQ ID NO: 59 |
| HCDR1 | ggatattcctttacatcatactggatcggc | SEQ ID NO: 114 |
| HCDR2 | gggaacatatatcccggagaagcctacgagatactcg | SEQ ID NO: 115 |
| HCDR3 | acgcgactatggaggggaaatagctttgactat | SEQ ID NO: 116 |
| VH | gaagttcaattggtccaatctggagccgaagtcaagaagcccg gagaatcgctgaagattagctgcaaggggagcggatattcctt tacatcatactggatcggctgggtcagacaaatgcccggaaag ggactggaatggatggggaacatatatcccggagaagcctata cgagatactcgccatcatttcaaggacaggtcaccataagcgc ggacaagagcataagcaccgcatacctgcaatggagctcgctg aaggcatcggacaccgccatgtattactgcacgcgactatgga ggggaaatagctttgactattggggggcagggtaccttagtcac ggtctcgagc | SEQ ID NO: 138 |
| LCDR1 | KSSQSVLNSGNQKNYLT | SEQ ID NO: 27 |
| LCDR2 | WASTRES | SEQ ID NO: 5 |
| LCDR3 | QNDYSYPFT | SEQ ID NO: 29 |
| VL | DIVMTQSPDSLAVSLGERATINCKSSQSVLNSGNQKNYLTWYQ QKPGQPPKLLIYWASTRESGVPDRFSGSGSGTDFTLTISSLQA EDVAVYYCQNDYSYPFTFGQGTKVEIK | SEQ ID NO: 43 |
| Light chain | DIVMTQSPDSLAVSLGERATINCKSSQSVLNSGNQKNYLTWYQ QKPGQPPKLLIYWASTRESGVPDRFSGSGSGTDFTLTISSLQA EDVAVYYCQNDYSYPFTFGQGTKVEIKRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC | SEQ ID NO: 60 |
| LCDR1 | aagagctcccaatcagtcctgaactctgggaatcaaaagaatt acctgaca | SEQ ID NO: 117 |
| LCDR2 | tgggcgagcacgagggagagc | SEQ ID NO: 118 |
| LCDR3 | caaaatgattattcatacccccttcaca | SEQ ID NO: 119 |
| VL | gatatagtaatgactcaatcacccgatagcttggctgtgagcc tgggagaaagagctacaatcaactgcaagagctcccaatcagt cctgaactctgggaatcaaaagaattacctgacatggtatcaa caaaagcccggacaaccgccgaagctgctgatctactgggcga gcacgagggagagcggagtcccggatcgatttctggctccgg gagcggaaccgacttcacactgactattagctcgctgcaagcg gaggacgtcgccgtctactattgccaaaatgattattcatacc ccttcacatttgggcaaggtaccaaggtcgagatcaag | SEQ ID NO: 139 | hGBA-8

| NAME | SEQUENCE | SEQ ID NO |
|---|---|---|
| HCDR1 | GYSFTSYWIG | SEQ ID NO: 7 |
| HCDR2 | GNIYPSESYTNYA | SEQ ID NO: 16 |
| HCDR3 | TRLWRGNSFDY | SEQ ID NO: 23 |
| VH | EVQLVQSGAEVKKPGESLKISCKGSGYSFTSYWIGWVRQMPGK GLEWMGNIYPSESYTNYAPSFQGQVTISADKSISTAYLQWSSL KASDTAMYYCTRLWRGNSFDYWGQGTLVTVSS | SEQ ID NO: 44 |
| Heavy chain | EVQLVQSGAEVKKPGESLKISCKGSGYSFTSYWIGWVRQMPGK GLEWMGNIYPSESYTNYAPSFQGQVTISADKSISTAYLQWSSL KASDTAMYYCTRLWRGNSFDYWGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSRDELTKNQVSLTCLVKGFYPSDIAVEWESNGQ PENNYKTTPPVLDSDGSFFLYSKLTVDKSRWQQGNVFSCSVMH EALHNHYTQKSLSLSPGK | SEQ ID NO: 61 |

TABLE 3-continued

| nucleic acid and amino-acid sequences of selected antibodies | | |
|---|---|---|
| NAME | SEQUENCE | SEQ ID NO |
| HCDR1 | ggatactcctttacatcatattggatcgga | SEQ ID NO: 120 |
| HCDR2 | ggaaacatatatccgagcgaatcatatacgaactacgcg | SEQ ID NO: 121 |
| HCDR3 | acgaggctatggagggggaatagcttcgactat | SEQ ID NO: 122 |
| VH | gaggtgcaactagtgcaatcggggggccgaagtgaagaaacctg<br>gggaatcgctgaagatatcatgcaaggggagcggatactcctt<br>tacatcatattggatcggatgggtcaggcaaatgccgggggaag<br>gggctggaatggatgggaaacatatatccgagcgaatcatata<br>cgaactacgcgccgagctttcaaggacaagtcacgatatccgc<br>ggataaatcgatatcgaccgcatacctgcaatggagctcgctg<br>aaggcttccgacactgcgatgtattactgcacgaggctatgga<br>gggggaatagcttcgactattgggggcagggtaccctggtgac<br>ggtctcgagc | SEQ ID NO: 140 |
| LCDR1 | KSSQSLLNSGNQKNYLA | SEQ ID NO: 25 |
| LCDR2 | WASTRES | SEQ ID NO: 5 |
| LCDR3 | QNDYSYPFT | SEQ ID NO: 29 |
| VL | DIVMTQSPDSLAVSLGERATINCKSSQSLLNSGNQKNYLAWYQ<br>QKPGQPPKLLIYWASTRESGVPDRFSGSGSGTDFTLTISSLQA<br>EDVAVYYCQNDYSYPFTFGQGTKVEIK | SEQ ID NO: 33 |
| Light chain | DIVMTQSPDSLAVSLGERATINCKSSQSLLNSGNQKNYLAWYQ<br>QKPGQPPKLLIYWASTRESGVPDRFSGSGSGTDFTLTISSLQA<br>EDVAVYYCQNDYSYPFTFGQGTKVEIKRTVAAPSVFIFPPSDE<br>QLKSGTASVVCLLNNFYPREAKVQWKVDNALQSGNSQESVTEQ<br>DSKDSTYSLSSTLTLSKADYEKHKVYACEVTHQGLSSPVTKSF<br>NRGEC | SEQ ID NO: 50 |
| LCDR1 | aaaagctcccaaagcctattgaactcgggaaaccaaaagaatt<br>acttggca | SEQ ID NO: 88 |
| LCDR2 | tgggcaagcacccgagagagc | SEQ ID NO: 89 |
| LCDR3 | caaaacgactattcatacccattcaca | SEQ ID NO: 90 |
| VL | gacattgtgatgacgcaaagccccgattcgctggctgtatcgc<br>taggggagcgcgctacgatcaattgcaaaagctcccaaagcct<br>attgaactcgggaaaccaaaagaattacttggcatggtatcaa<br>caaaaaccggggcaaccgccgaagctgctgatctattgggcaa<br>gcacccgagagagcggtgtcccggaccgatttagcgggagcgg<br>atcgggcaccgacttcacgctgacaataagctcattgcaagcc<br>gaggatgtggcggtctattattgccaaaacgactattcatacc<br>cattcacattcgggcaaggtaccaaggtcgagatcaagt | SEQ ID NO: 129 | hGBA-9

| HCDR1 | gytftsywig | SEQ ID NO |
|---|---|---|
| HCDR2 | GIIYPSAAYTRYA | SEQ ID NO: 17 |
| HCDR3 | TRMWRGNSFDY | SEQ ID NO: 24 |
| VH | EVQLVQSGAEVKKPGESLKISCKGSGYTFTSYWIGWVRQMPGK<br>GLEWMGIIYPSAAYTRYAPSFQGQVTISADKSISTAYLQWSSL<br>KASDTAMYYCTRMWRGNSFDYWGQGTLVTVSS | SEQ ID NO: 45 |
| Heavy chain | EVQLVQSGAEVKKPGESLKISCKGSGYTFTSYWIGWVRQMPGK<br>GLEWMGIIYPSAAYTRYAPSFQGQVTISADKSISTAYLQWSSL<br>KASDTAMYYCTRMWRGNSFDYWGQGTLVTVSSASTKGPSVFPL<br>APSSKSTSGGTAALGCLVKDYFPEPVTVSWNSGALTSGVHTFP<br>AVLQSSGLYSLSSVVTVPSSSLGTQTYICNVNHKPSNTKVDKK<br>VEPKSCDKTHTCPPCPAPELLGGPSVFLFPPKPKDTLMISRTP<br>EVTCVVVDVSHEDPEVKFNWYVDGVEVHNAKTKPREEQYNSTY<br>RVVSVLTVLHQDWLNGKEYKCKVSNKALPAPIEKTISKAKGQP<br>REPQVYTLPPSRDELTKNQVSLTCLVKGFYPSDIAVEWESNGQ<br>PENNYKTTPPVLDSDGSFFLYSKLTVDKSRWQQGNVFSCSVMH<br>EALHNHYTQKSLSLSPGK | SEQ ID NO: 62 |
| HCDR1 | ggatatacattcacgagctactggatagga | SEQ ID NO |
| HCDR2 | ggaatcatatatccttccgcggcatatacgcgatatgcg | SEQ ID NO: 124 |
| HCDR3 | acgcggatgtggaggggaaatagctttgattac | SEQ ID NO: 125 |
| VH | gaagtccaattagtccaatcggggggccgaggtcaagaagccgg<br>gggaatcgctcaagataagctgcaagggatcgggatatacatt<br>cacgagctactggataggatgggtcaggcaaatgccgggggaag<br>gggctggaatggatgggaatcatatatccttccgcggcatata<br>cgcgatatgcgccatcatttcaaggacaggtcacgataagcgc<br>cgacaagagcattagcaccgcatacctgcaatggtcgagcctt<br>aaggcatcggacaccgcgatgtactactgcacgcggatgtgga<br>ggggaaatagctttgattactggggcagggtaccctagtcac<br>ggtctcgagc | SEQ ID NO: 141 |
| LCDR1 | KSSQSVLNSGNQKNYLA | SEQ ID NO: 28 |
| LCDR2 | WASTRES | SEQ ID NO: 5 |
| LCDR3 | QQDYSYPFT | SEQ ID NO: 31 |
| VL | DIVMTQSPDSLAVSLGERATINCKSSQSVLNSGNQKNYLAWYQ<br>QKPGQPPKLLIYWASTRESGVPDRFSGSGSGTDFTLTISSLQA<br>EDVAVYYCQQDYSYPFTFGQGTKVEIK | SEQ ID NO: 46 |

TABLE 3-continued nucleic acid and amino-acid sequences of selected antibodies

| NAME | SEQUENCE | SEQ ID NO |
|------|----------|-----------|
| Light chain | DIVMTQSPDSLAVSLGERATINCKSSQSVLNSGNQKNYLAWYQ QKPGQPPKLLIYWASTRESGVPDRFSGSGSGTDFTLTISSLQA EDVAVYYCQQDYSYPFTFGQGTKVEIKRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC | SEQ ID NO: 63 |
| LCDR1 | aagagctcgcaatcggtcctgaatagcgggaaccaaaagaatt atctggcc | SEQ ID NO: 126 |
| LCDR2 | tgggcgagcacgagggagagc | SEQ ID NO: 118 |
| LCDR3 | caacaagactactcatacccatttaca | SEQ ID NO: 127 |
| VL | gacatcgtcatgacgcaaagcccggactcgctggcggtctcgc tggggagcgggccacaataaattgcaagagctcgcaatcggt cctgaatagcgggaaccaaaagaattatctggcctggtatcaa caaaagccggggcaaccaccgaagctgctaatctattgggcga gcacgagggagagcggagtccccgatcgatttagcggatcggg aagcgggaccgatttcacgctgacgatttcgagcctacaagcc gaggatgtggcggtctattactgccaacaagactactcatacc catttacatttggacaaggtaccaaggtcgagatcaag | SEQ ID NO: 142 |

The antibodies described in further Examples 2 to 4 were modified to contain a RLPXTGG tag (SEQ ID NO: 143) at the C-terminal end of the HC and/or a GGGGSLPXTGG tag (SEQ ID NO: 144) at the C-terminal end of the LC, where X is any of the 20 natural amino acids. The C-terminal lysine (K) on the HC was in this case replaced by the Arginine (R) of the tag. The addition of the tags did not change the affinity and selectivity to CLDN18.2 of the antibodies.

Example 2: FACS Binding Analysis of Humanized mAbs

The HEK293T (ATCC CRL-3216™) cell line does not endogenously express CLDN18.1 of CLDN18.2. Therefore, in order to test antibody binding activity, CLDN18.1 and CLDN18.2 were overexpressed in the HEK293T cell line. Cells were co-transfected by electroporation with a transposase expression construct (pcDNA3.1-by-mPB), construct bearing transposable full-length huCLDN18.1 (pPB-Puro-huCldn18.1) or huCLDN18.2 (pPB-Puro-huCldn18.2) along with puromycin expression cassette and a construct carrying EGFP as transfection control (pEGFP-N3). Upon transfection, cells were allowed to recover for two days in growth media at 37° C. in a humidified incubator in a 5% $CO_2$ atmosphere. Transfection was verified by FC analysis of the EGFP expression. Cells expressing huCLDN18.1 or huCLDN18.2 were then selected by the addition of puromycin into culture at 1 µg/ml, and further expanded to allow the generation of frozen stocks in FCS with 10% DMSO. The expression of huCLDN18.2 in the transfected HEK293T cells was analyzed by FACS. In brief, HEK293T cells were trypsinized and collected by centrifugation, resuspended in PBS/2% FCS and stained for huCLDN18.2 using IMAB362 aa primary antibody at 2 µg/ml on ice for 30 min and, upon washing in PBS/2% FCS, stained with PE-labelled anti-human Fcγ-specific IgG goat antibody (eBioscience) as secondary antibody for 30 min on ice. Upon further wash, resuspended stained cells in ice-cold FACS buffer were analyzed using a FACSCalibur™ instrument (see FIG. 1A), Un-transfected parental cells, not expressing CLDN18.2, were used as negative control. The expression of CLDN18.1 was analyzed in a similar fashion, using a proprietary pan-CLDN18 antibody recognizing CLDN18.1 and CLDN18.2. Any pan-CLDN18 antibody usable for flow cytometry measurement would also be adequate such as antibody anti Claudin-18/CLDN18 (C-term) provided by OriGene Technologies (catalog number AP50944PU-N), CLDN18 (C-Term) Rabbit pAb from MyBioSource (catalog number MBS8555451) or the CLDN18 Antibody from ProSci (catalog number 63-847).

The HEK293T cells stably expressing huCLDN18.1 and huCLDN18.2 were consequently used to test the binding specificity of the humanized antibodies hGBA-1, hGBA-2, hGBA-3, hGBA-4, hGBA-5, hGBA-6, hGBA-7, hGBA-8 and hGBA-9 to CLDN18.2 and not to huCLDN18.1. The cells were stained on ice for 30 min using the antibodies at 2 µg/ml and, upon washing in FACS buffer (PBS/2% FCS), stained with PE-labelled anti-human Fcγ-specific IgG goat antibody (eBioscience) as secondary antibody for 30 min on ice. Expression of CLDN18.1 in the HEK293T cells stably expressing huCLDN18.1 was verified with a pan-CLDN18 antibody (see FIG. 1, panel L) and expression of CLDN18.2 in the HEK293T cells stably expressing huCLDN18.2 was verified with the IMAB362 (see FIG. 1, panel A). FIG. 1 shows that all humanized antibodies bind specifically to huCLDN18.2 expressed by HEK293T cells, and not to huCLDN18.1. Furthermore, all humanized antibodies bind to huCLDN18.2 stronger than the parental antibody IMAB362.

Example 3: ELISA Binding Analysis of Humanized mAbs

The binding affinity to CLDN18.2 of the humanized antibodies (hGBA) was tested in an ELISA assay with lipoparticles bearing CLDN18.2 as source of antigen. CLDN18.2-lipoparticles and Null-lipoparticles (without antigen as a negative control) were used to coat 96-well plates at a final concentration of 10 U/ml. Upon washing with PBS/0.05% Tween™-20 (PBS-T) and blocking with PBS-T/3% BSA for at least 1 h at 37° C., 1:3 serial dilutions of hGBA and IMAB362 antibodies with a starting concentration of 2 µg/ml in PBS-T/1% BSA were added to the coated wells and incubated for at least 1 h at 37° C. The presence of bound antibodies was revealed through binding of an HRP-goat anti-human secondary antibody diluted in PBS-T/1% BSA, development with Sigma-Fast OPD as peroxidase substrate and the reaction was stopped by adding 2M $H_2SO_4$, followed by reading the OD at 490 nm on an ELISA plate reader. Representative binding curves are shown in FIG. 2. Surprisingly, the binding curves in FIG. 2 show that all humanized antibodies (hGBA-1 to hGBA-9) bind to CLDN18.2-lipoparticles with a higher affinity than IMAB362, shown by a higher maximal binding value.

Example 4: FC Titration on HEK293T and PA-TU-8988S High Cells

Figure 3A:
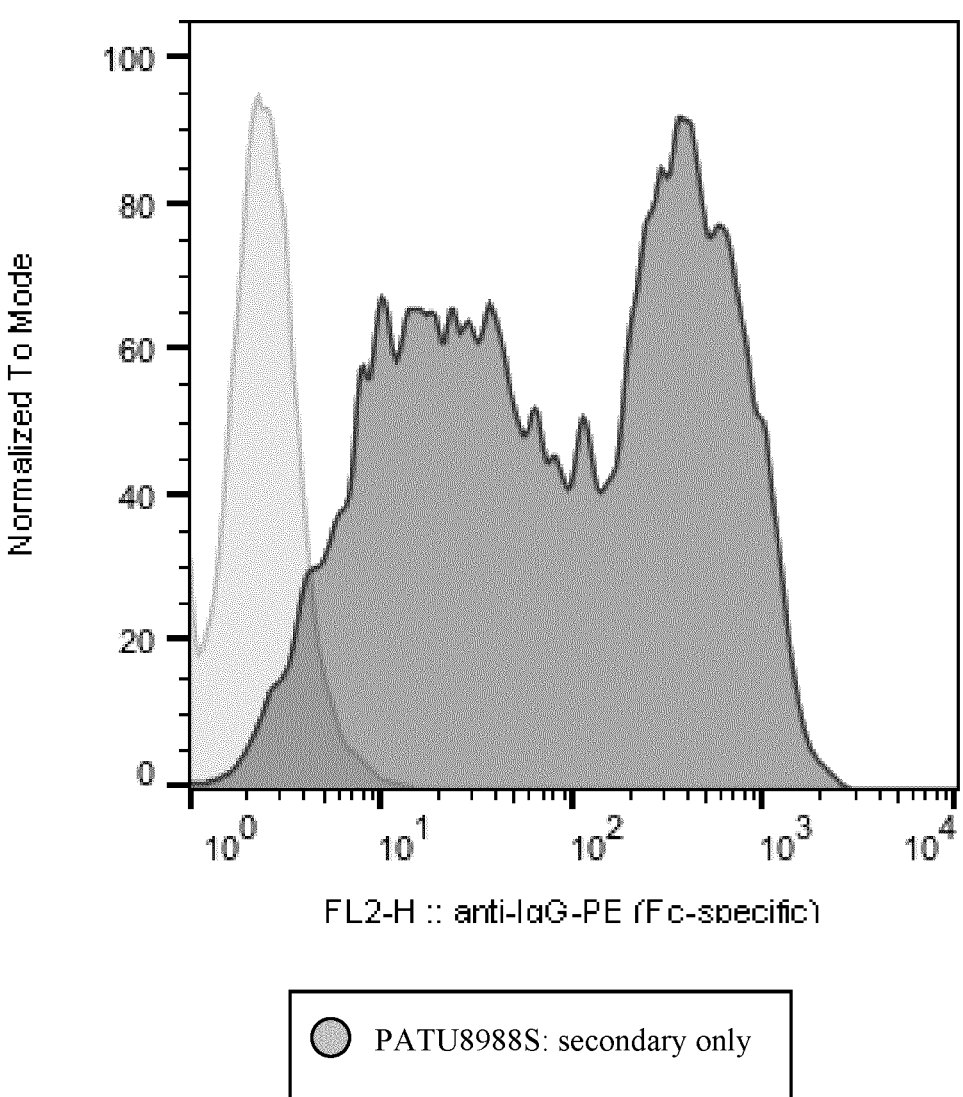
FIG. 3: Sorting of PA-TU-8988S cells for expression levels of CLDN18.2. 3A: FACS profile of PA-TU-9888S stained with IMAB362. 3B: FACS profile of PA-TU-8988S cells sorted by FACS for medium and high expression of CLDN18.2.
Figure 3B:
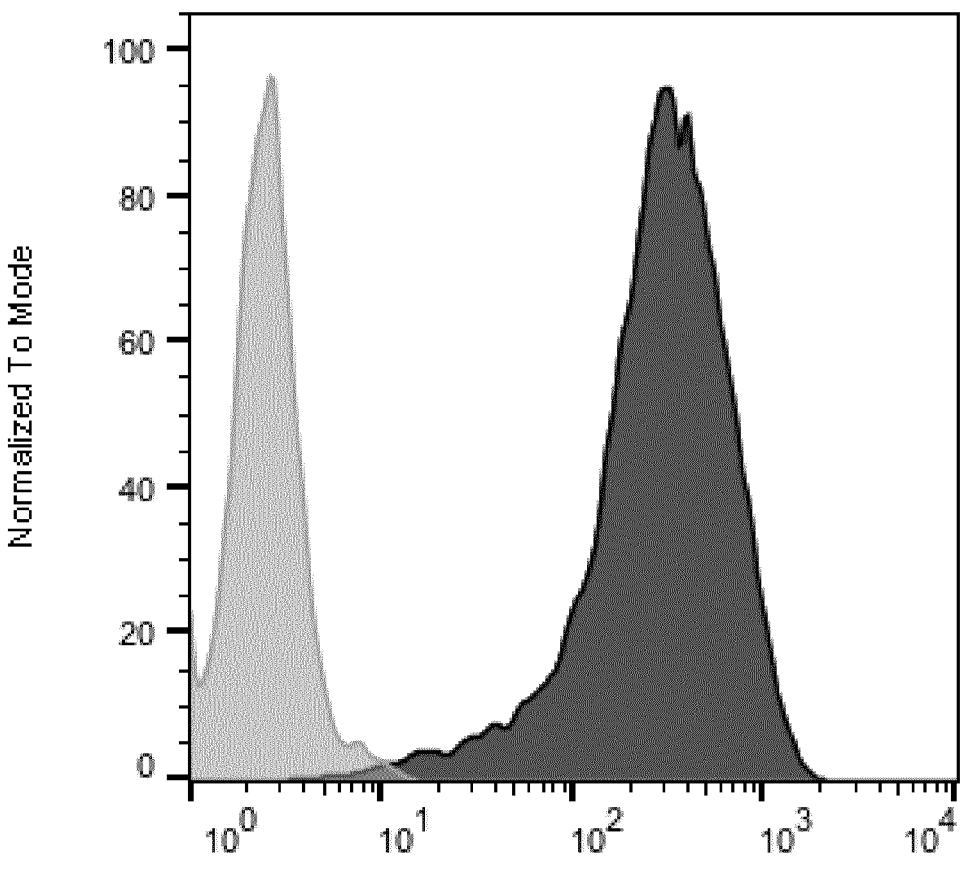
Figure 4A:
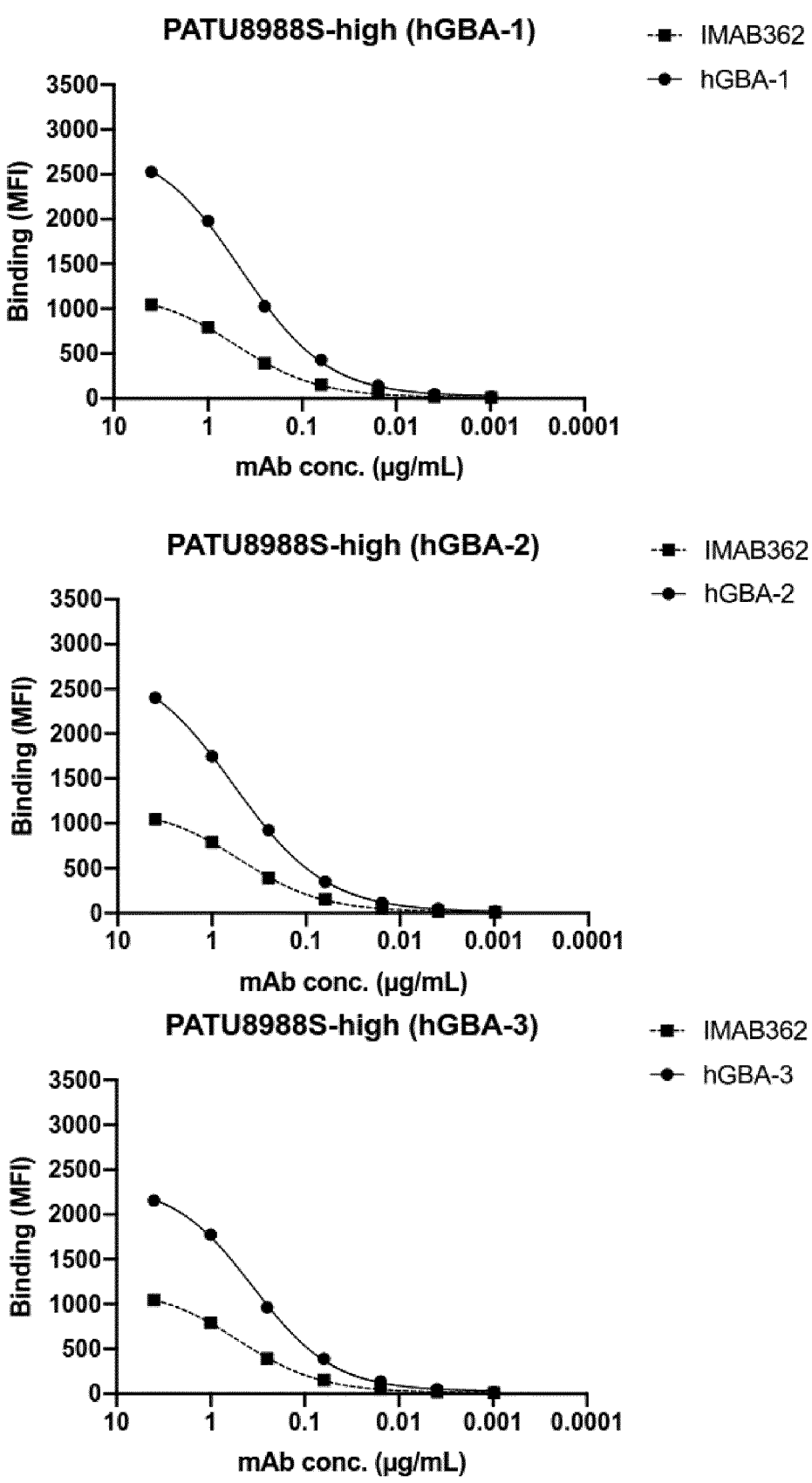
FIG. 4: FC titration assay on PA-TU-8988S-High cells (4A-D) and HEK-293T expressing huCLDN18.2 (4E-H).
Figure 4B:
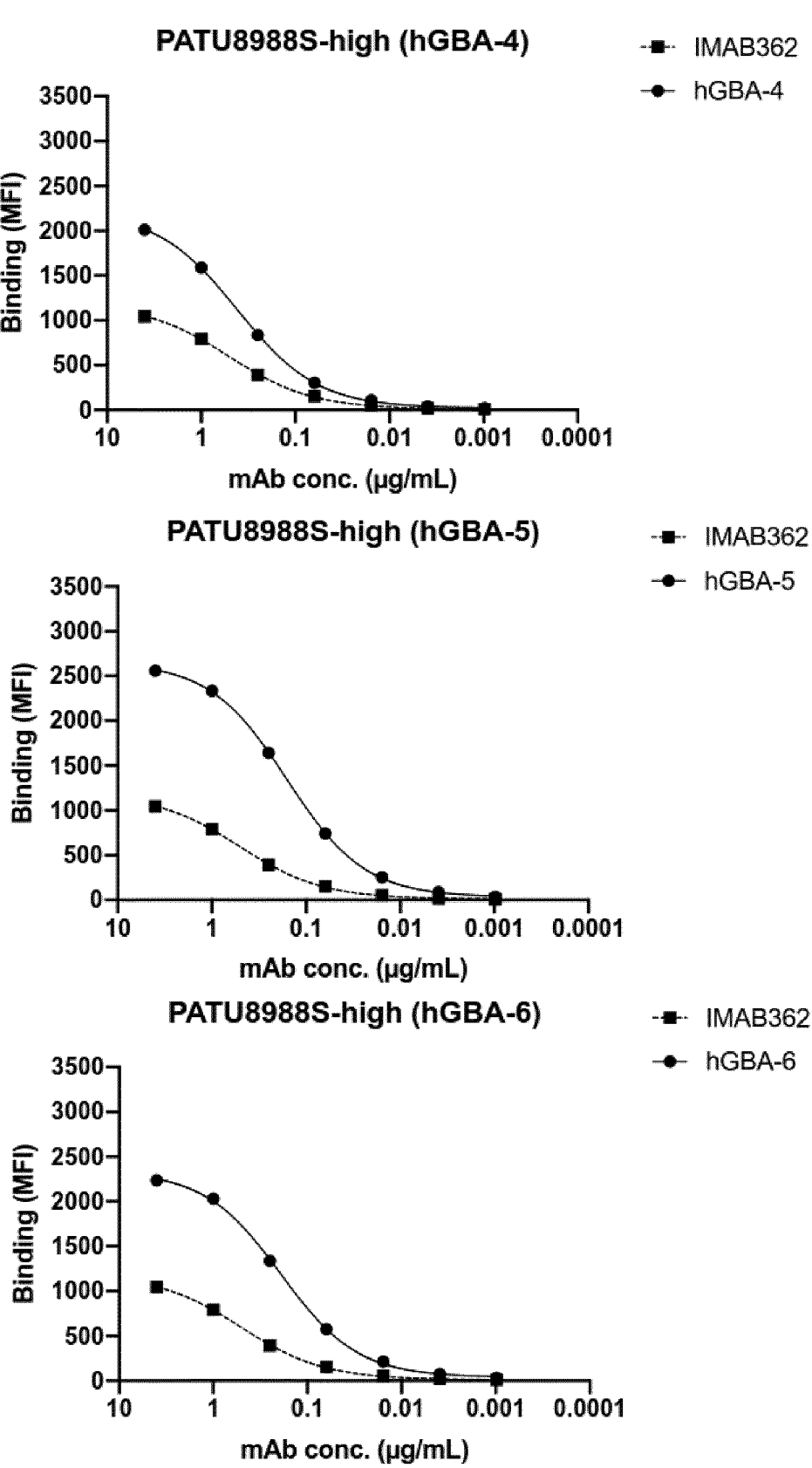
Figure 4C:
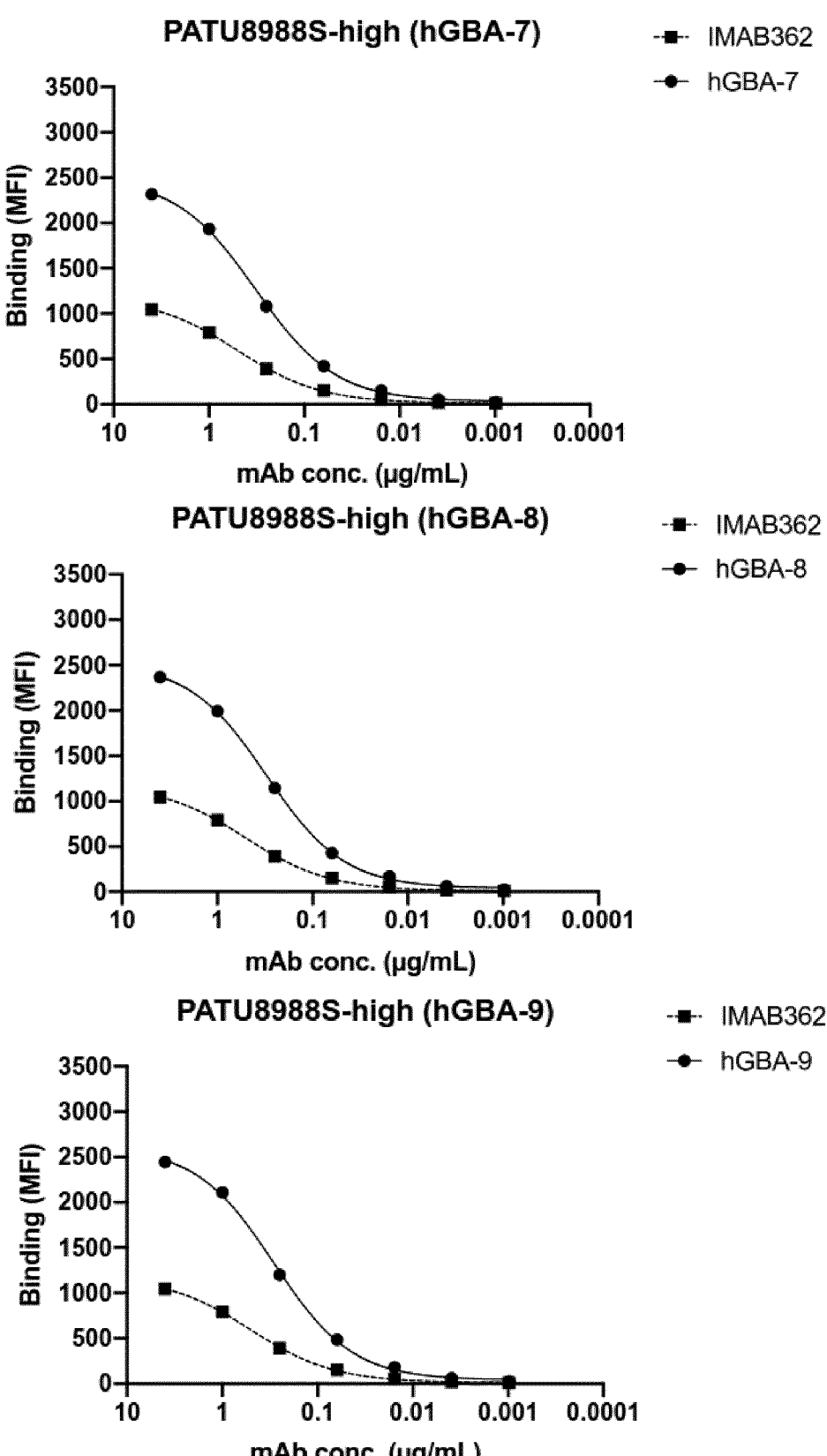
Figure 4D:
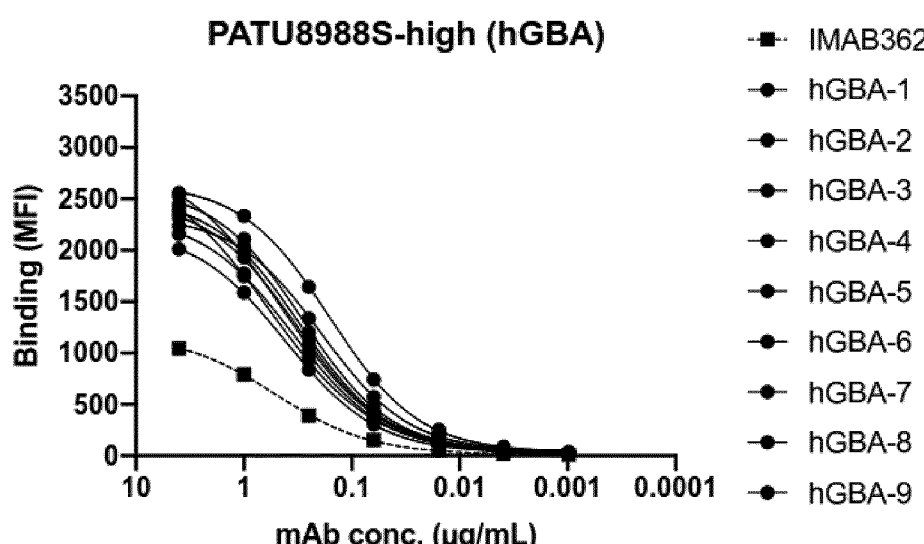
Figure 4E:
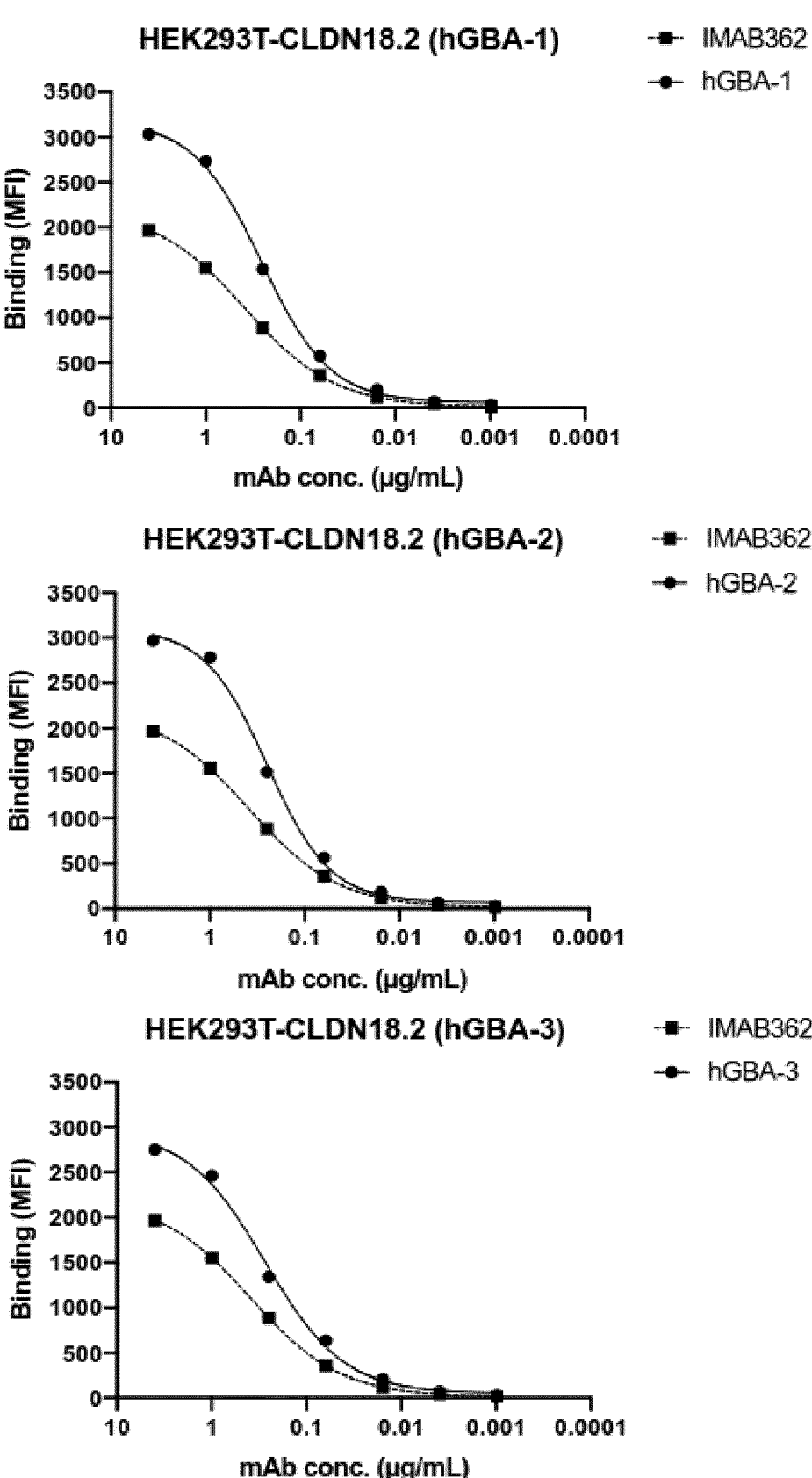
Figure 4F:
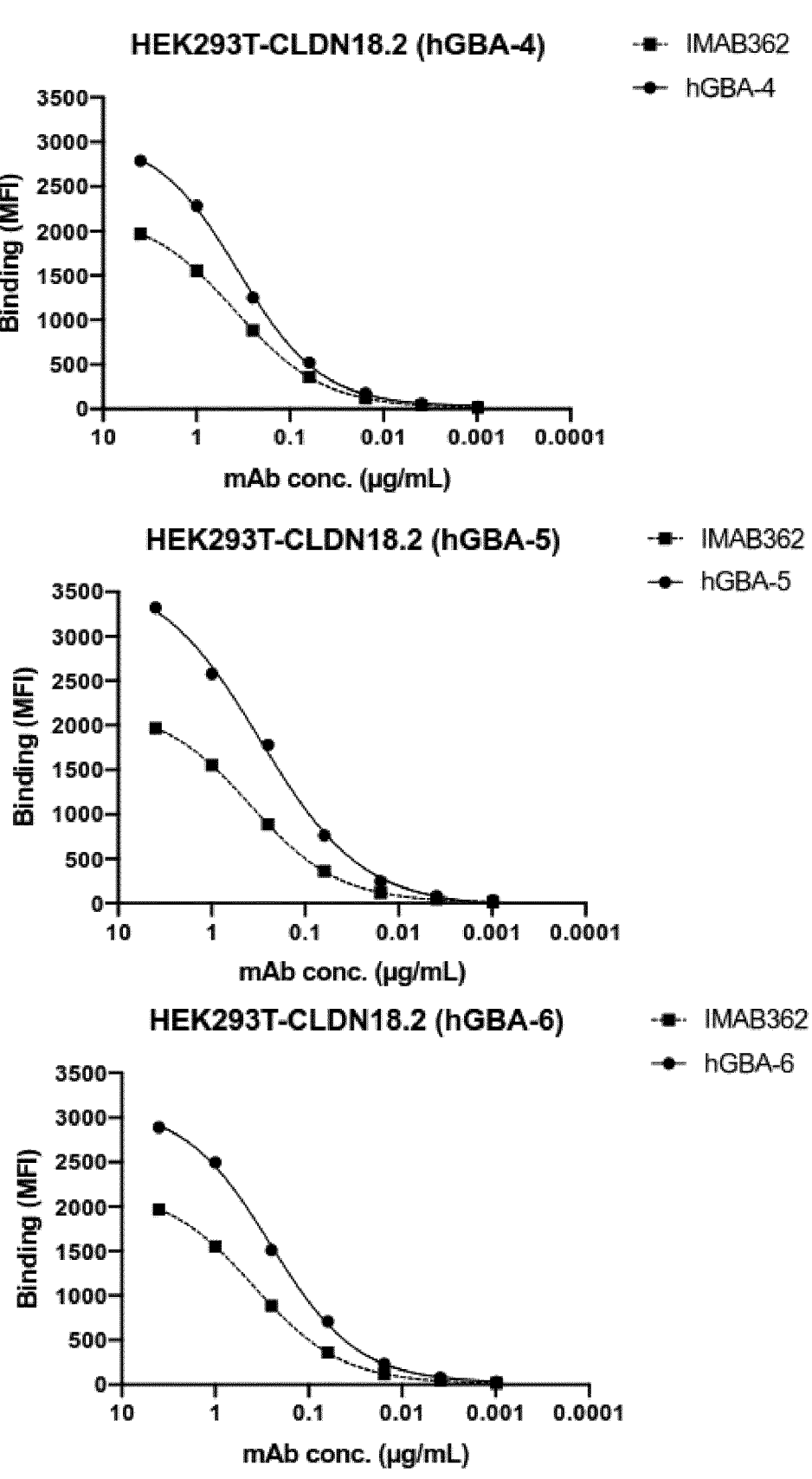
Figure 4G:
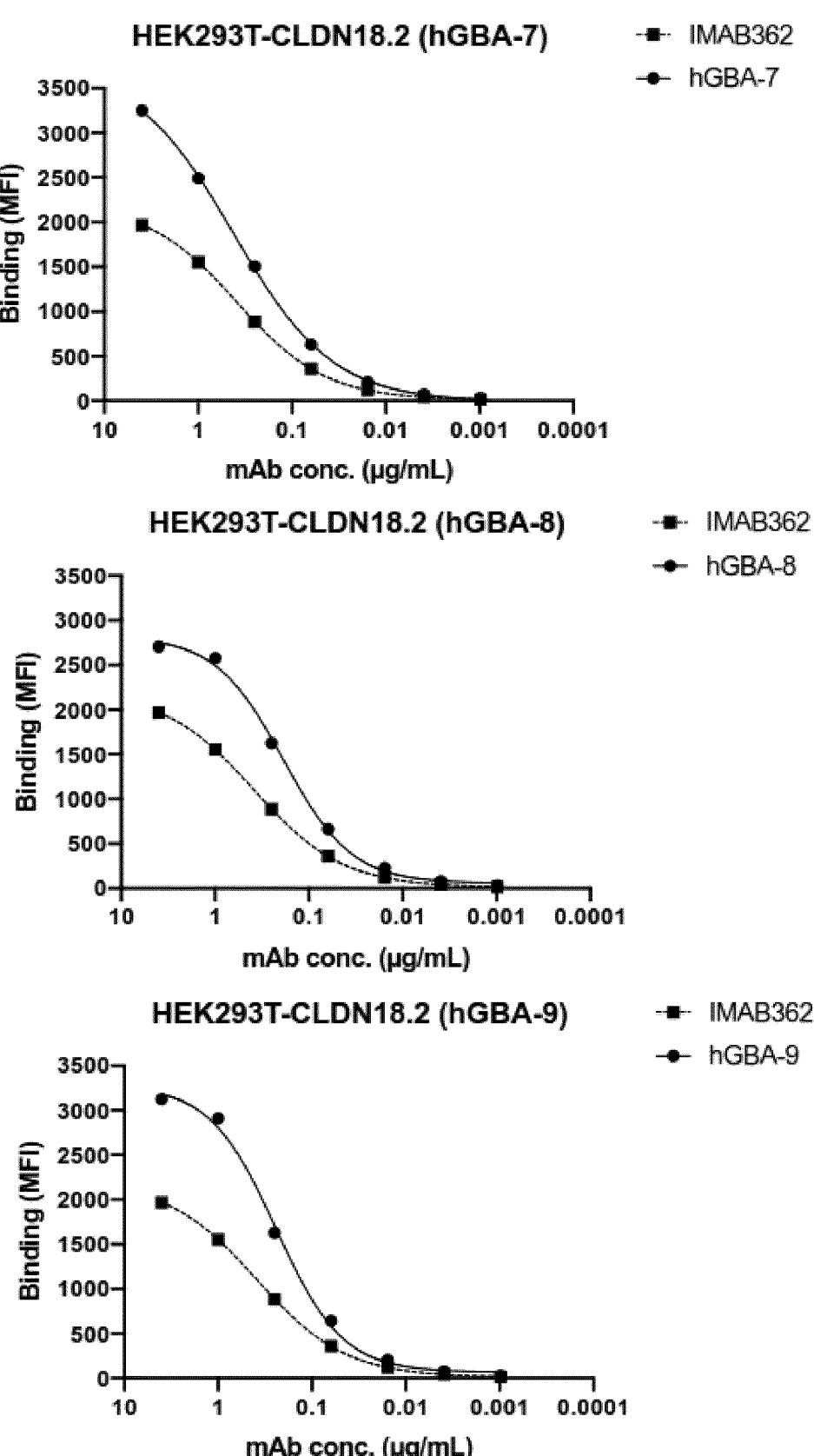
Figure 4H:
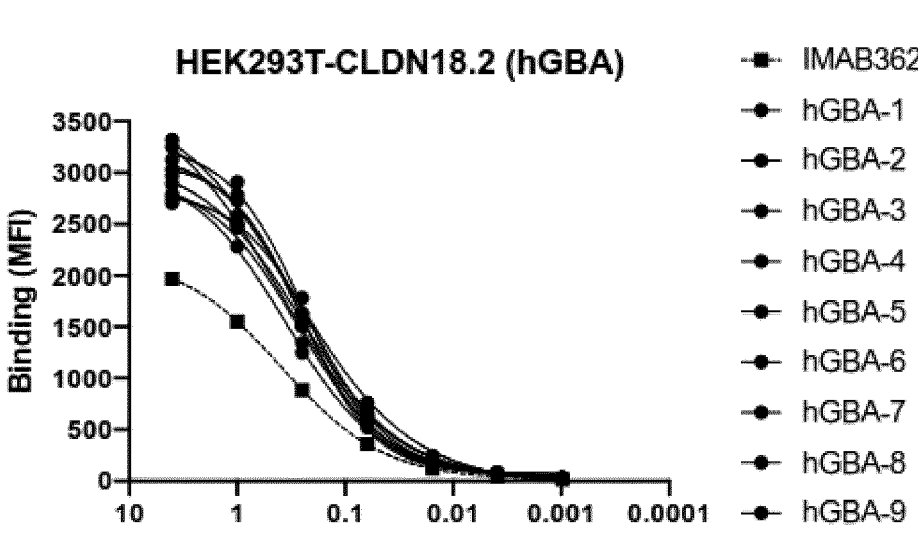

PA-TU-8988S cells (Creative Bioarray, catalog number CSC-00326) expressing high levels of CLDN18.2 were selected by FACS. Herein, these cells are designated as PA-TU-8988S-High cells. Based on FACS staining with IMAB362, the PA-TU-8988S cell population expresses different levels of CLDN18.2, with a high and a medium level of expression (see FIG. 3A). In order to have a more homogenous cell population, the cells were sorted by FACS to select only cells with a higher CLDN18.2 expression. In brief, PA-TU-8988S cells suspended in FACS buffer (PBS, 2% FCS) were incubated on ice for 30 min with IMAB362 at 2 μg/ml. After wash in FACS buffer, the cells were incubated with the PE-labeled Fcγ specific IgG goat anti-human secondary antibody (eBioscience) on ice for 30 min. After wash, the stained cells were resuspended in FACS buffer, analyzed and sorted by a FACSAria™ instrument, separating medium expressing cells (FIG. 3B) from high expressing cells (FIG. 3B). After sorting, the collected PA-TU-8988S-High cells were resuspended in growth media, expanded in growth media and frozen aliquots were preserved in liquid N$_2$.

In order to quantify the affinity of the antibodies to CLDN18.2, $250 \times 10^3$ cells/well of HEK293T cells overexpressing CLDN18.2 or PA-TU-8988S-High cells were seeded in FC buffer (PBS/2% FCS) into 96-well plates and allowed to settle by centrifugation. IMAB362 and hGBA antibodies to be tested were diluted at 4 μg/ml, followed by 1:4 serial dilutions and incubated with the platted cells for 30 min at 4° C. A PE-coupled secondary anti-human IgG antibody was added to the cells for additional 30 min at 4° C. after washes with the FACS buffer, followed by further washes with FC buffer. The cells were then resuspended in 100 μl FC buffer and measured with a FACSCalibur™ cell analyzer (BD Biosciences, USA). The FC analysis (see FIG. 4 and Table 4) shows that all hGBA antibodies have a stronger binding affinity to CLDN18.2 (reflected by a higher Max MFI for all tested new antibodies, see Table 4) than IMAB362, in both cell lines. The binding affinity of all hGBA antibodies is similar between each other but is significantly higher than the parental antibody IMAB362.

TABLE 4

Maximum MFI and EC50 (μg/ml) measured on all the hGBA and IMAB362 antibodies on the HEK293T cells lines overexpressing CLDN18.2 and on the PA-TU-8988S-High cell lines.

| | HEK293T-CLDN18.2 | | PA-TU-8988S-High | |
| Antibody | Max MFI EXP. 2 | EC50 (μg/ml) EXP. 2 | Max MFI EXP. 2 | EC50 (μg/ml) EXP. 2 |
| --- | --- | --- | --- | --- |
| IMAB362 | 1968 | 0.3878 | 1046 | 0.5082 |
| hGBA1 | 3031 | 0.2586 | 2527 | 0.4439 |
| hGBA2 | 2967 | 0.2486 | 2403 | 0.5836 |
| hGBA3 | 2750 | 0.2734 | 2156 | 0.3525 |
| hGBA4 | 2790 | 0.3575 | 2011 | 0.4123 |
| hGBA5 | 3321 | 0.3052 | 2560 | 0.1593 |
| hGBA6 | 2888 | 0.2567 | 2236 | 0.1913 |
| hGBA7 | 3250 | 0.4196 | 2318 | 0.3232 |
| hGBA8 | 2704 | 0.187 | 2366 | 0.3034 |
| hGBA9 | 3124 | 0.2414 | 2445 | 0.286 |

The invention is also described by the following embodiments:

1. An antibody or fragment thereof binding to CLDN18.2, which comprises:
   HCDR1, HCDR2 and HCR3 sequences of SEQ ID NO: 1, SEQ ID NO: 2 and SEQ ID NO: 3, respectively and LCDR1, LCDR2 and LCDR3 sequences of SEQ ID NO: 4, SEQ ID NO: 5 and SEQ ID NO: 6, respectively.

2. The antibody or fragment thereof of embodiment 1, comprising:
   a. the HCDR1, HCDR2 and HCDR3 sequences of SEQ ID NO: 7, SEQ ID NO: 9 and SEQ ID NO: 18, respectively and
      the LCDR1, LCDR2 and LCDR3 sequences of SEQ ID NO: 25, SEQ ID NO: 5 and SEQ ID NO: 29, respectively;
   b. the HCDR1, HCDR2 and HCDR3 sequences of SEQ ID NO: 7, SEQ ID NO: 10 and SEQ ID NO: 19, respectively and
      the LCDR1, LCDR2 and LCDR3 sequences of SEQ ID NO: 25, SEQ ID NO: 5 and SEQ ID NO: 29, respectively;
   c. the HCDR1, HCDR2 and HCDR3 sequences of SEQ ID NO: 7, SEQ ID NO: 10 and SEQ ID NO: 20, respectively and
      the LCDR1, LCDR2 and LCDR3 sequences of SEQ ID NO: 25, SEQ ID NO: 5 and SEQ ID NO: 30, respectively;
   d. the HCDR1, HCDR2 and HCDR3 sequences of SEQ ID NO: 7, SEQ ID NO: 12 and SEQ ID NO: 21, respectively and
      the LCDR1, LCDR2 and LCDR3 sequences of SEQ ID NO: 26, SEQ ID NO: 5 and SEQ ID NO: 30, respectively;
   e. the HCDR1, HCDR2 and HCDR3 sequences of SEQ ID NO: 7, SEQ ID NO: 13 and SEQ ID NO: 18, respectively and
      the LCDR1, LCDR2 and LCDR3 sequences of SEQ ID NO: 25, SEQ ID NO: 5 and SEQ ID NO: 31, respectively;
   f. the HCDR1, HCDR2 and HCDR3 sequences of SEQ ID NO: 8, SEQ ID NO: 14 and SEQ ID NO: 22, respectively and
      the LCDR1, LCDR2 and LCDR3 sequences of SEQ ID NO: 25, SEQ ID NO: 5 and SEQ ID NO: 29, respectively;
   g. the HCDR1, HCDR2 and HCDR3 sequences of SEQ ID NO: 7, SEQ ID NO: 15 and SEQ ID NO: 23, respectively and
      the LCDR1, LCDR2 and LCDR3 sequences of SEQ ID NO: 27, SEQ ID NO: 5 and SEQ ID NO: 29, respectively;
   h. the HCDR1, HCDR2 and HCDR3 sequences of SEQ ID NO: 7, SEQ ID NO: 16 and SEQ ID NO: 23, respectively and
      the LCDR1, LCDR2 and LCDR3 sequences of SEQ ID NO: 25, SEQ ID NO: 5 and SEQ ID NO: 29, respectively; or
   i. the HCDR1, HCDR2 and HCDR3 sequences of SEQ ID NO: 8, SEQ ID NO: 17 and SEQ ID NO: 24, respectively and
      the LCDR1, LCDR2 and LCDR3 sequences of SEQ ID NO: 28, SEQ ID NO: 5 and SEQ ID NO: 31, respectively.

3. The antibody or fragment thereof of embodiments 1 and 2, comprising:
   a. a VH sequence having at least 80%, at least 85%, at least 90%, at least 95% or at least 98% sequence identity with the amino acid sequence of SEQ ID NO: 32;
   b. a VH sequence having at least 80%, at least 85%, at least 90%, at least 95% or at least 98% sequence identity with the amino acid sequence of SEQ ID NO: 34;
   c. a VH sequence having at least 80%, at least 85%, at least 90%, at least 95% or at least 98% sequence identity with the amino acid sequence of SEQ ID NO: 35;
   d. a VH sequence having at least 80%, at least 85%, at least 90%, at least 95% or at least 98% sequence identity with the amino acid sequence of SEQ ID NO: 37;
   e. a VH sequence having at least 80%, at least 85%, at least 90%, at least 95% or at least 98% sequence identity with the amino acid sequence of SEQ ID NO: 39;
   f. a VH sequence having at least 80%, at least 85%, at least 90%, at least 95% or at least 98% sequence identity with the amino acid sequence of SEQ ID NO: 41;
   g. a VH sequence having at least 80%, at least 85%, at least 90%, at least 95% or at least 98% sequence identity with the amino acid sequence of SEQ ID NO: 42;
   h. a VH sequence having at least 80%, at least 85%, at least 90%, at least 95% or at least 98% sequence identity with the amino acid sequence of SEQ ID NO: 44 or
   i. a VH sequence having at least 80%, at least 85%, at least 90%, at least 95% or at least 98% sequence identity with the amino acid sequence of SEQ ID NO: 45;
   and
   j. a VL sequence having at least 80%, at least 85%, at least 90%, at least 95% or at least 98% sequence identity with the amino acid sequence of SEQ ID NO: 33;
   k. a VL sequence having at least 80%, at least 85%, at least 90%, at least 95% or at least 98% sequence identity with the amino acid sequence of SEQ ID NO: 36;
   l. a VL sequence having at least 80%, at least 85%, at least 90%, at least 95% or at least 98% sequence identity with the amino acid sequence of SEQ ID NO: 38;
   m. a VL sequence having at least 80%, at least 85%, at least 90%, at least 95% or at least 98% sequence identity with the amino acid sequence of SEQ ID NO: 40;
   n. a VL sequence having at least 80%, at least 85%, at least 90%, at least 95% or at least 98% sequence identity with the amino acid sequence of SEQ ID NO: 43; or
   o. a VL sequence having at least 80%, at least 85%, at least 90%, at least 95% or at least 98% sequence identity with the amino acid sequence of SEQ ID NO: 46.

4. The antibody or fragment thereof of any one of embodiments 1 to 3, comprising:
   a. a VH sequence of SEQ ID NO: 32;
   b. a VH sequence of SEQ ID NO: 34;
   c. a VH sequence of SEQ ID NO: 35;
   d. a VH sequence of SEQ ID NO: 37;

e. a VH sequence of SEQ ID NO: 39;

f. a VH sequence of SEQ ID NO: 41;

g. a VH sequence of SEQ ID NO: 42;

h. a VH sequence of SEQ ID NO: 44; or i. a VH sequence of SEQ ID NO: 45;

and j. a VL sequence of SEQ ID NO: 33;

k. a VL sequence of SEQ ID NO: 36;

l. a VL sequence of SEQ ID NO: 38;

m. a VL sequence of SEQ ID NO: 40;

n. a VL sequence of SEQ ID NO: 43; or o. a VL sequence of SEQ ID NO: 46.

5. The antibody or fragment thereof of any one of embodiments 1 to 4, comprising:

a. a VH sequence of SEQ ID NO: 32 and a VL sequence of SEQ ID NO: 33;

b. a VH sequence of SEQ ID NO: 34 and a VL sequence of SEQ ID NO: 33;

c. a VH sequence of SEQ ID NO: 35 and a VL sequence of SEQ ID NO: 36;

d. a VH sequence of SEQ ID NO: 37 and a VL sequence of SEQ ID NO: 38;

e. a VH sequence of SEQ ID NO: 39 and a VL sequence of SEQ ID NO: 40;

f. a VH sequence of SEQ ID NO: 41 and a VL sequence of SEQ ID NO: 33;

g. a VH sequence of SEQ ID NO: 42 and a VL sequence of SEQ ID NO: 43;

h. a VH sequence of SEQ ID NO: 44 and a VL sequence of SEQ ID NO: 33; or i. a VH sequence of SEQ ID NO: 45 and a VL sequence of SEQ ID NO: 46.

6. The antibody or fragment thereof of any one of embodiments 1 to 5, consisting of:

a. a heavy chain sequence having at least 80%, at least 85%, at least 90%, at least 95% or at least 98% sequence identity with the amino acid sequence of SEQ ID NO: 49 and a light chain sequence having at least 80%, at least 85%, at least 90%, at least 95% or at least 98% sequence identity with the amino acid sequence of SEQ ID NO: 50;

b. a heavy chain sequence having at least 80%, at least 85%, at least 90%, at least 95% or at least 98% sequence identity with the amino acid sequence of SEQ ID NO: 51 and a light chain sequence having at least 80%, at least 85%, at least 90%, at least 95% or at least 98% sequence identity with the amino acid sequence of SEQ ID NO: 50;

c. a heavy chain sequence having at least 80%, at least 85%, at least 90%, at least 95% or at least 98% sequence identity with the amino acid sequence of SEQ ID NO: 52 and a light chain sequence having at least 80%, at least 85%, at least 90%, at least 95% or at least 98% sequence identity with the amino acid sequence of SEQ ID NO: 53;

d. a heavy chain sequence having at least 80%, at least 85%, at least 90%, at least 95% or at least 98% sequence identity with the amino acid sequence of SEQ ID NO: 54 and a light chain sequence having at least 80%, at least 85%, at least 90%, at least 95% or at least 98% sequence identity with the amino acid sequence of SEQ ID NO: 55;

e. a heavy chain sequence having at least 80%, at least 85%, at least 90%, at least 95% or at least 98% sequence identity with the amino acid sequence of SEQ ID NO: 56 and a light chain sequence having at least 80%, at least 85%, at least 90%, at least 95% or at least 98% sequence identity with the amino acid sequence of SEQ ID NO: 57;

f. a heavy chain sequence having at least 80%, at least 85%, at least 90%, at least 95% or at least 98% sequence identity with the amino acid sequence of SEQ ID NO: 58 and a light chain sequence having at least 80%, at least 85%, at least 90%, at least 95% or at least 98% sequence identity with the amino acid sequence of SEQ ID NO: 50;

g. a heavy chain sequence having at least 80%, at least 85%, at least 90%, at least 95% or at least 98% sequence identity with the amino acid sequence of SEQ ID NO: 59 and a light chain sequence having at least 80%, at least 85%, at least 90%, at least 95% or at least 98% sequence identity with the amino acid sequence of SEQ ID NO: 60;

h. a heavy chain sequence having at least 80%, at least 85%, at least 90%, at least 95% or at least 98% sequence identity with the amino acid sequence of SEQ ID NO: 61 and a light chain sequence having at least 80%, at least 85%, at least 90%, at least 95% or at least 98% sequence identity with the amino acid sequence of SEQ ID NO: 50; or i. a heavy chain sequence having at least 80%, at least 85%, at least 90%, at least 95% or at least 98% sequence identity with the amino acid sequence of SEQ ID NO: 62 and a light chain sequence having at least 80%, at least 85%, at least 90%, at least 95% or at least 98% sequence identity with the amino acid sequence of SEQ ID NO: 63.

7. The antibody or fragment thereof of any one of embodiments 1 to 6, consisting of:

a. the heavy chain sequence of SEQ ID NO: 49 and light chain sequence of SEQ ID NO: 50;

b. the heavy chain sequence of SEQ ID NO: 51 and light chain sequence of SEQ ID NO: 50;

c. the heavy chain sequence of SEQ ID NO: 52 and light chain sequence of SEQ ID NO: 53;

d. the heavy chain sequence of SEQ ID NO: 54 and light chain sequence of SEQ ID NO: 55;

e. the heavy chain sequence of SEQ ID NO: 56 and light chain sequence of SEQ ID NO: 57;

f. the heavy chain sequence of SEQ ID NO: 58 and light chain sequence of SEQ ID NO: 50;

g. the heavy chain sequence of SEQ ID NO: 59 and light chain sequence of SEQ ID NO: 60;

h. the heavy chain sequence of SEQ ID NO: 61 and light chain sequence of SEQ ID NO: 50; or i. the heavy chain sequence of SEQ ID NO: 62 and light chain sequence of SEQ ID NO: 63.

8. An antibody or fragment thereof that competes for binding with an antibody or fragment thereof of any one of embodiments 1 to 7.

9. The antibody or fragment thereof of any one of embodiments 1 to 8, wherein the format of the antibody or fragment thereof is selected from the group consisting of IgA1, IgA2, IgD, IgE, IgG1, IgG2, IgG3, IgG4, synthetic IgG, IgM, F(ab)$_2$, Fv, scFv, IgGACH2, F(ab')$_2$, scFvCH3, Fab, VL, VH, scFv4, scFv3, scFv2, dsFv, Fv, scFv-Fc, (scFv)$_2$, a non-depleting IgG, a diabody, and a bivalent antibody, or Fc-engineered versions thereof.

10. The antibody or fragment thereof of any one of embodiments 1 to 9, wherein the antibody or fragment thereof is humanized.

11. The antibody or fragment thereof of any one of embodiments 1 to 10, wherein the antibody or fragment thereof is isolated.

12. The antibody or fragment thereof of any one of embodiments 1 to 11, wherein the antibody or fragment thereof does not bind to CLDN18.1.

13. The antibody or fragment thereof of any one of embodiments 1 to 12, wherein the antibody or fragment thereof exhibits increased binding to CLDN18.2 as compared to antibody IMAB362.

14. The antibody or fragment of embodiment 13 wherein increased binding is measured as EC50 value and/or maxMFI value by flow cytometry titration on cells expressing CLDN18.2, preferably wherein the cells are HEK293T cells or PA-TU-8988-High cells.

15. The antibody or fragment of embodiment 14, wherein the measured EC50 value of the antibody is at least 10% lower, at least 20% lower, at least 40% lower, at least 50% lower or at least 75% lower than the EC50 value of antibody IMAB362.

16. The antibody or fragment of embodiment 14, wherein the measured maxMFI value of the antibody is at least 10% higher, at least 20% higher, at least 40% higher, at least 50% higher or at least 75% higher than the maxMFI value of antibody IMAB362.

17. A nucleic acid encoding the antibody or fragment thereof of any of embodiments 1 to 16.

18. A vector comprising the nucleic acid of embodiment 17.

19. A host cell comprising the nucleic acid of embodiment 17 or a vector of embodiment 18.

20. The antibody or fragment thereof of any one of embodiments 1 to 16, the nucleic acid of embodiment 17, the vector of embodiment 18 or the host cell of embodiment 19 for use in the treatment of a subject
    a. suffering from,
    b. at risk of developing, and/or
    c. being diagnosed for
    a neoplastic disease.

21. The antibody or fragment thereof for the use of embodiment 20, wherein the neoplastic disease is selected from the group consisting of pancreatic, gastric, esophageal, ovarian and lung cancer.

---

SEQUENCES

SEQ ID NO: 1 GYXFTSYWIG X in $3^{rd}$ position is T or S

SEQ ID NO: 2
GXIYPXXXXTXYX X in $2^{nd}$ position is N or I; X in $6^{th}$ position is S or G; X in $7^{th}$ position is A, E or D; X in $8^{th}$ position is A or S; X in $9^{th}$ position is Y or D; X in $11^{th}$ position is N or R; X in last position is A or S SEQ ID NO: 3
XRXWRGNSFDX X in 1st position is A or T; X in 3rd position is L, M, I or Q; X in last last position is A or Y SEQ ID NO: 4
KSSQSXLNSGNQKNYLX X in 6th position is L or V; X in last position is T or A

SEQ ID NO: 5
WASTRES

SEQ ID NO: 6
QXDYSYPXT X in 2nd position is N or Q; X in L or F

SEQ ID NO: 7
GYSFTSYWIG

SEQ ID NO: 8
GYTFTSYWIG

SEQ ID NO: 9
GNIYPGASDTRYA

SEQ ID NO: 10
GNIYPGDADTRYA

SEQ ID NO: 11
GIIYPGASDTNYA

SEQ ID NO: 12
GIIYPGDAYTRYS

SEQ ID NO: 13
GIIYPGAAYTRYA

SEQ ID NO: 14
GNIYPGASYTRYS

SEQ ID NO: 15
GNIYPGEAYTRYS

SEQ ID NO: 16
GNIYPSESYTNYA

| SEQUENCES |
| --- |

SEQ ID NO: 17
GIIYPSAAYTRYA

SEQ ID NO: 18
ARLWRGNSFDY

SEQ ID NO: 19
ARMWRGNSFDY

SEQ ID NO: 20
ARIWRGNSFDY

SEQ ID NO: 21
TRLWRGNSFDA

SEQ ID NO: 22
TRQWRGNSFDY

SEQ ID NO: 23
TRLWRGNSFDY

SEQ ID NO: 24
TRMWRGNSFDY

SEQ ID NO: 25
KSSQSLLNSGNQKNYLA

SEQ ID NO: 26
KSSQSLLNSGNQKNYLT

SEQ ID NO: 27
KSSQSVLNSGNQKNYLT

SEQ ID NO: 28
KSSQSVLNSGNQKNYLA

SEQ ID NO: 29
QNDYSYPFT

SEQ ID NO: 30
QNDYSYPLT

SEQ ID NO: 31
QQDYSYPFT

SEQ ID NO: 21 hGBA-1 HC variable region
EVQLVQSGAEVKKPGESLKISCKGSGYSFTSYWIGWVRQMPGKGLEWMGNIYPGASDTRYAPSFQGQVTISADKSISTAYLQWSSLKAS
DTAMYYCARLWRGNSFDYWGQGTLVTVSS SEQ ID NO: 33 hGBA-1, hGBA-2, hGBA-6 , hGBA-8 LC variable region
DIVMTQSPDSLAVSLGERATINCKSSQSLLNSGNQKNYLAWYQQKPGQPPKLLIYWASTRESGVPDRFSGSGSGTDFTLTISSLQAEDV
AVYYCQNDYSYPFTFGQGTKVEIK SEQ ID NO: 34 hGBA-2 HC variable region
EVQLVQSGAEVKKPGESLKISCKGSGYSFTSYWIGWVRQMPGKGLEWMGNIYPGDADTRYAPSFQGQVTISADKSISTAYLQWSSLKAS
DTAMYYCARMWRGNSFDYWGQGTLVTVSS SEQ ID NO: 35 hGBA-3 HC variable region
EVQLVQSGAEVKKPGESLKISCKGSGYSFTSYWIGWVRQMPGKGLEWMGIIYPGASDTNYAPSFQGQVTISADKSISTAYLQWSSLKAS
DTAMYYCARIWRGNSFDYWGQGTLVTVSS SEQ ID NO: 36 hGBA-3 LC variable region
DIVMTQSPDSLAVSLGERATINCKSSQSLLNSGNQKNYLAWYQQKPGQPPKLLIYWASTRESGVPDRFSGSGSGTDFTLTISSLQAEDV
AVYYCQNDYSYPLTFGQGTKVEIK SEQ ID NO: 37 hGBA-4 HC variable region
EVQLVQSGAEVKKPGESLKISCKGSGYSFTSYWIGWVRQMPGKGLEWMGIIYPGDAYTRYSPSFQGQVTISADKSISTAYLQWSSLKAS
DTAMYYCTRLWRGNSFDAWGQGTLVTVSS SEQ ID NO: 38 hGBA-4 LC variable region
DIVMTQSPDSLAVSLGERATINCKSSQSLLNSGNQKNYLTWYQQKPGQPPKLLIYWASTRESGVPDRFSGSGSGTDFTLTISSLQAEDV
AVYYCQNDYSYPLTFGQGTKVEIK SEQ ID NO: 39 hGBA-5 HC variable region
EVQLVQSGAEVKKPGESLKISCKGSGYSFTSYWIGWVRQMPGKGLEWMGIIYPGAAYTRYAPSFQGQVTISADKSISTAYLQWSSLKAS
DTAMYYCARLWRGNSFDYWGQGTLVTVSS

SEQUENCES

SEQ ID NO: 40 hGBA-5 LC variable region
DIVMTQSPDSLAVSLGERATINCKSSQSLLNSGNQKNYLAWYQQKPGQPPKLLIYWASTRESGVPDRFSGSGSGTDFTLTISSLQAEDV
AVYYCQQDYSYPFTFGQGTKVEIK SEQ ID NO: 41 hGBA-6 HC variable region
EVQLVQSGAEVKKPGESLKISCKGSGYTFTSYWIGWVRQMPGKGLEWMGNIYPGASYTRYSPSFQGQVTISADKSISTAYLQWSSLKAS
DTAMYYCTRQWRGNSFDYWGQGTLVTVSS SEQ ID NO: 42 hGBA-7 HC variable region
EVQLVQSGAEVKKPGESLKISCKGSGYSFTSYWIGWVRQMPGKGLEWMGNIYPGEAYTRYSPSFQGQVTISADKSISTAYLQWSSLKAS
DTAMYYCTRLWRGNSFDYWGQGTLVTVSS SEQ ID NO: 43 hGBA-7 LC variable region
DIVMTQSPDSLAVSLGERATINCKSSQSVLNSGNQKNYLTWYQQKPGQPPKLLIYWASTRESGVPDRFSGSGSGTDFTLTISSLQAEDV
AVYYCQNDYSYPFTFGQGTKVEIK SEQ ID NO: 44 hGBA-8 HC variable region
EVQLVQSGAEVKKPGESLKISCKGSGYSFTSYWIGWVRQMPGKGLEWMGNIYPSESYTNYAPSFQGQVTISADKSISTAYLQWSSLKAS
DTAMYYCTRLWRGNSFDYWGQGTLVTVSS SEQ ID NO: 45 hGBA-9 HC variable region
EVQLVQSGAEVKKPGESLKISCKGSGYTFTSYWIGWVRQMPGKGLEWMGIIYPSAAYTRYAPSFQGQVTISADKSISTAYLQWSSLKAS
DTAMYYCTRMWRGNSFDYWGQGTLVTVSS SEQ ID NO: 46 hGBA-9LC variable region
DIVMTQSPDSLAVSLGERATINCKSSQSVLNSGNQKNYLAWYQQKPGQPPKLLIYWASTRESGVPDRFSGSGSGTDFTLTISSLQAEDV
AVYYCQQDYSYPFTFGQGTKVEIK SEQ ID NO: 47 IMAB362 HC full
QVQLQQPGAELVRPGASVKLSCKASGYTFTSYWINWVKQRPGQGLEWIGNIYPSDSYTNYNQKFKDKATLTVDKSSSTAYMQLSSPTSE
DSAVYYCTRSWRGNSFDYWGQGTTLTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFLYSKLTVDKSRWQQGNVFSCSVMHEALHNHYTQKSLSLS
PGK SEQ ID NO: 48 IMAB362 LC full
DIVMTQSPSSLTVTAGEKVTMSCKSSQSLLNSGNQKNYLTWYQQKPGQPPKLLIYWASTRESGVPDRFTGSGSGTDFTLTISSVQAEDL
AVYYCQNDYSYPFTFGSGTKLEIKRTVAAPSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC SEQ ID NO: 49 hGBA-1 HC full
EVQLVQSGAEVKKPGESLKISCKGSGYSFTSYWIGWVRQMPGKGLEWMGNIYPGASDTRYAPSFQGQVTISADKSISTAYLQWSSLKAS
DTAMYYCARLWRGNSFDYWGQGTLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFLYSKLTVDKSRWQQGNVFSCSVMHEALHNHYTQKSLSLS
PGK SEQ ID NO: 50 hGBA-1, hGBA-2, hGBA-6, hGBA-8 LC full
DIVMTQSPDSLAVSLGERATINCKSSQSLLNSGNQKNYLAWYQQKPGQPPKLLIYWASTRESGVPDRFSGSGSGTDFTLTISSLQAEDV
AVYYCQNDYSYPFTFGQGTKVEIKRTVAAPSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC SEQ ID NO: 51 hGBA-2 HC full
EVQLVQSGAEVKKPGESLKISCKGSGYSFTSYWIGWVRQMPGKGLEWMGNIYPGDADTRYAPSFQGQVTISADKSISTAYLQWSSLKAS
DTAMYYCARMWRGNSFDYWGQGTLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFLYSKLTVDKSRWQQGNVFSCSVMHEALHNHYTQKSLSLS
PGK SEQ ID NO: 52 hGBA-3 HC full
EVQLVQSGAEVKKPGESLKISCKGSGYSFTSYWIGWVRQMPGKGLEWMGIIYPGASDTNYAPSFQGQVTISADKSISTAYLQWSSLKAS
DTAMYYCARIWRGNSFDYWGQGTLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFLYSKLTVDKSRWQQGNVFSCSVMHEALHNHYTQKSLSLS
PGK SEQ ID NO: 53 hGBA-3 LC full
DIVMTQSPDSLAVSLGERATINCKSSQSLLNSGNQKNYLAWYQQKPGQPPKLLIYWASTRESGVPDRFSGSGSGTDFTLTISSLQAEDV
AVYYCQNDYSYPLTFGQGTKVEIKRTVAAPSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC -continued

| SEQUENCES |
| --- |

SEQ ID NO: 54 hGBA-4 HC full
EVQLVQSGAEVKKPGESLKISCKGSGYSFTSYWIGWVRQMPGKGLEWMGIIYPGDAYTRYSPSFQGQVTISADKSISTAYLQWSSLKAS
DTAMYYCTRLWRGNSFDAWGQGTLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFLYSKLTVDKSRWQQGNVFSCSVMHEALHNHYTQKSLSLS
PGK SEQ ID NO: 55 hGBA-4 LC full
DIVMTQSPDSLAVSLGERATINCKSSQSLLNSGNQKNYLTWYQQKPGQPPKLLIYWASTRESGVPDRFSGSGSGTDFTLTISSLQAEDV
AVYYCQNDYSYPLTFGQGTKVEIKRTVAAPSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC SEQ ID NO: 56 hGBA-5 HC full
EVQLVQSGAEVKKPGESLKISCKGSGYSFTSYWIGWVRQMPGKGLEWMGIIYPGAAYTRYAPSFQGQVTISADKSISTAYLQWSSLKAS
DTAMYYCARLWRGNSFDYWGQGTLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFLYSKLTVDKSRWQQGNVFSCSVMHEALHNHYTQKSLSLS
PGK SEQ ID NO: 57 hGBA-5 LC full
DIVMTQSPDSLAVSLGERATINCKSSQSLLNSGNQKNYLAWYQQKPGQPPKLLIYWASTRESGVPDRFSGSGSGTDFTLTISSLQAEDV
AVYYCQQDYSYPFTFGQGTKVEIKRTVAAPSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC SEQ ID NO: 58 hGBA-6 HC full
EVQLVQSGAEVKKPGESLKISCKGSGYTFTSYWIGWVRQMPGKGLEWMGNIYPGASYTRYSPSFQGQVTISADKSISTAYLQWSSLKAS
DTAMYYCTRQWRGNSFDYWGQGTLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFLYSKLTVDKSRWQQGNVFSCSVMHEALHNHYTQKSLSLS
PGK SEQ ID NO: 59 hGBA-7 HC full
EVQLVQSGAEVKKPGESLKISCKGSGYSFTSYWIGWVRQMPGKGLEWMGNIYPGEAYTRYSPSFQGQVTISADKSISTAYLQWSSLKAS
DTAMYYCTRLWRGNSFDYWGQGTLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFLYSKLTVDKSRWQQGNVFSCSVMHEALHNHYTQKSLSLS
PGK SEQ ID NO: 60 hGBA-7 LC full
DIVMTQSPDSLAVSLGERATINCKSSQSVLNSGNQKNYLTWYQQKPGQPPKLLIYWASTRESGVPDRFSGSGSGTDFTLTISSLQAEDV
AVYYCQNDYSYPFTFGQGTKVEIKRTVAAPSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC SEQ ID NO: 61 hGBA-8 HC full
EVQLVQSGAEVKKPGESLKISCKGSGYSFTSYWIGWVRQMPGKGLEWMGNIYPSESYTNYAPSFQGQVTISADKSISTAYLQWSSLKAS
DTAMYYCTRLWRGNSFDYWGQGTLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFLYSKLTVDKSRWQQGNVFSCSVMHEALHNHYTQKSLSLS
PGK SEQ ID NO: 62 hGBA-9 HC full
EVQLVQSGAEVKKPGESLKISCKGSGYTFTSYWIGWVRQMPGKGLEWMGIIYPSAAYTRYAPSFQGQVTISADKSISTAYLQWSSLKAS
DTAMYYCTRMWRGNSFDYWGQGTLVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFLYSKLTVDKSRWQQGNVFSCSVMHEALHNHYTQKSLSLS
PGK SEQ ID NO: 63 hGBA-9, LC full
DIVMTQSPDSLAVSLGERATINCKSSQSVLNSGNQKNYLAWYQQKPGQPPKLLIYWASTRESGVPDRFSGSGSGTDFTLTISSLQAEDV
AVYYCQQDYSYPFTFGQGTKVEIKRTVAAPSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC SEQ ID NO: 64 constant heavy chain-CH1 + Fc domain
ASTKGPSVFPLAPSSKSTSGGTAALGCLVKDYFPEPVTVSWNSGALTSGVHTFPAVLQSSGLYSLSSWTVPSSSLGTQTYICNVNHKPS
NTKVDKKVEPKSCDKTHTCPPCPAPELLGGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVMHEALHNHYTQKSLSLSPGK -continued

| SEQUENCES |
| --- |

SEQ ID NO: 65
RTVAAPSVFIFPPSDEQLKSGTASVVCLLNNFYPREAKVQWKVDNALQSGNSQESVTEQDSKDSTYSLSSTLTLSKADYEKHKVYACEV
THQGLSSPVTKSFNRGEC

SEQ ID NO: 66
ASTKGPSVFPLAPSSKSTSGGTAALGCLVKDYFPEPVTVSWNSGALTSGVHTFPAVLQSSGLYSLSSWTVPSSSLGTQTYICNVNHKPS
NTKVDKKVEPKSCDKTHTCPPCPAPEAAGGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVMHEALHNHYTQKSLSLSPGK

SEQ ID NO: 67
ASTKGPSVFPLAPSSKSTSGGTAALGCLVKDYFPEPVTVSWNSGALTSGVHTFPAVLQSSGLYSLSSWTVPSSSLGTQTYICNVNHKPS
NTKVDKKVEPKSCDKTHTCPPCPAPEAAGGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALGAPIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVMHEALHNHYTQKSLSLSPGK

SEQ ID NO: 68
DQWSTQDLYN

SEQ ID NO: 69
NNPVTAVFNYQ

SEQ ID NO: 70
STQDLYNNPVTAVF

SEQ ID NO: 71
TNFWMSTANMYTG

SEQ ID NO: 72
ALMIVGIVLGAIGLLV

SEQ ID NO: 73
RIGSMEDSAKANMTLTSGIMFIVS

SEQ ID NO: 74
METDTLLLWVLLLWVPGSTGDAAQPARRARRTKLGTELGSTPVWWNSADGRMDQWSTQDLYNNPVTAVFNYQGLWRSCVRESSGFTECR
GYFTLLGLPAMLQAVRAAIQHSGGRSRRARTKTHLRRGSE

SEQ ID NO: 75
MDQWSTQDLYNNPVT

SEQ ID NO: 76
LYNNPVTAVFNYQGL

SEQ ID NO: 77
VFNYQGLWRSCVRES

SEQ ID NO: 78
QGLWRSCVRESSGFT

SEQ ID NO: 79
RSCVRESSGFTECRG

SEQ ID NO: 80
TEDEVQSYPSKHDYV

SEQ ID NO: 81
EVQSYPSKHDYV

SEQ ID NO: 82 consensus including IMAB362 HC CDR1
GYXFTSYWIX X in 3$^{rd}$ position is T or S, X in the last position is G or N SEQ ID NO: 83 consensus including IMAB362 HC CDR2
GXIYPXXXXTXYX X in 2$^{nd}$ position is N or I; X in 6$^{th}$ position is S or G; X in 7$^{th}$ position
is A, E or D; X in 8$^{th}$ position is A or S; X in 9$^{th}$ position is Yor D; X in 11$^{th}$
position is N or R; X in last position is A, N or S SEQ ID NO: 84 consensus including IMAB362 HC CDR3
XRXWRGNSFDX X in 1$^{st}$ position is A or T; X in 3$^{rd}$ position is L, M, I, S or Q; X in last
position is A or Y SEQ ID NO: 85
ggctatagctttacatcatattggattgga -continued

SEQUENCES

SEQ ID NO: 86
gggaacatttaccctggggcatcggatacgcgatacgca

SEQ ID NO: 87
gcgagactttggcgggggaatagcttcgactac

SEQ ID NO: 88
aaaagctcccaaagcctattgaactcgggaaaccaaaagaattacttggca

SEQ ID NO: 89
tgggcaagcacccgagagagc

SEQ ID NO: 90
caaaacgactattcatacccattcaca

SEQ ID NO: 91
ggatattcatttacaagctactggatcgga

SEQ ID NO: 92
ggaaatatataccccggagacgcggacacgagatacgca

SEQ ID NO: 93
gcgcggatgtggcgcggcaatagctttgactac

SEQ ID NO: 94
gggatcatctatccggggggcatccgataccaactatgcg

SEQ ID NO: 95
gctaggatttggcgaggaaatagctttgattat

SEQ ID NO: 96
aagagctcgcaaagtttgctgaactccgggaaccaaaagaattacctggca

SEQ ID NO: 97
tgggcatcaacgcgggaaagc

SEQ ID NO: 98
caaaacgactactcctatccgctgacc

SEQ ID NO: 99
ggatactcatttacatcatactggatagga

SEQ ID NO: 100
gggattatataccccggcgacgcttacactcgatattcg

SEQ ID NO: 101
acgaggctatggaggggggaatagctttgatgcc

SEQ ID NO: 102
aagagctcccaaagcctattgaactcgggaaatcaaaagaattatctgaca

SEQ ID NO: 103
tgggcctcgacaagggagagc

SEQ ID NO: 104
caaaatgactactcatacccgctgac

SEQ ID NO: 105
ggatatagctttacgagctactggatcgga

SEQ ID NO: 106
gggataatataccccggagcggcatacacgagatatgcg

SEQ ID NO: 107
gcgagactatggcgcgggaactcatttgattac

SEQ ID NO: 108
aaatcatcgcaatcattgctaaattcggggaaccaaaagaattatttggca

SEQ ID NO: 109
tgggcatccacgagagaatcg

SEQ ID NO: 110
caacaagattattcatacccatttaca

SEQUENCES

SEQ ID NO: 111
ggatatacatttacatcttactggatcgga

SEQ ID NO: 112
gggaacatttatcctggcgcgagctatacgcgctat

SEQ ID NO: 113
acccggcaatggaggggcaatagctttgactac

SEQ ID NO: 114
ggatattcctttacatcatactggatcggc

SEQ ID NO: 115
gggaacatatatcccggagaagcctatacgagatactcg

SEQ ID NO: 116
acgcgactatggaggggaaatagctttgactat

SEQ ID NO: 117
aagagctcccaatcagtcctgaactctgggaatcaaaagaattacctgaca

SEQ ID NO: 118
tgggcgagcacgagggagagc

SEQ ID NO: 119
caaaatgattattcatacccttcaca

SEQ ID NO: 120
ggatactcctttacatcatattggatcgga

SEQ ID NO: 121
ggaaacatatatccgagcgaatcatatacgaactacgcg

SEQ ID NO: 122
acgaggctatggaggggaatagcttcgactat

SEQ ID NO: 123
ggatatacattcacgagctactggatagga

SEQ ID NO: 124
ggaatcatatatccttccgcggcatatacgcgatatgcg

SEQ ID NO: 125
acgcggatgtggaggggaaatagctttgattac

SEQ ID NO: 126
aagagctcgcaatcggtcctgaatagcgggaaccaaaagaattatctggcc

SEQ ID NO: 127
caacaagactactcatacccatttaca

SEQ ID NO: 128
gaagtccaactggtccaatccggcgcggaggttaagaagcccggagaatcgctgaagatctcatgcaaagggagcggctatagctttac
atcatattggattggatgggtcaggcaaatgccggggaaggggctggaatggatggggaacatttaccctggggcatcggatacgcgat
acgcacctagctttcaagggcaagtcacaatttcggcggacaagagcatctcaacggcatacctgcaatggtcgagcttgaaggcatct
gatactgcaatgtactactgcgcgagactttggcgggggaatagcttcgactactgggggcagggtaccctggttacggtctcgagc SEQ ID NO: 129
gacattgtgatgacgcaaagccccgattcgctggctgtatcgctaggggagcgcgctacgatcaattgcaaaagctcccaaagcctatt
gaactcgggaaaccaaaagaattacttggcatggtatcaacaaaaccggggcaaccgccgaagctgctgatctattgggcaagcaccc
gagagagcggtgtcccggaccgatttagcgggagcggatcgggcaccgacttcacgctgacaataagctcattgcaagccgaggatgtg
gcggtctattattgccaaaacgactattcatacccattcacattcgggcaaggtaccaaggtcgagatcaag SEQ ID NO: 130
gaagtccaactggtccaatctggagcggaagtcaagaagcctggggagagcctgaaaatttcatgcaagggggagcggatattcatttac
aagctactggatcggatgggtccggcaaatgccggggaaggggcttggaatggatgggaaatatatacccggagacgcgggacacgagat
acgcaccgagctttcaagggcaggtcaccattagcgctgataaatcgatttcaaccgcatatctgcaatggtcatcgctgaaggcctcc
gacaccgcgatgtactattgcgcgcggatgtggcgcggcaatagctttgactactgggggcagggtaccctcgtcacggtctcgagc SEQ ID NO: 131
gaggtccaactggtccaaagcggcgcggaggtcaagaagcccgggagaatccctgaagattagctgcaaaggctccggctatagctttac
atcatattggatcggatgggtcagacaaatgccgggaaaggggacttgaatggatggggatcatctatccgggggcatccgataccaact
atgcgccgagcttccaagggcaggtcacgatatccgcggataaatcgattagcaccgcatatctgcaatggagctcgctgaaggcatcc
gacaccgcgatgtactactgcgctaggattttggcgaggaaatagctttgattattggggggcagggtacccttgtcacggtctcgagc -continued

SEQUENCES

SEQ ID NO: 132
gacattgtcatgacgcaaagccccgactcgctggccgtctcactgggggagcgggcgacaatcaactgcaagagctcgcaaagtttgct
gaactccgggaaccaaaagaattacctggcatggtatcaacaaaagccggggcaaccccgaagctgctgatatattgggcatcaacgc
gggaaagcggagtcccggatagatttagcggatctggatcggggaccgacttcacgctgacgatatctagccttcaagccgaggatgtg
gctgtatattattgccaaaacgactactcctatccgctgaccttcgggcaaggtaccaaggtcgagatcaag SEQ ID NO: 133
gaagtccaactagtccaaagcggagccgaagtcaagaaaccgggggagagcccttaagatctcatgcaaggggagcggatactcatttac
atcatactggataggatgggtcagacaaatgcccggcaaggggctggaatggatggggattatatacccggcgacgcttacactcgat
attcgccatcattccaagggcaggtcacgatatcggccgatataaatcgatatccacggcatacctgcaatggagctcactgaaagcatct
gatacggcaatgtattattgcacgaggctatggaggggggaatagctttgatgcctgggggcagggtaccctggtcacggtctcgagc SEQ ID NO: 134
gacatagttatgacacaatcgccggatagcctcgcggtcagccttggagagcgggcgacgatcaactgcaagagctcccaaagcctatt
gaactcgggaaatcaaaagaattatctgacatggtatcaacaaaagccggggcaacaccgaaactgctgatctattgggcctcgacaa
gggagagcggagtcccggaccgcttctctggatcgggaagcgggactgacttcacgctgaccataagctcgctgcaagccgaggacgtc
gccgtctattattgccaaaatgactactacccgctgacatttggccaaggtaccaaggtcgagatcaag SEQ ID NO: 135
gaggtgcaactggtacaatccggggcggaagtgaagaagccgggggaatcgctgaagataagctgcaaaggctctggatatagctttac
gagctactggatcggatgggtcaggcaaatgccggggaagggactggaatggatggggataatatacccggagcggcatacacgagat
atgcgccgagcttccaagggcaagtgacaataagcgcggacaaatcgattagcacggcatatctgcaatggtcctcgctgaaggcgagc
gataccgcaatgtactattgcgcgagactatggcgcgggaactcatttgattactgggggcagggtaccctagtgacggtctcgagc SEQ ID NO: 136
gacattgtcatgacgcaaagcccggatagcctggctgtatcgctgggggagagagcgacgatcaactgcaaatcatcgcaatcattgct
aaattcggggaaccaaaagaattatttggcatggtatcaacaaaagccggggcaaccgccgaaactgctgatttactgggcatccacga
gagaatcgggagtcccggaccgattagcggatctgggagcgggaccgatttcacgctgaccattagctcgctgcaagcggaggatgtg
gcggtctattactgccaacaagattattcatacccatttacatttgggcaaggtaccaaggtcgagatcaag SEQ ID NO: 137
gaagtacaattggttcaatcggggggccgaagtcaagaagccggggggaatcgctgaagatatcctgcaagggggagcggatatacatttac
atcttactggatcggatgggtcagacaaatgcccggaaaggggcttgaatggatggggaacatttatcctggcgcgagctatacgcgct
atagcccgagcttccaagggcaggtcacgattagcgccgacaagagcatttcgacggcatacctgcaatggagctcgctgaaagcatcg
gatacggcaatgtattactgcacccggcaatggagggggcaatagctttgactactgggggcagggtaccctagtcacggtctcgagc SEQ ID NO: 138
gaagttcaattggtccaatctggagccgaagtcaagaagcccggagaatcgctgaagattagctgcaagggggagcggatattcctttac
atcatactggatcggctgggtcagacaaatgcccggaaagggactggaatggatggggaacatatatcccggagaagcctatacgagat
actcgccatcatttcaaggacaggtcaccataagcgcggacaagagcataagcaccgcatacctgcaatggagctcgctgaaggcatch
gacaccgccatgtattactgcacgcgactatggagggggaaatagctttgactattgggggcagggtaccttagtcacggtctcgagc SEQ ID NO: 139
gatatagtaatgactcaatcacccgatagcttggctgtgagcctgggagaaagagctacaatcaactgcaagagctcccaatcagtcct
gaactctgggaatcaaaagaattacctgacatggtatcaacaaaagcccggacaaccgccgaagctgctgatctactgggcgagcacga
gggagagcggagtcccggatcgattttctggctccgggagcggaaccgacttcacactgactattagctcgctgcaagcggaggacgtc
gccgtctactattgccaaaatgattattcatacccctttacatttgggcaaggtaccaaggtcgagatcaag SEQ ID NO: 140
gaggtgcaactagtgcaatcggggggccgaagtgaagaaacctggggaatcgctgaagatatcatgcaagggggagcggatactccttttac
atcatattggatcggatgggtcaggcaaatgccgggggaagggggctggaatggatgggaacatatatccgagcgaatcatatacgaact
acgcgccgagctttcaaggacaagtcacgatatccgcggatataaatcgatatcgaccgcatacctgcaatggagctcgctgaaggcttcc
gacactgcgatgtattactgcacgaggctatggagggggaatagcttcgactattgggggcagggtaccctggtgacggtctcgagc SEQ ID NO: 141
gaagtccaattagtccaatcggggggccgaggtcaagaagccgggggaatcgctcaagataagctgcaagggatcgggatatacattcac
gagctactggataggatgggtcaggcaaatgccgggggaagggggctggaatggatgggaatcatatatccttccgcgggcatatacgcgat
atgcgccatcatttcaaggacaggtcacgataagcgccgacaagagcattagcaccgcatacctgcaatggtcgagccttaaggcatcg
gacaccgcgatgtactactgcacgcggatgtggagggggaaatagctttgattactgggggcagggtaccctagtcacggtctcgagc SEQ ID NO: 142
gacatcgtcatgacgcaaagcccggactcgctggcggtctcgctgggggagcgggccacaataaattgcaagagctcgcaatcggtcct
gaatagcgggaaccaaaagaattatctggcctggtatcaacaaaagccggggcaaccaccgaagctgctaatctattgggcgagcacga
gggagagcggagtcccgatcgattagcggatcgggaagcgggaccgatttcacgctgacgatttcgagcctacaagccgaggatgtg
gcggtctattactgccaacaagactactcatacccatttacatttggacaaggtaccaaggtcgagatcaag SEQ ID NO: 143 sortase tag
RLPXTGG
X is any of the 20 natural amino acids SEQ ID NO: 144 sortase tag
GGGGSLPXTGG
X is any of the 20 natural amino acids

REFERENCES

Alegre, M. L., A. M. Collins, V. L. Pulito, R. A. Brosius, W. C. Olson, R. A. Zivin, R. Knowles, J. R. Thistlethwaite, L. K. Jolliffe, and J. A. Bluestone. 1992. 'Effect of a single amino acid mutation on the activating and immunosuppressive properties of a "humanized" OKT3 monoclonal antibody', *J Immunol*, 148: 3461-8.

An, Z., G. Forrest, R. Moore, M. Cukan, P. Haytko, L. Huang, S. Vitelli, J. Z. Zhao, P. Lu, J. Hua, C. R. Gibson, B. R. Harvey, D. Montgomery, D. Zaller, F. Wang, and W. Strohl. 2009. 'IgG2m4, an engineered antibody isotype with reduced Fc function', *MAbs*, 1: 572-9.

Bolt, S., E. Routledge, I. Lloyd, L. Chatenoud, H. Pope, S. D. Gorman, M. Clark, and H. Waldmann. 1993. 'The generation of a humanized, non-mitogenic CD3 monoclonal antibody which retains in vitro immunosuppressive properties', *Eur J Immunol*, 23: 403-11.

Chang, Z. L., and Y. Y. Chen. 2017. 'CARS: Synthetic Immunoreceptors for Cancer Therapy and Beyond', *Trends Mol Med*, 23: 430-50.

Chu, S. Y., I. Vostiar, S. Karki, G. L. Moore, G. A. Lazar, E. Pong, P. F. Joyce, D. E. Szymkowski, and J. R. Desjarlais. 2008. 'Inhibition of B cell receptor-mediated activation of primary human B cells by coengagement of CD19 and FcgammaRIIb with Fc-engineered antibodies', *Mol Immunol*, 45: 3926-33.

Dall'Acqua, W. F., R. M. Woods, E. S. Ward, S. R. Palaszynski, N. K. Patel, Y. A. Brewah, H. Wu, P. A. Kiener, and S. Langermann. 2002. 'Increasing the affinity of a human IgG1 for the neonatal Fc receptor: biological consequences', *J Immunol*, 169: 5171-80.

Diebolder, C. A., F. J. Beurskens, R. N. de Jong, R. I. Koning, K. Strumane, M. A. Lindorfer, M. Voorhorst, D. Ugurlar, S. Rosati, A. J. Heck, J. G. van de Winkel, I. A. Wilson, A. J. Koster, R. P. Taylor, E. O. Saphire, D. R. Burton, J. Schuurman, P. Gros, and P. W. Parren. 2014. 'Complement is activated by IgG hexamers assembled at the cell surface', *Science*, 343: 1260-3.

Ellerman, D. 2019. 'Bispecific T-cell engagers: Towards understanding variables influencing the in vitro potency and tumor selectivity and their modulation to enhance their efficacy and safety', *Methods*, 154: 102-17.

Green, M. R., and J. Sambrook. 2012. *Molecular Cloning: A Laboratory Manual (Fourth Edition)* (Cold Spring Harbor Laboratory Press).

Hashimoto, Y., W. Zhou, K. Hamauchi, K. Shirakura, T. Doi, K. Yagi, T. Sawasaki, Y. Okada, M. Kondoh, and H. Takeda. 2018. 'Engineered membrane protein antigens successfully induce antibodies against extracellular regions of claudin-5', *Sci Rep*, 8: 8383.

Hewitt, K. J., R. Agarwal, and P. J. Morin. 2006. 'The claudin gene family: expression in normal and neoplastic tissues', *BMC Cancer*, 6: 186.

Idusogie, E. E., P. Y. Wong, L. G. Presta, H. Gazzano-Santoro, K. Totpal, M. Ultsch, and M. G. Mulkerrin. 2001. 'Engineered antibodies with increased activity to recruit complement', *J Immunol*, 166: 2571-5.

Jacobi, A., B. Enenkel, P. Garidel, C. Eckermann, M. Knappenberger, I. Presser, and H. Kaufmann. 2014. 'Process Development and Manufacturing of Therapeutic Antibodies.' in S. Duebel and J. M. Reichert (eds.), *Handbook of Therapeutic Antibodies, Second Edition* (Wiley-VCH Verlag GmbH & Co. KGaA.).

Jiang, H., Z. Shi, P. Wang, C. Wang, L. Yang, G. Du, H. Zhang, B. Shi, J. Jia, Q. Li, H. Wang, and Z. Li. 2018.

54

'Claudin18.2-Specific Chimeric Antigen Receptor Engineered T Cells for the Treatment of Gastric Cancer', *J Natl Cancer Inst.*

June, C. H., and M. Sadelain. 2018. 'Chimeric Antigen Receptor Therapy', *N Engl J Med*, 379: 64-73.

Lazar, G. A., W. Dang, S. Karki, O. Vafa, J. S. Peng, L. Hyun, C. Chan, H. S. Chung, A. Eivazi, S. C. Yoder, J. Vielmetter, D. F. Carmichael, R. J. Hayes, and B. I. Dahiyat. 2006. 'Engineered antibody Fc variants with enhanced effector function', *Proc Natl Acad Sci USA*, 103: 4005-10.

Leabman, M. K., Y. G. Meng, R. F. Kelley, L. E. DeForge, K. J. Cowan, and S. Iyer. 2013. 'Effects of altered FcgammaR binding on antibody pharmacokinetics in cynomolgus monkeys', *MAbs*, 5: 896-903.

Lo, M., H. S. Kim, R. K. Tong, T. W. Bainbridge, J. M. Vernes, Y. Zhang, Y. L. Lin, S. Chung, M. S. Dennis, Y. J. Zuchero, R. J. Watts, J. A. Couch, Y. G. Meng, J. K. Atwal, R. J. Brerski, C. Spiess, and J. A. Ernst. 2017. 'Effector-attenuating Substitutions That Maintain Antibody Stability and Reduce Toxicity in Mice', *J Biol Chem*, 292: 3900-08.

Martin, A. C. R., and J. Allemn. 2014. 'Bioinformatics Tools for Analysis of Antibodies.' in, *Handbook of Therapeutic Antibodies, Second Edition* (Wiley-VCH Verlag GmbH & Co. KGaA.).

Mimoto, F., T. Igawa, T. Kuramochi, H. Katada, S. Kadono, T. Kamikawa, M. Shida-Kawazoe, and K. Hattori. 2013. 'Novel asymmetrically engineered antibody Fc variant with superior FcgammaR binding affinity and specificity compared with afucosylated Fc variant', *MAbs*, 5: 229-36.

Moore, G. L., H. Chen, S. Karki, and G. A. Lazar. 2010. 'Engineered Fc variant antibodies with enhanced ability to recruit complement and mediate effector functions', *MAbs*, 2: 181-9.

Natsume, A., M. In, H. Takamura, T. Nakagawa, Y. Shimizu, K. Kitajima, M. Wakitani, S. Ohta, M. Satoh, K. shitara, and R. Niwa. 2008. 'Engineered antibodies of IgG1/IgG3 mixed isotype with enhanced cytotoxic activities', *Cancer Res*, 68: 3863-72.

Niimi, T., K. Nagashima, J. M. Ward, P. Minoo, D. B. Zimonjic, N. C. Popescu, and S. Kimura. 2001. 'claudin-18, a novel downstream target gene for the T/EBP/NKX2.1 homeodomain transcription factor, encodes lung- and stomach-specific isoforms through alternative splicing', *Mol Cell Biol*, 21: 7380-90.

Richards, J. O., S. Karki, G. A. Lazar, H. Chen, W. Dang, and J. R. Desjarlais. 2008. 'Optimization of antibody binding to FcgammaRIIa enhances macrophage phagocytosis of tumor cells', *Mol Cancer Ther*, 7: 2517-27.

Rother, R. P., S. A. Rollins, C. F. Mojcik, R. A. Brodsky, and L. Bell. 2007. 'Discovery and development of the complement inhibitor eculizumab for the treatment of paroxysmal nocturnal hemoglobinuria', *Nat Biotechnol*, 25: 1256-64.

Sahin, U., M. Koslowski, K. Dhaene, D. Usener, G. Brandenburg, G. Seitz, C. Huber, and O. Tureci. 2008. 'Claudin-18 splice variant 2 is a pan-cancer target suitable for therapeutic antibody development', *Clin Cancer Res*, 14: 7624-34.

Saldanha, J. W. 2014. 'Humanization Strategies.' in S. Duebel and J. M. Reichert (eds.), *Handbook of Therapeutic Antibodies, Second Edition* (Wiley-VCH Verlag GmbH & Co. KGaA.).

Sauerborn, M. 2014. 'The Immunogenicity of Therapeutic Antibodies.' in S. Duebel and J. M. Reichert (eds.),

*Handbook of Therapeutic Antibodies, Second Edition* (Wiley-VCH Verlag GmbH & Co. KGaA.).

Shang, L., B. Daubeuf, M. Triantafilou, R. Olden, F. Depis, A. C. Raby, S. Herren, A. Dos Santos, P. Malinge, I. Dunn-Siegrist, S. Benmkaddem, A. Geinoz, G. Magistrelli, F. Rousseau, V. Buatois, S. Salgado-Pires, W. Reith, R. Monteiro, J. Pugin, O. Leger, W. Ferlin, M. Kosco-Vilbois, K. Triantafilou, and G. Elson. 2014. 'Selective antibody intervention of Toll-like receptor 4 activation through Fc gamma receptor tethering', *J Biol Chem,* 289: 15309-18.

Shields, R. L., A. K. Namenuk, K. Hong, Y. G. Meng, J. Rae, J. Briggs, D. Xie, J. Lai, A. Stadlen, B. Li, J. A. Fox, and L. G. Presta. 2001. 'High resolution mapping of the binding site on human IgG1 for Fc gamma RI, Fc gamma RII, Fc gamma RIII, and FcRn and design of IgG1 variants with improved binding to the Fc gamma R', *J Biol Chem,* 276: 6591-604.

Stavenhagen, J. B., S. Gorlatov, N. Tuaillon, C. T. Rankin, H. Li, S. Burke, L. Huang, S. Vijh, S. Johnson, E. Bonvini, and S. Koenig. 2007. 'Fc optimization of therapeutic antibodies enhances their ability to kill tumor cells in vitro and controls tumor expansion in vivo via low-affinity activating Fcgamma receptors', *Cancer Res,* 67: 8882-90.

Tao, M. H., and S. L. Morrison. 1989. 'Studies of aglycosylated chimeric mouse-human IgG. Role of carbohydrate in the structure and effector functions mediated by the human IgG constant region', *J Immunol,* 143: 2595-601.

Vafa, O., G. L. Gilliland, R. J. Brerski, B. Strake, T. Wilkinson, E. R. Lacy, B. Scallon, A. Teplyakov, T. J. Malia, and W. R. Strohl. 2014. 'An engineered Fc variant of an IgG eliminates all immune effector functions via structural perturbations', *Methods,* 65: 114-26.

Waldmeier, L., I. Hellmann, C. K. Gutknecht, F. I. Wolter, S. C. Cook, S. T. Reddy, U. Grawunder, and R. R. Beerli. 2016. 'Transpo-mAb display: Transposition-mediated B cell display and functional screening of full-length IgG antibody libraries', *MAbs,* 8: 726-40.

Walker, M. R., J. Lund, K. M. Thompson, and R. Jefferis. 1989. 'Aglycosylation of human IgG1 and IgG3 monoclonal antibodies can eliminate recognition by human cells expressing Fc gamma RI and/or Fc gamma RII receptors', *Biochem J,* 259: 347-53.

Wang, X., M. Mathieu, and R. J. Brerski. 2018. 'IgG Fc engineering to modulate antibody effector functions', *Protein Cell,* 9: 63-73.

Xu, D., M. L. Alegre, S. S. Varga, A. L. Rothermel, A. M. Collins, V. L. Pulito, L. S. Hanna, K. P. Dolan, P. W. Parren, J. A. Bluestone, L. K. Jolliffe, and R. A. Zivin. 2000. 'In vitro characterization of five humanized OKT3 effector function variant antibodies', *Cell Immunol,* 200: 16-26.

Yu, D., and J. R. Turner. 2008. 'Stimulus-induced reorganization of tight junction structure: the role of membrane traffic', *Biochim Biophys Acta,* 1778: 709-16.

Zalevsky, J., A. K. Chamberlain, H. M. Horton, S. Karki, I. W. Leung, T. J. Sproule, G. A. Lazar, D. C. Roopenian, and J. R. Desjarlais. 2010. 'Enhanced antibody half-life improves in vivo activity', *Nat Biotechnol,* 28: 157-9.

CN109762067
WO2000/015659
WO2004/047863
WO2005/113587
WO2007/059997
WO2008/145338
WO2013/167259
WO2013/174509
WO2014/075788
WO2014/127906
WO2016/166122
WO2018/006882
WO2019/175617
WO2019/219089

The invention claimed is:

1. An antibody or fragment thereof binding to claudin 18.2 (CLDN18.2), which comprises:

a. HCDR1, HCDR2 and HCDR3 sequences of SEQ ID NO: 7, SEQ ID NO: 9 and SEQ ID NO: 18, respectively and
  LCDR1, LCDR2 and LCDR3 sequences of SEQ ID NO: 25, SEQ ID NO: 5 and SEQ ID NO: 29, respectively;

b. HCDR1, HCDR2 and HCDR3 sequences of SEQ ID NO: 7, SEQ ID NO: 10 and SEQ ID NO: 19, respectively and LCDR1, LCDR2 and LCDR3 sequences of SEQ ID NO: 25, SEQ ID NO: 5 and SEQ ID NO: 29, respectively;

c. HCDR1, HCDR2 and HCDR3 sequences of SEQ ID NO: 7, SEQ ID NO: 11 and SEQ ID NO: 20, respectively and LCDR1, LCDR2 and LCDR3 sequences of SEQ ID NO: 25, SEQ ID NO: 5 and SEQ ID NO: 30, respectively;

d. HCDR1, HCDR2 and HCDR3 sequences of SEQ ID NO: 7, SEQ ID NO: 12 and SEQ ID NO: 21, respectively and LCDR1, LCDR2 and LCDR3 sequences of SEQ ID NO: 26, SEQ ID NO: 5 and SEQ ID NO: 30, respectively;

e. HCDR1, HCDR2 and HCDR3 sequences of SEQ ID NO: 7, SEQ ID NO: 13 and SEQ ID NO: 18, respectively and
the LCDR1, LCDR2 and LCDR3 sequences of SEQ ID NO: 25, SEQ ID NO: 5 and SEQ ID NO: 31, respectively;

f. HCDR1, HCDR2 and HCDR3 sequences of SEQ ID NO: 8, SEQ ID NO: 14 and SEQ ID NO: 22, respectively and
LCDR1, LCDR2 and LCDR3 sequences of SEQ ID NO: 25, SEQ ID NO: 5 and SEQ ID NO: 29, respectively;

g. HCDR1, HCDR2 and HCDR3 sequences of SEQ ID NO: 7, SEQ ID NO: 15 and SEQ ID NO: 23, respectively and
LCDR1, LCDR2 and LCDR3 sequences of SEQ ID NO: 27, SEQ ID NO: 5 and SEQ ID NO: 29, respectively;

h. HCDR1, HCDR2 and HCDR3 sequences of SEQ ID NO: 7, SEQ ID NO: 16 and SEQ ID NO: 23, respectively and
LCDR1, LCDR2 and LCDR3 sequences of SEQ ID NO: 25, SEQ ID NO: 5 and SEQ ID NO: 29, respectively; or i. HCDR1, HCDR2 and HCDR3 sequences of SEQ ID NO: 8, SEQ ID NO: 17 and SEQ ID NO: 24, respectively and
LCDR1, LCDR2 and LCDR3 sequences of SEQ ID NO: 28, SEQ ID NO: 5 and SEQ ID NO: 31, respectively.

2. The antibody or fragment thereof of claim 1, comprising:

a. a VH sequence of SEQ ID NO: 32;

b. a VH sequence of SEQ ID NO: 34;

c. a VH sequence of SEQ ID NO: 35;

d. a VH sequence of SEQ ID NO: 37;

e. a VH sequence of SEQ ID NO: 39;

f. a VH sequence of SEQ ID NO: 41;

g. a VH sequence of SEQ ID NO: 42;

h. a VH sequence of SEQ ID NO: 44 or i. a VH sequence of SEQ ID NO: 45; and j. a VL sequence of SEQ ID NO: 33;

k. a VL sequence of SEQ ID NO: 36;

l. A VL sequence of SEQ ID NO: 38;

m. a VL sequence of SEQ ID NO: 40;

n. a VL sequence of SEQ ID NO: 43; or o. a VL sequence of SEQ ID NO: 46.

3. The antibody or fragment thereof of claim 1, comprising:

a. a VH sequence of SEQ ID NO: 32 and a VL sequence of SEQ ID NO: 33;

b. a VH sequence of SEQ ID NO: 34 and a VL sequence of SEQ ID NO: 33;

c. a VH sequence of SEQ ID NO: 35 and a VL sequence of SEQ ID NO: 36;

d. a VH sequence of SEQ ID NO: 37 and a VL sequence of SEQ ID NO: 38;

e. a VH sequence of SEQ ID NO: 39 and a VL sequence of SEQ ID NO: 40;

f. a VH sequence of SEQ ID NO: 41 and a VL sequence of SEQ ID NO: 33;

g. a VH sequence of SEQ ID NO: 42 and a VL sequence of SEQ ID NO: 43;

h. a VH sequence of SEQ ID NO: 44 and a VL sequence of SEQ ID NO: 33; or i. a VH sequence of SEQ ID NO: 45 and a VL sequence of SEQ ID NO: 46.

4. The antibody or fragment thereof of claim 1, consisting of:

a. the heavy chain sequence of SEQ ID NO: 49 and light chain sequence of SEQ ID NO: 50;

b. the heavy chain sequence of SEQ ID NO: 51 and light chain sequence of SEQ ID NO: 50;

c. the heavy chain sequence of SEQ ID NO: 52 and light chain sequence of SEQ ID NO: 53;

d. the heavy chain sequence of SEQ ID NO: 54 and light chain sequence of SEQ ID NO: 55;

e. the heavy chain sequence of SEQ ID NO: 56 and light chain sequence of SEQ ID NO: 57;

f. the heavy chain sequence of SEQ ID NO: 58 and light chain sequence of SEQ ID NO: 50;

g. the heavy chain sequence of SEQ ID NO: 59 and light chain sequence of SEQ ID NO: 60;

h. the heavy chain sequence of SEQ ID NO: 61 and light chain sequence of SEQ ID NO: 50; or i. the heavy chain sequence of SEQ ID NO: 62 and light chain sequence of SEQ ID NO: 63.

5. The antibody or fragment thereof of claim 1, wherein the format of the antibody or fragment thereof is selected from the group consisting of IgA1, IgA2, IgD, IgE, IgG1, IgG2, IgG3, IgG4, synthetic IgG, IgM, F(ab)$_2$, scFv, IgGΔCH2, F(ab')$_2$, scFvCH3, Fab, scFv4, scFv3, scFv2, dsFv, Fv, scFv-Fc, (scFv)$_2$, a non-depleting IgG, a diabody, and a bivalent antibody, or Fc-engineered versions thereof.

6. The antibody or fragment thereof of claim 1, wherein the antibody or fragment thereof (i) is humanized;

(ii) is isolated; and/or (iii) does not bind to claudin 18.1 (CLDN18.1).

7. The antibody or fragment thereof of claim 1, wherein the antibody or fragment thereof exhibits increased binding to claudin 18.2 (CLDN18.2) as compared to a reference antibody, wherein increased binding is measured as EC50 value and/or maxMFI value by flow cytometry titration on cells expressing claudin 18.2 (CLDN18.2), wherein the cells are HEK293T cells or PA-TU-8988S cells, wherein the reference antibody comprises a heavy chain sequence of SEQ ID NO: 47 and a light chain sequence of SEQ ID NO: 48.

8. The antibody or fragment of claim 7, wherein (i) the measured EC50 value of the antibody is at least 10% lower than the EC50 value of the reference antibody; and/or (ii) the measured maxMFI value of the antibody is at least 10% higher than the maxMFI value of the reference antibody.

9. A nucleic acid encoding the antibody or fragment thereof of claim 1.

10. A vector comprising the nucleic acid of claim 9.

11. A host cell comprising the nucleic acid of claim 9.

12. A method of treating a subject suffering from a neoplastic disease overexpressing claudin 18.2 (CLDN18.2), comprising administering the antibody or fragment thereof of claim 1, to the subject.

13. The method of claim 12, wherein the neoplastic disease overexpressing claudin 18.2 (CLDN18.2) is selected from the group consisting of pancreatic, gastric, esophageal, ovarian and lung cancer.

14. A host cell comprising the vector of claim 10.

15. A method of treating a subject suffering from a neoplastic disease overexpressing claudin 18.2 (CLDN18.2), comprising administering the nucleic acid of claim 9 to the subject.

16. A method of treating a subject suffering from a neoplastic disease overexpressing claudin 18.2 (CLDN18.2), comprising administering the vector of claim 10 to the subject.

17. A method of treating a subject suffering from a neoplastic disease overexpressing claudin 18.2 (CLDN18.2), comprising administering the host cell of claim 11 to the subject.

* * * * *

SEQUENCE LISTING

```
<160> NUMBER OF SEQ ID NOS: 144

<210> SEQ ID NO 1
<211> LENGTH: 10
<212> TYPE: PRT
<213> ORGANISM: Artificial Sequence
<220> FEATURE:
<223> OTHER INFORMATION: HCDR1 Consensus Sequence
<220> FEATURE:
<221> NAME/KEY: MISC_FEATURE
<222> LOCATION: (3)..(3)
<223> OTHER INFORMATION: T or S

<400> SEQUENCE: 1

Gly Tyr Xaa Phe Thr Ser Tyr Trp Ile Gly
1               5                   10

<210> SEQ ID NO 2
<211> LENGTH: 13
<212> TYPE: PRT
<213> ORGANISM: Artificial Sequence
<220> FEATURE:
<223> OTHER INFORMATION: HCDR2 Consensus Sequence
<220> FEATURE:
<221> NAME/KEY: MISC_FEATURE
<222> LOCATION: (2)..(2)
<223> OTHER INFORMATION: N or I
<220> FEATURE:
<221> NAME/KEY: MISC_FEATURE
```

-continued

```
<222> LOCATION: (6)..(6)
<223> OTHER INFORMATION: S or G
<220> FEATURE:
<221> NAME/KEY: MISC_FEATURE
<222> LOCATION: (7)..(7)
<223> OTHER INFORMATION: A, E or D
<220> FEATURE:
<221> NAME/KEY: MISC_FEATURE
<222> LOCATION: (8)..(8)
<223> OTHER INFORMATION: A or S
<220> FEATURE:
<221> NAME/KEY: MISC_FEATURE
<222> LOCATION: (9)..(9)
<223> OTHER INFORMATION: Y or D
<220> FEATURE:
<221> NAME/KEY: MISC_FEATURE
<222> LOCATION: (11)..(11)
<223> OTHER INFORMATION: N or R
<220> FEATURE:
<221> NAME/KEY: MISC_FEATURE
<222> LOCATION: (13)..(13)
<223> OTHER INFORMATION: A or S

<400> SEQUENCE: 2

Gly Xaa Ile Tyr Pro Xaa Xaa Xaa Xaa Thr Xaa Tyr Xaa
1               5                   10

<210> SEQ ID NO 3
<211> LENGTH: 11
<212> TYPE: PRT
<213> ORGANISM: Artificial Sequence
<220> FEATURE:
<223> OTHER INFORMATION: HCDR3 Consensus Sequence
<220> FEATURE:
<221> NAME/KEY: MISC_FEATURE
<222> LOCATION: (1)..(1)
<223> OTHER INFORMATION: A or T
<220> FEATURE:
<221> NAME/KEY: MISC_FEATURE
<222> LOCATION: (3)..(3)
<223> OTHER INFORMATION: L, M, I or Q
<220> FEATURE:
<221> NAME/KEY: MISC_FEATURE
<222> LOCATION: (11)..(11)
<223> OTHER INFORMATION: A or Y

<400> SEQUENCE: 3

Xaa Arg Xaa Trp Arg Gly Asn Ser Phe Asp Xaa
1               5                   10

<210> SEQ ID NO 4
<211> LENGTH: 17
<212> TYPE: PRT
<213> ORGANISM: Artificial Sequence
<220> FEATURE:
<223> OTHER INFORMATION: LCDR1 Consensus Sequence
<220> FEATURE:
<221> NAME/KEY: MISC_FEATURE
<222> LOCATION: (6)..(6)
<223> OTHER INFORMATION: L or V
<220> FEATURE:
<221> NAME/KEY: MISC_FEATURE
<222> LOCATION: (17)..(17)
<223> OTHER INFORMATION: T or A

<400> SEQUENCE: 4

Lys Ser Ser Gln Ser Xaa Leu Asn Ser Gly Asn Gln Lys Asn Tyr Leu
1               5                   10                  15

Xaa

<210> SEQ ID NO 5
<211> LENGTH: 7
```

```
<212> TYPE: PRT
<213> ORGANISM: Artificial Sequence
<220> FEATURE:
<223> OTHER INFORMATION: LCDR2 Consensus Sequence

<400> SEQUENCE: 5

Trp Ala Ser Thr Arg Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: LCDR3 Consensus Sequence
<220> FEATURE:
<221> NAME/KEY: MISC_FEATURE
<222> LOCATION: (2)..(2)
<223> OTHER INFORMATION: N or Q
<220> FEATURE:
<221> NAME/KEY: MISC_FEATURE
<222> LOCATION: (8)..(8)
<223> OTHER INFORMATION: L or F

<400> SEQUENCE: 6

Gln Xaa Asp Tyr Ser Tyr Pro Xaa Thr
1               5

<210> SEQ ID NO 7
<211> LENGTH: 10
<212> TYPE: PRT
<213> ORGANISM: Artificial Sequence
<220> FEATURE:
<223> OTHER INFORMATION: hGBA-1, hGBA-2, hGBA-3, hGBA-4, hGBA-5, hGBA-7,
      hGBA-8 HCDR1 Sequence

<400> SEQUENCE: 7

Gly Tyr Ser Phe Thr Ser Tyr Trp Ile Gly
1               5                   10

<210> SEQ ID NO 8
<211> LENGTH: 10
<212> TYPE: PRT
<213> ORGANISM: Artificial Sequence
<220> FEATURE:
<223> OTHER INFORMATION: hGBA-6, hGBA-9 HCDR1 Sequence

<400> SEQUENCE: 8

Gly Tyr Thr Phe Thr Ser Tyr Trp Ile Gly
1               5                   10

<210> SEQ ID NO 9
<211> LENGTH: 13
<212> TYPE: PRT
<213> ORGANISM: Artificial Sequence
<220> FEATURE:
<223> OTHER INFORMATION: hGBA-1 HCDR2 Sequence

<400> SEQUENCE: 9

Gly Asn Ile Tyr Pro Gly Ala Ser Asp Thr Arg Tyr Ala
1               5                   10

<210> SEQ ID NO 10
<211> LENGTH: 13
<212> TYPE: PRT
<213> ORGANISM: Artificial Sequence
<220> FEATURE:
<223> OTHER INFORMATION: hGBA-2 HCDR2 Sequence
```

```
<400> SEQUENCE: 10

Gly Asn Ile Tyr Pro Gly Asp Ala Asp Thr Arg Tyr Ala
1               5                   10

<210> SEQ ID NO 11
<211> LENGTH: 13
<212> TYPE: PRT
<213> ORGANISM: Artificial Sequence
<220> FEATURE:
<223> OTHER INFORMATION: hGBA-3 HCDR2 Sequence

<400> SEQUENCE: 11

Gly Ile Ile Tyr Pro Gly Ala Ser Asp Thr Asn Tyr Ala
1               5                   10

<210> SEQ ID NO 12
<211> LENGTH: 13
<212> TYPE: PRT
<213> ORGANISM: Artificial Sequence
<220> FEATURE:
<223> OTHER INFORMATION: hGBA-4 HCDR2 Sequence

<400> SEQUENCE: 12

Gly Ile Ile Tyr Pro Gly Asp Ala Tyr Thr Arg Tyr Ser
1               5                   10

<210> SEQ ID NO 13
<211> LENGTH: 13
<212> TYPE: PRT
<213> ORGANISM: Artificial Sequence
<220> FEATURE:
<223> OTHER INFORMATION: hGBA-5 HCDR2 Sequence

<400> SEQUENCE: 13

Gly Ile Ile Tyr Pro Gly Ala Ala Tyr Thr Arg Tyr Ala
1               5                   10

<210> SEQ ID NO 14
<211> LENGTH: 13
<212> TYPE: PRT
<213> ORGANISM: Artificial Sequence
<220> FEATURE:
<223> OTHER INFORMATION: hGBA-6 HCDR2 Sequence

<400> SEQUENCE: 14

Gly Asn Ile Tyr Pro Gly Ala Ser Tyr Thr Arg Tyr Ser
1               5                   10

<210> SEQ ID NO 15
<211> LENGTH: 13
<212> TYPE: PRT
<213> ORGANISM: Artificial Sequence
<220> FEATURE:
<223> OTHER INFORMATION: hGBA-7 HCDR2 Sequence

<400> SEQUENCE: 15

Gly Asn Ile Tyr Pro Gly Glu Ala Tyr Thr Arg Tyr Ser
1               5                   10

<210> SEQ ID NO 16
<211> LENGTH: 13
<212> TYPE: PRT
<213> ORGANISM: Artificial Sequence
<220> FEATURE:
<223> OTHER INFORMATION: hGBA-8 HCDR1 Sequence

<400> SEQUENCE: 16
```

```
Gly Asn Ile Tyr Pro Ser Glu Ser Tyr Thr Asn Tyr Ala
1               5                   10

<210> SEQ ID NO 17
<211> LENGTH: 13
<212> TYPE: PRT
<213> ORGANISM: Artificial Sequence
<220> FEATURE:
<223> OTHER INFORMATION: hGBA-9 HCDR2 Sequence

<400> SEQUENCE: 17

Gly Ile Ile Tyr Pro Ser Ala Ala Tyr Thr Arg Tyr Ala
1               5                   10

<210> SEQ ID NO 18
<211> LENGTH: 11
<212> TYPE: PRT
<213> ORGANISM: Artificial Sequence
<220> FEATURE:
<223> OTHER INFORMATION: hGBA-1, hGBA-5 HCDR3 Sequence

<400> SEQUENCE: 18

Ala Arg Leu Trp Arg Gly Asn Ser Phe Asp Tyr
1               5                   10

<210> SEQ ID NO 19
<211> LENGTH: 11
<212> TYPE: PRT
<213> ORGANISM: Artificial Sequence
<220> FEATURE:
<223> OTHER INFORMATION: hGBA-2 HCDR3 Sequence

<400> SEQUENCE: 19

Ala Arg Met Trp Arg Gly Asn Ser Phe Asp Tyr
1               5                   10

<210> SEQ ID NO 20
<211> LENGTH: 11
<212> TYPE: PRT
<213> ORGANISM: Artificial Sequence
<220> FEATURE:
<223> OTHER INFORMATION: hGBA-3 HCDR3 Sequence

<400> SEQUENCE: 20

Ala Arg Ile Trp Arg Gly Asn Ser Phe Asp Tyr
1               5                   10

<210> SEQ ID NO 21
<211> LENGTH: 11
<212> TYPE: PRT
<213> ORGANISM: Artificial Sequence
<220> FEATURE:
<223> OTHER INFORMATION: hGBA-4 HCDR3 Sequence

<400> SEQUENCE: 21

Thr Arg Leu Trp Arg Gly Asn Ser Phe Asp Ala
1               5                   10

<210> SEQ ID NO 22
<211> LENGTH: 11
<212> TYPE: PRT
<213> ORGANISM: Artificial Sequence
<220> FEATURE:
<223> OTHER INFORMATION: hGBA-6 HCDR3 Sequence

<400> SEQUENCE: 22
```

```
Thr Arg Gln Trp Arg Gly Asn Ser Phe Asp Tyr
1               5                   10

<210> SEQ ID NO 23
<211> LENGTH: 11
<212> TYPE: PRT
<213> ORGANISM: Artificial Sequence
<220> FEATURE:
<223> OTHER INFORMATION: hGBA-7, hGBA-8 HCDR3 Sequence

<400> SEQUENCE: 23

Thr Arg Leu Trp Arg Gly Asn Ser Phe Asp Tyr
1               5                   10

<210> SEQ ID NO 24
<211> LENGTH: 11
<212> TYPE: PRT
<213> ORGANISM: Artificial Sequence
<220> FEATURE:
<223> OTHER INFORMATION: hGBA-9 HCDR3 Sequence

<400> SEQUENCE: 24

Thr Arg Met Trp Arg Gly Asn Ser Phe Asp Tyr
1               5                   10

<210> SEQ ID NO 25
<211> LENGTH: 17
<212> TYPE: PRT
<213> ORGANISM: Artificial Sequence
<220> FEATURE:
<223> OTHER INFORMATION: hGBA-1, hGBA-3, hGBA-5, hGBA-6, hGBA-8 LCDR1
      Sequence

<400> SEQUENCE: 25

Lys Ser Ser Gln Ser Leu Leu Asn Ser Gly Asn Gln Lys Asn Tyr Leu
1               5                   10                  15

Ala

<210> SEQ ID NO 26
<211> LENGTH: 17
<212> TYPE: PRT
<213> ORGANISM: Artificial Sequence
<220> FEATURE:
<223> OTHER INFORMATION: hGBA-4 LCDR1 Sequence

<400> SEQUENCE: 26

Lys Ser Ser Gln Ser Leu Leu Asn Ser Gly Asn Gln Lys Asn Tyr Leu
1               5                   10                  15

Thr

<210> SEQ ID NO 27
<211> LENGTH: 17
<212> TYPE: PRT
<213> ORGANISM: Artificial Sequence
<220> FEATURE:
<223> OTHER INFORMATION: hGBA-7 LCDR1 Sequence

<400> SEQUENCE: 27

Lys Ser Ser Gln Ser Val Leu Asn Ser Gly Asn Gln Lys Asn Tyr Leu
1               5                   10                  15

Thr

<210> SEQ ID NO 28
<211> LENGTH: 17
<212> TYPE: PRT
```

```
<213> ORGANISM: Artificial Sequence
<220> FEATURE:
<223> OTHER INFORMATION: hGBA-9 LCDR1 Sequence

<400> SEQUENCE: 28

Lys Ser Ser Gln Ser Val Leu Asn Ser Gly Asn Gln Lys Asn Tyr Leu
1               5                   10                  15

Ala

<210> SEQ ID NO 29
<211> LENGTH: 9
<212> TYPE: PRT
<213> ORGANISM: Artificial Sequence
<220> FEATURE:
<223> OTHER INFORMATION: hGBA-1, hGBA-3, hGBA-6, hGBA-7, hGBA-8 LCDR3
      Sequence

<400> SEQUENCE: 29

Gln Asn Asp Tyr Ser Tyr Pro Phe Thr
1               5

<210> SEQ ID NO 30
<211> LENGTH: 9
<212> TYPE: PRT
<213> ORGANISM: Artificial Sequence
<220> FEATURE:
<223> OTHER INFORMATION: hGBA-4 LCDR3 Sequence

<400> SEQUENCE: 30

Gln Asn Asp Tyr Ser Tyr Pro Leu Thr
1               5

<210> SEQ ID NO 31
<211> LENGTH: 9
<212> TYPE: PRT
<213> ORGANISM: Artificial Sequence
<220> FEATURE:
<223> OTHER INFORMATION: hGBA-5, hGBA-9 LCDR3 Sequence

<400> SEQUENCE: 31

Gln Gln Asp Tyr Ser Tyr Pro Phe Thr
1               5

<210> SEQ ID NO 32
<211> LENGTH: 118
<212> TYPE: PRT
<213> ORGANISM: Artificial Sequence
<220> FEATURE:
<223> OTHER INFORMATION: hGBA-1 VH Sequence

<400> SEQUENCE: 32

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Asn Ile Tyr Pro Gly Ala Ser Asp Thr Arg Tyr Ala Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95
```

-continued

```
Ala Arg Leu Trp Arg Gly Asn Ser Phe Asp Tyr Trp Gly Gln Gly Thr
        100                 105                 110

Leu Val Thr Val Ser Ser
        115
```

```
<210> SEQ ID NO 33
<211> LENGTH: 113
<212> TYPE: PRT
<213> ORGANISM: Artificial Sequence
<220> FEATURE:
<223> OTHER INFORMATION: hGBA-1, hGBA-2, hGBA-6 , hGBA-8  VL Sequence

<400> SEQUENCE: 33
```

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
        20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Phe Thr Phe Gly Gln Gly Thr Lys Val Glu Ile
                100                 105                 110

Lys
```

```
<210> SEQ ID NO 34
<211> LENGTH: 118
<212> TYPE: PRT
<213> ORGANISM: Artificial Sequence
<220> FEATURE:
<223> OTHER INFORMATION: hGBA-2 VH Sequence

<400> SEQUENCE: 34
```

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
        20                  25                  30

Trp Ile Gly Trp Val Arg Gln Met Pro Gly Lys Gly Leu Glu Trp Met
        35                  40                  45

Gly Asn Ile Tyr Pro Gly Asp Ala Asp Thr Arg Tyr Ala Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Met Trp Arg Gly Asn Ser Phe Asp Tyr Trp Gly Gln Gly Thr
        100                 105                 110

Leu Val Thr Val Ser Ser
        115
```

```
<210> SEQ ID NO 35
<211> LENGTH: 118
<212> TYPE: PRT
<213> ORGANISM: Artificial Sequence
<220> FEATURE:
```

<223> OTHER INFORMATION: hGBA-3 VH Sequence

<400> SEQUENCE: 35

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Ala Ser Asp Thr Asn Tyr Ala Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ile Trp Arg Gly Asn Ser Phe Asp Tyr Trp Gly Gln Gly Thr
            100                 105                 110

Leu Val Thr Val Ser Ser
        115
```

<210> SEQ ID NO 36
<211> LENGTH: 113
<212> TYPE: PRT
<213> ORGANISM: Artificial Sequence
<220> FEATURE:
<223> OTHER INFORMATION: hGBA-3 VL Sequence

<400> SEQUENCE: 36

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Leu Thr Phe Gly Gln Gly Thr Lys Val Glu Ile
            100                 105                 110

Lys
```

<210> SEQ ID NO 37
<211> LENGTH: 118
<212> TYPE: PRT
<213> ORGANISM: Artificial Sequence
<220> FEATURE:
<223> OTHER INFORMATION: hGBA-4 VH Sequence

<400> SEQUENCE: 37

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45
```

-continued

```
Gly Ile Ile Tyr Pro Gly Asp Ala Tyr Thr Arg Tyr Ser Pro Ser Phe
    50              55              60

Gln Gly Gln Val Thr Ile Ser Ala Asp Lys Ser Ile Ser Thr Ala Tyr
65              70              75              80

Leu Gln Trp Ser Ser Leu Lys Ala Ser Asp Thr Ala Met Tyr Tyr Cys
            85              90              95

Thr Arg Leu Trp Arg Gly Asn Ser Phe Asp Ala Trp Gly Gln Gly Thr
            100             105             110

Leu Val Thr Val Ser Ser
        115
```

```
<210> SEQ ID NO 38
<211> LENGTH: 113
<212> TYPE: PRT
<213> ORGANISM: Artificial Sequence
<220> FEATURE:
<223> OTHER INFORMATION: hGBA-4 VL Sequence

<400> SEQUENCE: 38

Asp Ile Val Met Thr Gln Ser Pro Asp Ser Leu Ala Val Ser Leu Gly
1               5               10              15

Glu Arg Ala Thr Ile Asn Cys Lys Ser Ser Gln Ser Leu Leu Asn Ser
            20              25              30

Gly Asn Gln Lys Asn Tyr Leu Thr Trp Tyr Gln Gln Lys Pro Gly Gln
        35              40              45

Pro Pro Lys Leu Leu Ile Tyr Trp Ala Ser Thr Arg Glu Ser Gly Val
    50              55              60

Pro Asp Arg Phe Ser Gly Ser Gly Ser Gly Thr Asp Phe Thr Leu Thr
65              70              75              80

Ile Ser Ser Leu Gln Ala Glu Asp Val Ala Val Tyr Tyr Cys Gln Asn
            85              90              95

Asp Tyr Ser Tyr Pro Leu Thr Phe Gly Gln Gly Thr Lys Val Glu Ile
            100             105             110

Lys
```

```
<210> SEQ ID NO 39
<211> LENGTH: 118
<212> TYPE: PRT
<213> ORGANISM: Artificial Sequence
<220> FEATURE:
<223> OTHER INFORMATION: hGBA-5 VH Sequence

<400> SEQUENCE: 39

Glu Val Gln Leu Val Gln Ser Gly Ala Glu Val Lys Lys Pro Gly Glu
1               5               10              15

Ser Leu Lys Ile Ser Cys Lys Gly Ser Gly Tyr Ser Phe Thr Ser Tyr
            20              25              30

Trp Ile Gly Trp Val Arg Gln Met Pro Gly Lys Gly Leu Glu Trp Met
        35              40              45

Gly Ile Ile Tyr Pro Gly Ala Ala Tyr Thr Arg Tyr Ala Pro Ser Phe
    50              55              60

Gln Gly Gln Val Thr Ile Ser Ala Asp Lys Ser Ile Ser Thr Ala Tyr
65              70              75              80

Leu Gln Trp Ser Ser Leu Lys Ala Ser Asp Thr Ala Met Tyr Tyr Cys
            85              90              95

Ala Arg Leu Trp Arg Gly Asn Ser Phe Asp Tyr Trp Gly Gln Gly Thr
            100             105             110
```

```
Leu Val Thr Val Ser Ser
        115

<210> SEQ ID NO 40
<211> LENGTH: 113
<212> TYPE: PRT
<213> ORGANISM: Artificial Sequence
<220> FEATURE:
<223> OTHER INFORMATION: hGBA-5 VL Sequence

<400> SEQUENCE: 40

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Asp Tyr Ser Tyr Pro Phe Thr Phe Gly Gln Gly Thr Lys Val Glu Ile
            100                 105                 110

Lys

<210> SEQ ID NO 41
<211> LENGTH: 118
<212> TYPE: PRT
<213> ORGANISM: Artificial Sequence
<220> FEATURE:
<223> OTHER INFORMATION: hGBA-6 VH Sequence

<400> SEQUENCE: 41

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Ser Tyr
            20                  25                  30

Trp Ile Gly Trp Val Arg Gln Met Pro Gly Lys Gly Leu Glu Trp Met
        35                  40                  45

Gly Asn Ile Tyr Pro Gly Ala Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Thr Arg Gln Trp Arg Gly Asn Ser Phe Asp Tyr Trp Gly Gln Gly Thr
            100                 105                 110

Leu Val Thr Val Ser Ser
        115

<210> SEQ ID NO 42
<211> LENGTH: 118
<212> TYPE: PRT
<213> ORGANISM: Artificial Sequence
<220> FEATURE:
<223> OTHER INFORMATION: hGBA-7 VH Sequence
```

<400> SEQUENCE: 42

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Asn Ile Tyr Pro Gly Glu Ala Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Thr Arg Leu Trp Arg Gly Asn Ser Phe Asp Tyr Trp Gly Gln Gly Thr
            100                 105                 110

Leu Val Thr Val Ser Ser
        115

<210> SEQ ID NO 43
<211> LENGTH: 113
<212> TYPE: PRT
<213> ORGANISM: Artificial Sequence
<220> FEATURE:
<223> OTHER INFORMATION: hGBA-7 VL Sequence

<400> SEQUENCE: 43

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Phe Thr Phe Gly Gln Gly Thr Lys Val Glu Ile
            100                 105                 110

Lys

<210> SEQ ID NO 44
<211> LENGTH: 118
<212> TYPE: PRT
<213> ORGANISM: Artificial Sequence
<220> FEATURE:
<223> OTHER INFORMATION: hGBA-8 VH Sequence

<400> SEQUENCE: 44

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Asn Ile Tyr Pro Ser Glu Ser Tyr Thr Asn Tyr Ala Pro Ser Phe

```
             50                  55                  60
Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Thr Arg Leu Trp Arg Gly Asn Ser Phe Asp Tyr Trp Gly Gln Gly Thr
            100                 105                 110

Leu Val Thr Val Ser Ser
        115
```

<210> SEQ ID NO 45
<211> LENGTH: 118
<212> TYPE: PRT
<213> ORGANISM: Artificial Sequence
<220> FEATURE:
<223> OTHER INFORMATION: hGBA-9 VH Sequence

<400> SEQUENCE: 45

```
Glu Val Gln Leu Val Gln Ser Gly Ala Glu Val Lys Lys Pro Gly Glu
1                   5                   10                  15

Ser Leu Lys Ile Ser Cys Lys Gly Ser Gly Tyr Thr Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Ser Ala Ala Tyr Thr Arg Tyr Ala Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Thr Arg Met Trp Arg Gly Asn Ser Phe Asp Tyr Trp Gly Gln Gly Thr
            100                 105                 110

Leu Val Thr Val Ser Ser
        115
```

<210> SEQ ID NO 46
<211> LENGTH: 113
<212> TYPE: PRT
<213> ORGANISM: Artificial Sequence
<220> FEATURE:
<223> OTHER INFORMATION: hGBA-9 VL Sequence

<400> SEQUENCE: 46

```
Asp Ile Val Met Thr Gln Ser Pro Asp Ser Leu Ala Val Ser Leu Gly
1                   5                   10                  15

Glu Arg Ala Thr Ile Asn Cys Lys Ser Ser Gln Ser Val Leu Asn Ser
                20                  25                  30

Gly Asn Gln Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Asp Tyr Ser Tyr Pro Phe Thr Phe Gly Gln Gly Thr Lys Val Glu Ile
            100                 105                 110
```

-continued

Lys

```
<210> SEQ ID NO 47
<211> LENGTH: 448
<212> TYPE: PRT
<213> ORGANISM: Artificial Sequence
<220> FEATURE:
<223> OTHER INFORMATION: IMAB362 HC full

<400> SEQUENCE: 47

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
            100                 105                 110

Thr Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
```

-continued

```
            355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly Lys
            435                 440                 445

<210> SEQ ID NO 48
<211> LENGTH: 220
<212> TYPE: PRT
<213> ORGANISM: Artificial Sequence
<220> FEATURE:
<223> OTHER INFORMATION: IMAB362 Light Chain full

<400> SEQUENCE: 48

Asp Ile Val Met Thr Gln Ser Pro Ser Ser Leu Thr Val Thr Ala Gly
1                   5                   10                  15
Glu Lys Val Thr Met Ser Cys Lys Ser Ser Gln Ser Leu Leu Asn Ser
                20                  25                  30
Gly Asn Gln Lys Asn Tyr Leu Thr Trp Tyr Gln Gln Lys Pro Gly Gln
            35                  40                  45
Pro Pro Lys Leu Leu Ile Tyr Trp Ala Ser Thr Arg Glu Ser Gly Val
    50                  55                  60
Pro Asp Arg Phe Thr Gly Ser Gly Ser Gly Thr Asp Phe Thr Leu Thr
65                  70                  75                  80
Ile Ser Ser Val Gln Ala Glu Asp Leu Ala Val Tyr Tyr Cys Gln Asn
                85                  90                  95
Asp Tyr Ser Tyr Pro Phe Thr Phe Gly Ser Gly Thr Lys Leu Glu Ile
            100                 105                 110
Lys Arg Thr Val Ala Ala Pro Ser Val Phe Ile Phe Pro Pro Ser Asp
            115                 120                 125
Glu Gln Leu Lys Ser Gly Thr Ala Ser Val Val Cys Leu Leu Asn Asn
        130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
            180                 185                 190
Glu Lys His Lys Val Tyr Ala Cys Glu Val Thr His Gln Gly Leu Ser
        195                 200                 205
Ser Pro Val Thr Lys Ser Phe Asn Arg Gly Glu Cys
    210                 215                 220

<210> SEQ ID NO 49
<211> LENGTH: 448
<212> TYPE: PRT
<213> ORGANISM: Artificial Sequence
<220> FEATURE:
<223> OTHER INFORMATION: hGBA-1 Heavy Chain Sequence

<400> SEQUENCE: 49
```

-continued

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
            35                  40                  45

Gly Asn Ile Tyr Pro Gly Ala Ser Asp Thr Arg Tyr Ala Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg Leu Trp Arg Gly Asn Ser Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
```

-continued

```
                  420              425              430

Leu His Asn His Tyr Thr Gln Lys Ser Leu Ser Leu Ser Pro Gly Lys
        435              440              445

<210> SEQ ID NO 50
<211> LENGTH: 220
<212> TYPE: PRT
<213> ORGANISM: Artificial Sequence
<220> FEATURE:
<223> OTHER INFORMATION: hGBA-1, hGBA-2, hGBA-6, hGBA-8 Light Chain
      Sequence

<400> SEQUENCE: 50

Asp Ile Val Met Thr Gln Ser Pro Asp Ser Leu Ala Val Ser Leu Gly
1               5               10              15

Glu Arg Ala Thr Ile Asn Cys Lys Ser Ser Gln Ser Leu Leu Asn Ser
            20              25              30

Gly Asn Gln Lys Asn Tyr Leu Ala Trp Tyr Gln Gln Lys Pro Gly Gln
        35              40              45

Pro Pro Lys Leu Leu Ile Tyr Trp Ala Ser Thr Arg Glu Ser Gly Val
    50              55              60

Pro Asp Arg Phe Ser Gly Ser Gly Ser Gly Thr Asp Phe Thr Leu Thr
65              70              75              80

Ile Ser Ser Leu Gln Ala Glu Asp Val Ala Val Tyr Tyr Cys Gln Asn
            85              90              95

Asp Tyr Ser Tyr Pro Phe Thr Phe Gly Gln Gly Thr Lys Val Glu Ile
            100             105             110

Lys Arg Thr Val Ala Ala Pro Ser Val Phe Ile Phe Pro Pro Ser Asp
            115             120             125

Glu Gln Leu Lys Ser Gly Thr Ala Ser Val Val Cys Leu Leu Asn Asn
        130             135             140

Phe Tyr Pro Arg Glu Ala Lys Val Gln Trp Lys Val Asp Asn Ala Leu
145             150             155             160

Gln Ser Gly Asn Ser Gln Glu Ser Val Thr Glu Gln Asp Ser Lys Asp
            165             170             175

Ser Thr Tyr Ser Leu Ser Ser Thr Leu Thr Leu Ser Lys Ala Asp Tyr
            180             185             190

Glu Lys His Lys Val Tyr Ala Cys Glu Val Thr His Gln Gly Leu Ser
        195             200             205

Ser Pro Val Thr Lys Ser Phe Asn Arg Gly Glu Cys
    210             215             220

<210> SEQ ID NO 51
<211> LENGTH: 448
<212> TYPE: PRT
<213> ORGANISM: Artificial Sequence
<220> FEATURE:
<223> OTHER INFORMATION: hGBA-2 Heavy Chain Sequence

<400> SEQUENCE: 51

Glu Val Gln Leu Val Gln Ser Gly Ala Glu Val Lys Lys Pro Gly Glu
1               5               10              15

Ser Leu Lys Ile Ser Cys Lys Gly Ser Gly Tyr Ser Phe Thr Ser Tyr
            20              25              30

Trp Ile Gly Trp Val Arg Gln Met Pro Gly Lys Gly Leu Glu Trp Met
        35              40              45

Gly Asn Ile Tyr Pro Gly Asp Ala Asp Thr Arg Tyr Ala Pro Ser Phe
    50              55              60
```

-continued

```
Gln Gly Gln Val Thr Ile Ser Ala Asp Lys Ser Ile Ser Thr Ala Tyr
65              70                  75                  80

Leu Gln Trp Ser Ser Leu Lys Ala Ser Asp Thr Ala Met Tyr Tyr Cys
            85                  90                  95

Ala Arg Met Trp Arg Gly Asn Ser Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445
```

```
<210> SEQ ID NO 52
<211> LENGTH: 448
<212> TYPE: PRT
<213> ORGANISM: Artificial Sequence
<220> FEATURE:
```

<223> OTHER INFORMATION: hGBA-3 Heavy Chain Sequence

<400> SEQUENCE: 52

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Ala Ser Asp Thr Asn Tyr Ala Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ile Trp Arg Gly Asn Ser Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

-continued

```
Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 53
<211> LENGTH: 220
<212> TYPE: PRT
<213> ORGANISM: Artificial Sequence
<220> FEATURE:
<223> OTHER INFORMATION: hGBA-3 Light Chain Sequence

<400> SEQUENCE: 53

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 54
<211> LENGTH: 448
<212> TYPE: PRT
<213> ORGANISM: Artificial Sequence
<220> FEATURE:
<223> OTHER INFORMATION: hGBA-4 Heavy Chain Sequence

<400> SEQUENCE: 54

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45
```

-continued

```
Gly Ile Ile Tyr Pro Gly Asp Ala Tyr Thr Arg Tyr Ser Pro Ser Phe
    50              55              60

Gln Gly Gln Val Thr Ile Ser Ala Asp Lys Ser Ile Ser Thr Ala Tyr
65              70              75              80

Leu Gln Trp Ser Ser Leu Lys Ala Ser Asp Thr Ala Met Tyr Tyr Cys
            85              90              95

Thr Arg Leu Trp Arg Gly Asn Ser Phe Asp Ala Trp Gly Gln Gly Thr
            100             105             110

Leu Val Thr Val Ser Ser Ala Ser Thr Lys Gly Pro Ser Val Phe Pro
            115             120             125

Leu Ala Pro Ser Ser Lys Ser Thr Ser Gly Gly Thr Ala Ala Leu Gly
    130             135             140

Cys Leu Val Lys Asp Tyr Phe Pro Glu Pro Val Thr Val Ser Trp Asn
145             150             155             160

Ser Gly Ala Leu Thr Ser Gly Val His Thr Phe Pro Ala Val Leu Gln
            165             170             175

Ser Ser Gly Leu Tyr Ser Leu Ser Ser Val Val Thr Val Pro Ser Ser
            180             185             190

Ser Leu Gly Thr Gln Thr Tyr Ile Cys Asn Val Asn His Lys Pro Ser
            195             200             205

Asn Thr Lys Val Asp Lys Lys Val Glu Pro Lys Ser Cys Asp Lys Thr
    210             215             220

His Thr Cys Pro Pro Cys Pro Ala Pro Glu Leu Leu Gly Gly Pro Ser
225             230             235             240

Val Phe Leu Phe Pro Pro Lys Pro Lys Asp Thr Leu Met Ile Ser Arg
            245             250             255

Thr Pro Glu Val Thr Cys Val Val Val Asp Val Ser His Glu Asp Pro
            260             265             270

Glu Val Lys Phe Asn Trp Tyr Val Asp Gly Val Glu Val His Asn Ala
            275             280             285

Lys Thr Lys Pro Arg Glu Glu Gln Tyr Asn Ser Thr Tyr Arg Val Val
    290             295             300

Ser Val Leu Thr Val Leu His Gln Asp Trp Leu Asn Gly Lys Glu Tyr
305             310             315             320

Lys Cys Lys Val Ser Asn Lys Ala Leu Pro Ala Pro Ile Glu Lys Thr
            325             330             335

Ile Ser Lys Ala Lys Gly Gln Pro Arg Glu Pro Gln Val Tyr Thr Leu
            340             345             350

Pro Pro Ser Arg Asp Glu Leu Thr Lys Asn Gln Val Ser Leu Thr Cys
            355             360             365

Leu Val Lys Gly Phe Tyr Pro Ser Asp Ile Ala Val Glu Trp Glu Ser
    370             375             380

Asn Gly Gln Pro Glu Asn Asn Tyr Lys Thr Thr Pro Pro Val Leu Asp
385             390             395             400

Ser Asp Gly Ser Phe Phe Leu Tyr Ser Lys Leu Thr Val Asp Lys Ser
            405             410             415

Arg Trp Gln Gln Gly Asn Val Phe Ser Cys Ser Val Met His Glu Ala
            420             425             430

Leu His Asn His Tyr Thr Gln Lys Ser Leu Ser Leu Ser Pro Gly Lys
            435             440             445
```

<210> SEQ ID NO 55
<211> LENGTH: 220

```
<212> TYPE: PRT
<213> ORGANISM: Artificial Sequence
<220> FEATURE:
<223> OTHER INFORMATION: hGBA-4 Light Chain Sequence

<400> SEQUENCE: 55

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 56
<211> LENGTH: 448
<212> TYPE: PRT
<213> ORGANISM: Artificial Sequence
<220> FEATURE:
<223> OTHER INFORMATION: hGBA-5 Heavy Chain Sequence

<400> SEQUENCE: 56

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Ala Ala Tyr Thr Arg Tyr Ala Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Trp Arg Gly Asn Ser Phe Asp Tyr Trp Gly Gln Gly Thr
            100                 105                 110
```

-continued

```
Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
        435                 440                 445
```

<210> SEQ ID NO 57
<211> LENGTH: 220
<212> TYPE: PRT
<213> ORGANISM: Artificial Sequence
<220> FEATURE:
<223> OTHER INFORMATION: hGBA-5 Light Chain Sequence

<400> SEQUENCE: 57

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30
```

```
Gly Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Asp Tyr Ser Tyr Pro Phe Thr Phe Gly Gln Gly Thr Lys Val Glu Ile
                100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220
```

```
<210> SEQ ID NO 58
<211> LENGTH: 448
<212> TYPE: PRT
<213> ORGANISM: Artificial Sequence
<220> FEATURE:
<223> OTHER INFORMATION: hGBA-6 Heavy Chain Sequence

<400> SEQUENCE: 58
```

```
Glu Val Gln Leu Val Gln Ser Gly Ala Glu Val Lys Lys Pro Gly Glu
1                   5                   10                  15

Ser Leu Lys Ile Ser Cys Lys Gly Ser Gly Tyr Thr Phe Thr Ser Tyr
                20                  25                  30

Trp Ile Gly Trp Val Arg Gln Met Pro Gly Lys Gly Leu Glu Trp Met
        35                  40                  45

Gly Asn Ile Tyr Pro Gly Ala Ser Tyr Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Thr Arg Gln Trp Arg Gly Asn Ser Phe Asp Tyr Trp Gly Gln Gly Thr
                100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
        180             185             190

Ser Leu Gly Thr Gln Thr Tyr Ile Cys Asn Val Asn His Lys Pro Ser
        195             200             205

Asn Thr Lys Val Asp Lys Lys Val Glu Pro Lys Ser Cys Asp Lys Thr
    210             215             220

His Thr Cys Pro Pro Cys Pro Ala Pro Glu Leu Leu Gly Gly Pro Ser
225             230             235             240

Val Phe Leu Phe Pro Pro Lys Pro Lys Asp Thr Leu Met Ile Ser Arg
        245             250             255

Thr Pro Glu Val Thr Cys Val Val Val Asp Val Ser His Glu Asp Pro
        260             265             270

Glu Val Lys Phe Asn Trp Tyr Val Asp Gly Val Glu Val His Asn Ala
        275             280             285

Lys Thr Lys Pro Arg Glu Glu Gln Tyr Asn Ser Thr Tyr Arg Val Val
    290             295             300

Ser Val Leu Thr Val Leu His Gln Asp Trp Leu Asn Gly Lys Glu Tyr
305             310             315             320

Lys Cys Lys Val Ser Asn Lys Ala Leu Pro Ala Pro Ile Glu Lys Thr
        325             330             335

Ile Ser Lys Ala Lys Gly Gln Pro Arg Glu Pro Gln Val Tyr Thr Leu
        340             345             350

Pro Pro Ser Arg Asp Glu Leu Thr Lys Asn Gln Val Ser Leu Thr Cys
        355             360             365

Leu Val Lys Gly Phe Tyr Pro Ser Asp Ile Ala Val Glu Trp Glu Ser
        370             375             380

Asn Gly Gln Pro Glu Asn Asn Tyr Lys Thr Thr Pro Pro Val Leu Asp
385             390             395             400

Ser Asp Gly Ser Phe Phe Leu Tyr Ser Lys Leu Thr Val Asp Lys Ser
        405             410             415

Arg Trp Gln Gln Gly Asn Val Phe Ser Cys Ser Val Met His Glu Ala
        420             425             430

Leu His Asn His Tyr Thr Gln Lys Ser Leu Ser Leu Ser Pro Gly Lys
        435             440             445
```

```
<210> SEQ ID NO 59
<211> LENGTH: 448
<212> TYPE: PRT
<213> ORGANISM: Artificial Sequence
<220> FEATURE:
<223> OTHER INFORMATION: hGBA-7 Heavy Chain Sequence

<400> SEQUENCE: 59
```

```
Glu Val Gln Leu Val Gln Ser Gly Ala Glu Val Lys Lys Pro Gly Glu
1               5               10              15

Ser Leu Lys Ile Ser Cys Lys Gly Ser Gly Tyr Ser Phe Thr Ser Tyr
        20              25              30

Trp Ile Gly Trp Val Arg Gln Met Pro Gly Lys Gly Leu Glu Trp Met
        35              40              45

Gly Asn Ile Tyr Pro Gly Glu Ala Tyr Thr Arg Tyr Ser Pro Ser Phe
    50              55              60

Gln Gly Gln Val Thr Ile Ser Ala Asp Lys Ser Ile Ser Thr Ala Tyr
65              70              75              80

Leu Gln Trp Ser Ser Leu Lys Ala Ser Asp Thr Ala Met Tyr Tyr Cys
        85              90              95
```

```
Thr Arg Leu Trp Arg Gly Asn Ser Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445
```

```
<210> SEQ ID NO 60
<211> LENGTH: 220
<212> TYPE: PRT
<213> ORGANISM: Artificial Sequence
<220> FEATURE:
<223> OTHER INFORMATION: hGBA-7 Light Chain Sequence

<400> SEQUENCE: 60
```

```
Asp Ile Val Met Thr Gln Ser Pro Asp Ser Leu Ala Val Ser Leu Gly
1               5                   10                  15
```

-continued

```
Glu Arg Ala Thr Ile Asn Cys Lys Ser Ser Gln Ser Val Leu Asn Ser
            20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
    210                 215                 220

<210> SEQ ID NO 61
<211> LENGTH: 448
<212> TYPE: PRT
<213> ORGANISM: Artificial Sequence
<220> FEATURE:
<223> OTHER INFORMATION: hGBA-8 Heavy Chain Sequence

<400> SEQUENCE: 61

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
            35                  40                  45

Gly Asn Ile Tyr Pro Ser Glu Ser Tyr Thr Asn Tyr Ala Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Thr Arg Leu Trp Arg Gly Asn Ser Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160
```

-continued

```
Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445
```

```
<210> SEQ ID NO 62
<211> LENGTH: 448
<212> TYPE: PRT
<213> ORGANISM: Artificial Sequence
<220> FEATURE:
<223> OTHER INFORMATION: hGBA-9 Heavy Chain Sequence

<400> SEQUENCE: 62
```

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Ser Tyr
            20                  25                  30

Trp Ile Gly Trp Val Arg Gln Met Pro Gly Lys Gly Leu Glu Trp Met
            35                  40                  45

Gly Ile Ile Tyr Pro Ser Ala Ala Tyr Thr Arg Tyr Ala Pro Ser Phe
    50                  55                  60

Gln Gly Gln Val Thr Ile Ser Ala Asp Lys Ser Ile Ser Thr Ala Tyr
65                  70                  75                  80
```

Leu Gln Trp Ser Ser Leu Lys Ala Ser Asp Thr Ala Met Tyr Tyr Cys
            85              90              95

Thr Arg Met Trp Arg Gly Asn Ser Phe Asp Tyr Trp Gly Gln Gly Thr
            100             105             110

Leu Val Thr Val Ser Ser Ala Ser Thr Lys Gly Pro Ser Val Phe Pro
            115             120             125

Leu Ala Pro Ser Ser Lys Ser Thr Ser Gly Gly Thr Ala Ala Leu Gly
    130             135             140

Cys Leu Val Lys Asp Tyr Phe Pro Glu Pro Val Thr Val Ser Trp Asn
145             150             155             160

Ser Gly Ala Leu Thr Ser Gly Val His Thr Phe Pro Ala Val Leu Gln
            165             170             175

Ser Ser Gly Leu Tyr Ser Leu Ser Ser Val Val Thr Val Pro Ser Ser
            180             185             190

Ser Leu Gly Thr Gln Thr Tyr Ile Cys Asn Val Asn His Lys Pro Ser
            195             200             205

Asn Thr Lys Val Asp Lys Lys Val Glu Pro Lys Ser Cys Asp Lys Thr
    210             215             220

His Thr Cys Pro Pro Cys Pro Ala Pro Glu Leu Leu Gly Gly Pro Ser
225             230             235             240

Val Phe Leu Phe Pro Pro Lys Pro Lys Asp Thr Leu Met Ile Ser Arg
            245             250             255

Thr Pro Glu Val Thr Cys Val Val Val Asp Val Ser His Glu Asp Pro
            260             265             270

Glu Val Lys Phe Asn Trp Tyr Val Asp Gly Val Glu Val His Asn Ala
            275             280             285

Lys Thr Lys Pro Arg Glu Glu Gln Tyr Asn Ser Thr Tyr Arg Val Val
    290             295             300

Ser Val Leu Thr Val Leu His Gln Asp Trp Leu Asn Gly Lys Glu Tyr
305             310             315             320

Lys Cys Lys Val Ser Asn Lys Ala Leu Pro Ala Pro Ile Glu Lys Thr
            325             330             335

Ile Ser Lys Ala Lys Gly Gln Pro Arg Glu Pro Gln Val Tyr Thr Leu
            340             345             350

Pro Pro Ser Arg Asp Glu Leu Thr Lys Asn Gln Val Ser Leu Thr Cys
            355             360             365

Leu Val Lys Gly Phe Tyr Pro Ser Asp Ile Ala Val Glu Trp Glu Ser
    370             375             380

Asn Gly Gln Pro Glu Asn Asn Tyr Lys Thr Thr Pro Pro Val Leu Asp
385             390             395             400

Ser Asp Gly Ser Phe Phe Leu Tyr Ser Lys Leu Thr Val Asp Lys Ser
            405             410             415

Arg Trp Gln Gln Gly Asn Val Phe Ser Cys Ser Val Met His Glu Ala
            420             425             430

Leu His Asn His Tyr Thr Gln Lys Ser Leu Ser Leu Ser Pro Gly Lys
            435             440             445

<210> SEQ ID NO 63
<211> LENGTH: 220
<212> TYPE: PRT
<213> ORGANISM: Artificial Sequence
<220> FEATURE:
<223> OTHER INFORMATION: hGBA-9 Light Chain Sequence

<400> SEQUENCE: 63

-continued

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Asn Ser
                20                  25                  30

Gly Asn Gln Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Asp Tyr Ser Tyr Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
    210                 215                 220

<210> SEQ ID NO 64
<211> LENGTH: 330
<212> TYPE: PRT
<213> ORGANISM: Artificial Sequence
<220> FEATURE:
<223> OTHER INFORMATION: Constant heavy chain - CH1 + Fc domain

<400> SEQUENCE: 64

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

-continued

```
Val Val Val Asp Val Ser His Glu Asp Pro Glu Val Lys Phe Asn Trp
145             150                 155                 160

Tyr Val Asp Gly Val Glu Val His Asn Ala Lys Thr Lys Pro Arg Glu
            165             170                 175

Glu Gln Tyr Asn Ser Thr Tyr Arg Val Val Ser Val Leu Thr Val Leu
            180             185                 190

His Gln Asp Trp Leu Asn Gly Lys Glu Tyr Lys Cys Lys Val Ser Asn
            195             200                 205

Lys Ala Leu Pro Ala Pro Ile Glu Lys Thr Ile Ser Lys Ala Lys Gly
    210             215                 220

Gln Pro Arg Glu Pro Gln Val Tyr Thr Leu Pro Pro Ser Arg Asp Glu
225             230                 235                 240

Leu Thr Lys Asn Gln Val Ser Leu Thr Cys Leu Val Lys Gly Phe Tyr
            245             250                 255

Pro Ser Asp Ile Ala Val Glu Trp Glu Ser Asn Gly Gln Pro Glu Asn
            260             265                 270

Asn Tyr Lys Thr Thr Pro Pro Val Leu Asp Ser Asp Gly Ser Phe Phe
            275             280                 285

Leu Tyr Ser Lys Leu Thr Val Asp Lys Ser Arg Trp Gln Gln Gly Asn
    290             295                 300

Val Phe Ser Cys Ser Val Met His Glu Ala Leu His Asn His Tyr Thr
305             310                 315                 320

Gln Lys Ser Leu Ser Leu Ser Pro Gly Lys
            325                 330
```

<210> SEQ ID NO 65
<211> LENGTH: 107
<212> TYPE: PRT
<213> ORGANISM: Artificial Sequence
<220> FEATURE:
<223> OTHER INFORMATION: Constant light chain region

<400> SEQUENCE: 65

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
            100                 105
```

<210> SEQ ID NO 66
<211> LENGTH: 330
<212> TYPE: PRT
<213> ORGANISM: Artificial Sequence
<220> FEATURE:
<223> OTHER INFORMATION: Constant heavy chain region CH1 and Fc region
       with reduced Fc gamma R binding having the L234A/L235A mutations

<400> SEQUENCE: 66

-continued

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
        35              40                  45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100             105             110

Pro Ala Pro Glu Ala Ala Gly Gly Pro Ser Val Phe Leu Phe Pro Pro
        115             120             125

Lys Pro Lys Asp Thr Leu Met Ile Ser Arg Thr Pro Glu Val Thr Cys
    130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
            165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
        195             200             205

Lys Ala Leu Pro Ala Pro Ile Glu Lys Thr Ile Ser Lys Ala Lys Gly
    210             215             220

Gln Pro Arg Glu Pro Gln Val Tyr Thr Leu Pro Pro Ser Arg Asp Glu
225             230             235             240

Leu Thr Lys Asn Gln Val Ser Leu Thr Cys Leu Val Lys Gly Phe Tyr
            245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
        275             280             285

Leu Tyr Ser Lys Leu Thr Val Asp Lys Ser Arg Trp Gln Gln Gly Asn
    290             295             300

Val Phe Ser Cys Ser Val Met His Glu Ala Leu His Asn His Tyr Thr
305             310             315             320

Gln Lys Ser Leu Ser Leu Ser Pro Gly Lys
            325             330
```

```
<210> SEQ ID NO 67
<211> LENGTH: 330
<212> TYPE: PRT
<213> ORGANISM: Artificial Sequence
<220> FEATURE:
<223> OTHER INFORMATION: Constant heavy chain region CH1 and Fc region
      having the L234A/L235A/P329G mutations in the constant heavy chain
      region CH1 and Fc region with even further reduced Fc gamma R
      binding

<400> SEQUENCE: 67
```

```
Ala Ser Thr Lys Gly Pro Ser Val Phe Pro Leu Ala Pro Ser Ser Lys
1               5                   10                  15
```

-continued

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Gly Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 68
<211> LENGTH: 10
<212> TYPE: PRT
<213> ORGANISM: Artificial Sequence
<220> FEATURE:
<223> OTHER INFORMATION: N-terminal extracellular domain of CLDN18.2,
      independent of glycosylation

<400> SEQUENCE: 68

Asp Gln Trp Ser Thr Gln Asp Leu Tyr Asn
1               5                   10

<210> SEQ ID NO 69
<211> LENGTH: 11
<212> TYPE: PRT
<213> ORGANISM: Artificial Sequence
```

```
<220> FEATURE:
<223> OTHER INFORMATION: N-terminal extracellular domain of CLDN18.2,
      mainly unglycosylated

<400> SEQUENCE: 69

Asn Asn Pro Val Thr Ala Val Phe Asn Tyr Gln
1               5                   10

<210> SEQ ID NO 70
<211> LENGTH: 14
<212> TYPE: PRT
<213> ORGANISM: Artificial Sequence
<220> FEATURE:
<223> OTHER INFORMATION: N-terminal extracellular domain of CLDN18.2,
      unglycosylated

<400> SEQUENCE: 70

Ser Thr Gln Asp Leu Tyr Asn Asn Pro Val Thr Ala Val Phe
1               5                   10

<210> SEQ ID NO 71
<211> LENGTH: 13
<212> TYPE: PRT
<213> ORGANISM: Artificial Sequence
<220> FEATURE:
<223> OTHER INFORMATION: pan-CLDN18 peptide

<400> SEQUENCE: 71

Thr Asn Phe Trp Met Ser Thr Ala Asn Met Tyr Thr Gly
1               5                   10

<210> SEQ ID NO 72
<211> LENGTH: 16
<212> TYPE: PRT
<213> ORGANISM: Artificial Sequence
<220> FEATURE:
<223> OTHER INFORMATION: peptide sequence disclosed by WO2005/113587
      against specific epitopes on CLDN18.2

<400> SEQUENCE: 72

Ala Leu Met Ile Val Gly Ile Val Leu Gly Ala Ile Gly Leu Leu Val
1               5                   10                  15

<210> SEQ ID NO 73
<211> LENGTH: 24
<212> TYPE: PRT
<213> ORGANISM: Artificial Sequence
<220> FEATURE:
<223> OTHER INFORMATION: peptide sequence disclosed by WO2005/113587
      against specific epitopes on CLDN18.2

<400> SEQUENCE: 73

Arg Ile Gly Ser Met Glu Asp Ser Ala Lys Ala Asn Met Thr Leu Thr
1               5                   10                  15

Ser Gly Ile Met Phe Ile Val Ser
            20

<210> SEQ ID NO 74
<211> LENGTH: 129
<212> TYPE: PRT
<213> ORGANISM: Artificial Sequence
<220> FEATURE:
<223> OTHER INFORMATION: Peptide including the first extracellular
      domain of CLDN18.2 with N- and C-terminal extensions

<400> SEQUENCE: 74

Met Glu Thr Asp Thr Leu Leu Leu Trp Val Leu Leu Leu Trp Val Pro
```

-continued

```
1               5                   10                  15

Gly Ser Thr Gly Asp Ala Ala Gln Pro Ala Arg Arg Ala Arg Arg Thr
            20                  25                  30

Lys Leu Gly Thr Glu Leu Gly Ser Thr Pro Val Trp Trp Asn Ser Ala
        35                  40                  45

Asp Gly Arg Met Asp Gln Trp Ser Thr Gln Asp Leu Tyr Asn Asn Pro
    50                  55                  60

Val Thr Ala Val Phe Asn Tyr Gln Gly Leu Trp Arg Ser Cys Val Arg
65                  70                  75                  80

Glu Ser Ser Gly Phe Thr Glu Cys Arg Gly Tyr Phe Thr Leu Leu Gly
                85                  90                  95

Leu Pro Ala Met Leu Gln Ala Val Arg Ala Ala Ile Gln His Ser Gly
            100                 105                 110

Gly Arg Ser Arg Arg Ala Arg Thr Lys Thr His Leu Arg Arg Gly Ser
        115                 120                 125

Glu

<210> SEQ ID NO 75
<211> LENGTH: 15
<212> TYPE: PRT
<213> ORGANISM: Artificial Sequence
<220> FEATURE:
<223> OTHER INFORMATION: Overlapping peptides of CLDN18.2 within the
      first extracellular domain

<400> SEQUENCE: 75

Met Asp Gln Trp Ser Thr Gln Asp Leu Tyr Asn Asn Pro Val Thr
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Overlapping peptides of CLDN18.2 within the
      first extracellular domain

<400> SEQUENCE: 76

Leu Tyr Asn Asn Pro Val Thr Ala Val Phe Asn Tyr Gln Gly Leu
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Overlapping peptides of CLDN18.2 within the
      first extracellular domain

<400> SEQUENCE: 77

Val Phe Asn Tyr Gln Gly Leu Trp Arg Ser Cys Val Arg Glu Ser
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Overlapping peptides of CLDN18.2 within the
      first extracellular domain

<400> SEQUENCE: 78

Gln Gly Leu Trp Arg Ser Cys Val Arg Glu Ser Ser Gly Phe Thr
```

```
1               5               10              15

<210> SEQ ID NO 79
<211> LENGTH: 15
<212> TYPE: PRT
<213> ORGANISM: Artificial Sequence
<220> FEATURE:
<223> OTHER INFORMATION: Overlapping peptides of CLDN18.2 within the
      first extracellular domain

<400> SEQUENCE: 79

Arg Ser Cys Val Arg Glu Ser Ser Gly Phe Thr Glu Cys Arg Gly
1               5               10              15

<210> SEQ ID NO 80
<211> LENGTH: 15
<212> TYPE: PRT
<213> ORGANISM: Artificial Sequence
<220> FEATURE:
<223> OTHER INFORMATION: Epitope of antibody of WO2013/167259 binding
      to C-terminal epitopes of CLDN18.2

<400> SEQUENCE: 80

Thr Glu Asp Glu Val Gln Ser Tyr Pro Ser Lys His Asp Tyr Val
1               5               10              15

<210> SEQ ID NO 81
<211> LENGTH: 12
<212> TYPE: PRT
<213> ORGANISM: Artificial Sequence
<220> FEATURE:
<223> OTHER INFORMATION: Epitope of antibody of WO2013/167259 binding to
      C-terminal epitopes of CLDN18.2

<400> SEQUENCE: 81

Glu Val Gln Ser Tyr Pro Ser Lys His Asp Tyr Val
1               5               10

<210> SEQ ID NO 82
<211> LENGTH: 10
<212> TYPE: PRT
<213> ORGANISM: Artificial Sequence
<220> FEATURE:
<223> OTHER INFORMATION: Consensus including IMAB362 HC CDR1
<220> FEATURE:
<221> NAME/KEY: MISC_FEATURE
<222> LOCATION: (3)..(3)
<223> OTHER INFORMATION: T or S
<220> FEATURE:
<221> NAME/KEY: MISC_FEATURE
<222> LOCATION: (10)..(10)
<223> OTHER INFORMATION: G or N

<400> SEQUENCE: 82

Gly Tyr Xaa Phe Thr Ser Tyr Trp Ile Xaa
1               5               10

<210> SEQ ID NO 83
<211> LENGTH: 13
<212> TYPE: PRT
<213> ORGANISM: Artificial Sequence
<220> FEATURE:
<223> OTHER INFORMATION: Consensus including IMAB362 HC CDR2
<220> FEATURE:
<221> NAME/KEY: MISC_FEATURE
<222> LOCATION: (2)..(2)
<223> OTHER INFORMATION: N or I
<220> FEATURE:
<221> NAME/KEY: MISC_FEATURE
<222> LOCATION: (6)..(6)
```

-continued

```
<223> OTHER INFORMATION: S or G
<220> FEATURE:
<221> NAME/KEY: MISC_FEATURE
<222> LOCATION: (7)..(7)
<223> OTHER INFORMATION: A, E or D
<220> FEATURE:
<221> NAME/KEY: MISC_FEATURE
<222> LOCATION: (8)..(8)
<223> OTHER INFORMATION: A or S
<220> FEATURE:
<221> NAME/KEY: MISC_FEATURE
<222> LOCATION: (9)..(9)
<223> OTHER INFORMATION: Y or D
<220> FEATURE:
<221> NAME/KEY: MISC_FEATURE
<222> LOCATION: (11)..(11)
<223> OTHER INFORMATION: N or R
<220> FEATURE:
<221> NAME/KEY: MISC_FEATURE
<222> LOCATION: (13)..(13)
<223> OTHER INFORMATION: A, N or S

<400> SEQUENCE: 83

Gly Xaa Ile Tyr Pro Xaa Xaa Xaa Xaa Thr Xaa Tyr Xaa
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Consensus including IMAB362 HC CDR3
<220> FEATURE:
<221> NAME/KEY: MISC_FEATURE
<222> LOCATION: (1)..(1)
<223> OTHER INFORMATION: A or T
<220> FEATURE:
<221> NAME/KEY: MISC_FEATURE
<222> LOCATION: (3)..(3)
<223> OTHER INFORMATION: L, M, I, S or Q
<220> FEATURE:
<221> NAME/KEY: MISC_FEATURE
<222> LOCATION: (11)..(11)
<223> OTHER INFORMATION: A or Y

<400> SEQUENCE: 84

Xaa Arg Xaa Trp Arg Gly Asn Ser Phe Asp Xaa
1               5                   10

<210> SEQ ID NO 85
<211> LENGTH: 30
<212> TYPE: DNA
<213> ORGANISM: Artificial Sequence
<220> FEATURE:
<223> OTHER INFORMATION: hGBA-1, hGBA-3 HCDR1 Sequence

<400> SEQUENCE: 85
ggctatagct ttacatcata ttggattgga                                      30

<210> SEQ ID NO 86
<211> LENGTH: 39
<212> TYPE: DNA
<213> ORGANISM: Artificial Sequence
<220> FEATURE:
<223> OTHER INFORMATION: hGBA-1 HCDR2 Sequence

<400> SEQUENCE: 86
gggaacattt accctggggc atcggatacg cgatacgca                            39

<210> SEQ ID NO 87
<211> LENGTH: 33
```

-continued

```
<212> TYPE: DNA
<213> ORGANISM: Artificial Sequence
<220> FEATURE:
<223> OTHER INFORMATION: hGBA-1 HCDR3 Sequence

<400> SEQUENCE: 87
gcgagacttt ggcgggggaa tagcttcgac tac                                   33

<210> SEQ ID NO 88
<211> LENGTH: 51
<212> TYPE: DNA
<213> ORGANISM: Artificial Sequence
<220> FEATURE:
<223> OTHER INFORMATION: hGBA-1 LCDR1 Sequence

<400> SEQUENCE: 88
aaaagctccc aaagcctatt gaactcggga aaccaaaaga attacttggc a              51

<210> SEQ ID NO 89
<211> LENGTH: 21
<212> TYPE: DNA
<213> ORGANISM: Artificial Sequence
<220> FEATURE:
<223> OTHER INFORMATION: hGBA-1 LCDR2 Sequence

<400> SEQUENCE: 89
tgggcaagca cccgagagag c                                               21

<210> SEQ ID NO 90
<211> LENGTH: 27
<212> TYPE: DNA
<213> ORGANISM: Artificial Sequence
<220> FEATURE:
<223> OTHER INFORMATION: hGBA-1 LCDR3 Sequence

<400> SEQUENCE: 90
caaaacgact attcataccc attcaca                                         27

<210> SEQ ID NO 91
<211> LENGTH: 30
<212> TYPE: DNA
<213> ORGANISM: Artificial Sequence
<220> FEATURE:
<223> OTHER INFORMATION: hGBA-2 HCDR1 Sequence

<400> SEQUENCE: 91
ggatattcat ttacaagcta ctggatcgga                                      30

<210> SEQ ID NO 92
<211> LENGTH: 39
<212> TYPE: DNA
<213> ORGANISM: Artificial Sequence
<220> FEATURE:
<223> OTHER INFORMATION: hGBA-2 HCDR2 Sequence

<400> SEQUENCE: 92
ggaaatatat accccggaga cgcggacacg agatacgca                            39

<210> SEQ ID NO 93
<211> LENGTH: 33
<212> TYPE: DNA
<213> ORGANISM: Artificial Sequence
<220> FEATURE:
<223> OTHER INFORMATION: hGBA-2 HCDR3 Sequence

<400> SEQUENCE: 93
```

-continued gcgcggatgt ggcgcggcaa tagctttgac tac                                  33

<210> SEQ ID NO 94
<211> LENGTH: 39
<212> TYPE: DNA
<213> ORGANISM: Artificial Sequence
<220> FEATURE:
<223> OTHER INFORMATION: hGBA-3 HCDR2 Sequence

<400> SEQUENCE: 94
gggatcatct atccgggggc atccgatacc aactatgcg                            39

<210> SEQ ID NO 95
<211> LENGTH: 33
<212> TYPE: DNA
<213> ORGANISM: Artificial Sequence
<220> FEATURE:
<223> OTHER INFORMATION: hGBA-3 HCDR3 Sequence

<400> SEQUENCE: 95
gctaggattt ggcgaggaaa tagctttgat tat                                  33

<210> SEQ ID NO 96
<211> LENGTH: 51
<212> TYPE: DNA
<213> ORGANISM: Artificial Sequence
<220> FEATURE:
<223> OTHER INFORMATION: hGBA-3 LCDR1 Sequence

<400> SEQUENCE: 96
aagagctcgc aaagtttgct gaactccggg aaccaaaaga attacctggc a              51

<210> SEQ ID NO 97
<211> LENGTH: 21
<212> TYPE: DNA
<213> ORGANISM: Artificial Sequence
<220> FEATURE:
<223> OTHER INFORMATION: hGBA-3 LCDR2 Sequence

<400> SEQUENCE: 97
tgggcatcaa cgcgggaaag c                                               21

<210> SEQ ID NO 98
<211> LENGTH: 27
<212> TYPE: DNA
<213> ORGANISM: Artificial Sequence
<220> FEATURE:
<223> OTHER INFORMATION: hGBA-3 LCDR3 Sequence

<400> SEQUENCE: 98
caaaacgact actcctatcc gctgacc                                         27

<210> SEQ ID NO 99
<211> LENGTH: 30
<212> TYPE: DNA
<213> ORGANISM: Artificial Sequence
<220> FEATURE:
<223> OTHER INFORMATION: hGBA-4 HCDR1 Sequence

<400> SEQUENCE: 99
ggatactcat ttacatcata ctggatagga                                      30

<210> SEQ ID NO 100
<211> LENGTH: 39
<212> TYPE: DNA
<213> ORGANISM: Artificial Sequence -continued

```
<220> FEATURE:
<223> OTHER INFORMATION: hGBA-4 HCDR2 Sequence

<400> SEQUENCE: 100
gggattatat accccggcga cgcttacact cgatattcg                    39

<210> SEQ ID NO 101
<211> LENGTH: 33
<212> TYPE: DNA
<213> ORGANISM: Artificial Sequence
<220> FEATURE:
<223> OTHER INFORMATION: hGBA-4 HCDR3 Sequence

<400> SEQUENCE: 101
acgaggctat ggaggggggaa tagctttgat gcc                         33

<210> SEQ ID NO 102
<211> LENGTH: 51
<212> TYPE: DNA
<213> ORGANISM: Artificial Sequence
<220> FEATURE:
<223> OTHER INFORMATION: hGBA-4 LCDR1 Sequence

<400> SEQUENCE: 102
aagagctccc aaagcctatt gaactcggga aatcaaaaga attatctgac a       51

<210> SEQ ID NO 103
<211> LENGTH: 21
<212> TYPE: DNA
<213> ORGANISM: Artificial Sequence
<220> FEATURE:
<223> OTHER INFORMATION: hGBA-4 LCDR2 Sequence

<400> SEQUENCE: 103
tgggcctcga caagggagag c                                       21

<210> SEQ ID NO 104
<211> LENGTH: 27
<212> TYPE: DNA
<213> ORGANISM: Artificial Sequence
<220> FEATURE:
<223> OTHER INFORMATION: hGBA-4 LCDR3 Sequence

<400> SEQUENCE: 104
caaaatgact actcataccc gctgaca                                 27

<210> SEQ ID NO 105
<211> LENGTH: 30
<212> TYPE: DNA
<213> ORGANISM: Artificial Sequence
<220> FEATURE:
<223> OTHER INFORMATION: hGBA-5 HCDR1 Sequence

<400> SEQUENCE: 105
ggatatagct ttacgagcta ctggatcgga                              30

<210> SEQ ID NO 106
<211> LENGTH: 39
<212> TYPE: DNA
<213> ORGANISM: Artificial Sequence
<220> FEATURE:
<223> OTHER INFORMATION: hGBA-5 HCDR2 Sequence

<400> SEQUENCE: 106
gggataatat accccggagc ggcatacacg agatatgcg                    39
```

-continued

```
<210> SEQ ID NO 107
<211> LENGTH: 33
<212> TYPE: DNA
<213> ORGANISM: Artificial Sequence
<220> FEATURE:
<223> OTHER INFORMATION: hGBA-5 HCDR3 Sequence

<400> SEQUENCE: 107
gcgagactat ggcgcgggaa ctcatttgat tac                                33

<210> SEQ ID NO 108
<211> LENGTH: 51
<212> TYPE: DNA
<213> ORGANISM: Artificial Sequence
<220> FEATURE:
<223> OTHER INFORMATION: hGBA-5 LCDR1 Sequence

<400> SEQUENCE: 108
aaatcatcgc aatcattgct aaattcgggg aaccaaaaga attatttggc a            51

<210> SEQ ID NO 109
<211> LENGTH: 21
<212> TYPE: DNA
<213> ORGANISM: Artificial Sequence
<220> FEATURE:
<223> OTHER INFORMATION: hGBA-5 LCDR2 Sequence

<400> SEQUENCE: 109
tgggcatcca cgagagaatc g                                             21

<210> SEQ ID NO 110
<211> LENGTH: 27
<212> TYPE: DNA
<213> ORGANISM: Artificial Sequence
<220> FEATURE:
<223> OTHER INFORMATION: hGBA-5 LCDR3 Sequence

<400> SEQUENCE: 110
caacaagatt attcataccc atttaca                                       27

<210> SEQ ID NO 111
<211> LENGTH: 30
<212> TYPE: DNA
<213> ORGANISM: Artificial Sequence
<220> FEATURE:
<223> OTHER INFORMATION: hGBA-6 HCDR1 Sequence

<400> SEQUENCE: 111
ggatatacat ttacatctta ctggatcgga                                    30

<210> SEQ ID NO 112
<211> LENGTH: 36
<212> TYPE: DNA
<213> ORGANISM: Artificial Sequence
<220> FEATURE:
<223> OTHER INFORMATION: hGBA-6 HCDR2 Sequence

<400> SEQUENCE: 112
gggaacattt atcctggcgc gagctatacg cgctat                             36

<210> SEQ ID NO 113
<211> LENGTH: 33
<212> TYPE: DNA
<213> ORGANISM: Artificial Sequence
<220> FEATURE:
<223> OTHER INFORMATION: hGBA-6 HCDR3 Sequence
```

<400> SEQUENCE: 113
acccggcaat ggaggggcaa tagctttgac tac                                    33

<210> SEQ ID NO 114
<211> LENGTH: 30
<212> TYPE: DNA
<213> ORGANISM: Artificial Sequence
<220> FEATURE:
<223> OTHER INFORMATION: hGBA-7 HCDR1 Sequence

<400> SEQUENCE: 114
ggatattcct ttacatcata ctggatcggc                                        30

<210> SEQ ID NO 115
<211> LENGTH: 39
<212> TYPE: DNA
<213> ORGANISM: Artificial Sequence
<220> FEATURE:
<223> OTHER INFORMATION: hGBA-7 HCDR2 Sequence

<400> SEQUENCE: 115
gggaacatat atcccggaga agcctatacg agatactcg                              39

<210> SEQ ID NO 116
<211> LENGTH: 33
<212> TYPE: DNA
<213> ORGANISM: Artificial Sequence
<220> FEATURE:
<223> OTHER INFORMATION: hGBA-7 HCDR3 Sequence

<400> SEQUENCE: 116
acgcgactat ggaggggaaa tagctttgac tat                                    33

<210> SEQ ID NO 117
<211> LENGTH: 51
<212> TYPE: DNA
<213> ORGANISM: Artificial Sequence
<220> FEATURE:
<223> OTHER INFORMATION: hGBA-7 LCDR1 Sequence

<400> SEQUENCE: 117
aagagctccc aatcagtcct gaactctggg aatcaaaaga attacctgac a                51

<210> SEQ ID NO 118
<211> LENGTH: 21
<212> TYPE: DNA
<213> ORGANISM: Artificial Sequence
<220> FEATURE:
<223> OTHER INFORMATION: hGBA-7, h-GBA 9 LCDR2 Sequence

<400> SEQUENCE: 118
tgggcgagca cgagggagag c                                                 21

<210> SEQ ID NO 119
<211> LENGTH: 27
<212> TYPE: DNA
<213> ORGANISM: Artificial Sequence
<220> FEATURE:
<223> OTHER INFORMATION: hGBA-7 LCDR3 Sequence

<400> SEQUENCE: 119
caaaatgatt attcataccc cttcaca                                           27

<210> SEQ ID NO 120

```
<211> LENGTH: 30
<212> TYPE: DNA
<213> ORGANISM: Artificial Sequence
<220> FEATURE:
<223> OTHER INFORMATION: hGBA-8 HCDR1 Sequence

<400> SEQUENCE: 120
ggatactcct ttacatcata ttggatcgga                                     30

<210> SEQ ID NO 121
<211> LENGTH: 39
<212> TYPE: DNA
<213> ORGANISM: Artificial Sequence
<220> FEATURE:
<223> OTHER INFORMATION: hGBA-8 HCDR2 Sequence

<400> SEQUENCE: 121
ggaaacatat atccgagcga atcatatacg aactacgcg                           39

<210> SEQ ID NO 122
<211> LENGTH: 33
<212> TYPE: DNA
<213> ORGANISM: Artificial Sequence
<220> FEATURE:
<223> OTHER INFORMATION: hGBA-8 HCDR3 Sequence

<400> SEQUENCE: 122
acgaggctat ggagggggaa tagcttcgac tat                                 33

<210> SEQ ID NO 123
<211> LENGTH: 30
<212> TYPE: DNA
<213> ORGANISM: Artificial Sequence
<220> FEATURE:
<223> OTHER INFORMATION: hGBA-9 HCDR1 Sequence

<400> SEQUENCE: 123
ggatatacat tcacgagcta ctggatagga                                     30

<210> SEQ ID NO 124
<211> LENGTH: 39
<212> TYPE: DNA
<213> ORGANISM: Artificial Sequence
<220> FEATURE:
<223> OTHER INFORMATION: hGBA-9 HCDR2 Sequence

<400> SEQUENCE: 124
ggaatcatat atccttccgc ggcatatacg cgatatgcg                           39

<210> SEQ ID NO 125
<211> LENGTH: 33
<212> TYPE: DNA
<213> ORGANISM: Artificial Sequence
<220> FEATURE:
<223> OTHER INFORMATION: hGBA-9 HCDR3 Sequence

<400> SEQUENCE: 125
acgcggatgt ggaggggaaa tagctttgat tac                                 33

<210> SEQ ID NO 126
<211> LENGTH: 51
<212> TYPE: DNA
<213> ORGANISM: Artificial Sequence
<220> FEATURE:
<223> OTHER INFORMATION: hGBA-9 LCDR1 Sequence

<400> SEQUENCE: 126
```

-continued

```
aagagctcgc aatcggtcct gaatagcggg aaccaaaaga attatctggc c          51

<210> SEQ ID NO 127
<211> LENGTH: 27
<212> TYPE: DNA
<213> ORGANISM: Artificial Sequence
<220> FEATURE:
<223> OTHER INFORMATION: hGBA-9 LCDR3 Sequence

<400> SEQUENCE: 127
caacaagact actcataccc atttaca                                     27

<210> SEQ ID NO 128
<211> LENGTH: 354
<212> TYPE: DNA
<213> ORGANISM: Artificial Sequence
<220> FEATURE:
<223> OTHER INFORMATION: hGBA-1 VH Sequence

<400> SEQUENCE: 128
gaagtccaac tggtccaatc cggcgcggag gttaagaagc ccggagaatc gctgaagatc    60
tcatgcaaag ggagcggcta tagctttaca tcatattgga ttggatgggt caggcaaatg   120
ccggggaagg ggctggaatg gatggggaac atttaccctg gggcatcgga tacgcgatac   180
gcacctagct ttcaagggca agtcacaatt tcggcggaca agagcatctc aacggcatac   240
ctgcaatggt cgagcttgaa ggcatctgat actgcaatgt actactgcgc gagactttgg   300 cggggggaata gcttcgacta ctgggggcag ggtaccctgg ttacggtctc gagc         354

<210> SEQ ID NO 129
<211> LENGTH: 339
<212> TYPE: DNA
<213> ORGANISM: Artificial Sequence
<220> FEATURE:
<223> OTHER INFORMATION: hGBA-1, h-GBA 2, h-GBA 6, h-GBA 8 VL Sequence

<400> SEQUENCE: 129
gacattgtga tgacgcaaag ccccgattcg ctggctgtat cgctagggga gcgcgctacg    60
atcaattgca aaagctccca aagcctattg aactcgggaa accaaaagaa ttacttggca   120
tggtatcaac aaaaaccggg gcaaccgccg aagctgctga tctattgggc aagcacccga   180
gagagcggtg tcccggaccg atttagcggg agcggatcgg gcaccgactt cacgctgaca   240
ataagctcat tgcaagccga ggatgtggcg gtctattatt gccaaaacga ctattcatac   300
ccattcacat tcgggcaagg taccaaggtc gagatcaag                         339

<210> SEQ ID NO 130
<211> LENGTH: 354
<212> TYPE: DNA
<213> ORGANISM: Artificial Sequence
<220> FEATURE:
<223> OTHER INFORMATION: hGBA-2 VH Sequence

<400> SEQUENCE: 130
gaagtccaac tggtccaatc tggagcggaa gtcaagaagc ctggggagag cctgaaaatt    60
tcatgcaagg ggagcggata ttcatttaca agctactgga tcggatgggt ccggcaaatg   120
ccggggaagg gcttggaatg gatgggaaat atataccccg agacgcgga cacgagatac    180 gcaccgagct ttcaagggca ggtcaccatt agcgctgata atcgatttc aaccgcatat    240 ctgcaatggt catcgctgaa ggcctccgac accgcgatgt actattgcgc gcggatgtgg   300
```
cgcggcaata gctttgacta ctgggggcag ggtaccctcg tcacggtctc gagc          354

<210> SEQ ID NO 131
<211> LENGTH: 354
<212> TYPE: DNA
<213> ORGANISM: Artificial Sequence
<220> FEATURE:
<223> OTHER INFORMATION: hGBA-3 VH Sequence

<400> SEQUENCE: 131
gaggtccaac tggtccaaag cggcgcggag gtcaagaagc cgggagaatc cctgaagatt          60
agctgcaaag gctccggcta tagctttaca tcatattgga tcggatgggt cagacaaatg          120
ccgggaaagg gacttgaatg gatggggatc atctatccgg gggcatccga taccaactat          180
gcgccgagct tccaagggca ggtcacgata tccgcggata aatcgattag caccgcatat          240
ctgcaatgga gctcgctgaa ggcatccgac accgcgatgt actactgcgc taggatttgg          300
cgaggaaata gctttgatta ttggggggcag ggtacccttg tcacggtctc gagc          354

<210> SEQ ID NO 132
<211> LENGTH: 339
<212> TYPE: DNA
<213> ORGANISM: Artificial Sequence
<220> FEATURE:
<223> OTHER INFORMATION: hGBA-3 VL Sequence

<400> SEQUENCE: 132
gacattgtca tgacgcaaag ccccgactcg ctggccgtct cactgggggga gcgggcgaca          60 atcaactgca agagctcgca aagtttgctg aactccggga ccaaaagaa ttacctggca          120 tggtatcaac aaaagccggg gcaacccccg aagctgctga tatattgggc atcaacgcgg          180
gaaagcggag tcccggatag atttagcgga tctggatcgg ggaccgactt cacgctgacg          240
atatctagcc ttcaagccga ggatgtggct gtatattatt gccaaaacga ctactcctat          300
ccgctgacct tcgggcaagg taccaaggtc gagatcaag          339

<210> SEQ ID NO 133
<211> LENGTH: 354
<212> TYPE: DNA
<213> ORGANISM: Artificial Sequence
<220> FEATURE:
<223> OTHER INFORMATION: hGBA-4 VH Sequence

<400> SEQUENCE: 133
gaagtccaac tagtccaaag cggagccgaa gtcaagaaac cgggggagag ccttaagatc          60
tcatgcaagg ggagcggata ctcatttaca tcatactgga taggatgggt cagacaaatg          120
cccggcaagg ggctggaatg gatgggggatt atatacccccg gcgacgctta cactcgatat          180
tcgccatcat tccaagggca ggtcacgata tcggccgata aatcgatatc cacggcatac          240
ctgcaatgga gctcactgaa agcatctgat acggcaatgt attattgcac gaggctatgg          300 aggggggaata gctttgatgc ctgggggcag ggtaccctgg tcacggtctc gagc          354

<210> SEQ ID NO 134
<211> LENGTH: 339
<212> TYPE: DNA
<213> ORGANISM: Artificial Sequence
<220> FEATURE:
<223> OTHER INFORMATION: hGBA-4 VL Sequence

<400> SEQUENCE: 134
gacatagtta tgacacaatc gccggatagc ctcgcggtca gccttggaga gcgggcgacg          60

-continued

```
atcaactgca agagctccca aagcctattg aactcgggaa atcaaaagaa ttatctgaca      120
tggtatcaac aaaagccggg gcaaccaccg aaactgctga tctattgggc ctcgacaagg      180
gagagcggag tcccggaccg cttctctgga tcgggaagcg ggactgactt cacgctgacc      240
ataagctcgc tgcaagccga ggacgtcgcc gtctattatt gccaaaatga ctactcatac      300
ccgctgacat ttggccaagg taccaaggtc gagatcaag                             339
```

<210> SEQ ID NO 135
<211> LENGTH: 354
<212> TYPE: DNA
<213> ORGANISM: Artificial Sequence
<220> FEATURE:
<223> OTHER INFORMATION: hGBA-5 VH Sequence

<400> SEQUENCE: 135

```
gaggtgcaac tggtacaatc cggggcggaa gtgaagaagc cgggggaatc gctgaagata       60
agctgcaaag gctctggata tagctttacg agctactgga tcggatgggt caggcaaatg      120
ccggggaagg gactggaatg gatggggata atataccccg gagcggcata cacgagatat      180
gcgccgagct ccaagggca agtgacaata agcgcggaca aatcgattag cacggcatat      240
ctgcaatggt cctcgctgaa ggcgagcgat accgcaatgt actattgcgc gagactatgg      300
cgcgggaact catttgatta ctggggcag ggtaccctag tgacggtctc gagc            354
```

<210> SEQ ID NO 136
<211> LENGTH: 339
<212> TYPE: DNA
<213> ORGANISM: Artificial Sequence
<220> FEATURE:
<223> OTHER INFORMATION: hGBA-5 VL Sequence

<400> SEQUENCE: 136

```
gacattgtca tgacgcaaag cccggatagc ctggctgtat cgctggggga gagagcgacg       60
atcaactgca aatcatcgca atcattgcta aattcgggga accaaaagaa ttatttggca      120
tggtatcaac aaaagccggg gcaaccgccg aaactgctga tttactgggc atccacgaga      180
gaatcgggag tcccggaccg atttagcgga tctgggagcg ggaccgattt cacgctgacc      240
attagctcgc tgcaagcgga ggatgtggcg gtctattact gccaacaaga ttattcatac      300
ccatttacat ttgggcaagg taccaaggtc gagatcaag                             339
```

<210> SEQ ID NO 137
<211> LENGTH: 354
<212> TYPE: DNA
<213> ORGANISM: Artificial Sequence
<220> FEATURE:
<223> OTHER INFORMATION: hGBA-6 VH Sequence

<400> SEQUENCE: 137

```
gaagtacaat tggttcaatc gggggccgaa gtcaagaagc cggggaatc gctgaagata       60 tcctgcaagg ggagcggata tacatttaca tcttactgga tcggatgggt cagacaaatg      120
cccggaaagg ggcttgaatg gatggggaac atttatcctg gcgcgagcta tacgcgctat      180
agcccgagct ccaagggca ggtcacgatt agcgccgaca agagcatttc gacggcatac      240
ctgcaatgga gctcgctgaa agcatcggat acggcaatgt attactgcac ccggcaatgg      300
aggggcaata gctttgacta ctggggcag ggtaccctag tcacggtctc gagc            354
```

<210> SEQ ID NO 138

-continued

```
<211> LENGTH: 354
<212> TYPE: DNA
<213> ORGANISM: Artificial Sequence
<220> FEATURE:
<223> OTHER INFORMATION: hGBA-7 VH Sequence

<400> SEQUENCE: 138
gaagttcaat tggtccaatc tggagccgaa gtcaagaagc ccggagaatc gctgaagatt      60
agctgcaagg ggagcggata ttcctttaca tcatactgga tcggctgggt cagacaaatg     120
cccggaaagg gactggaatg gatggggaac atatatcccg gagaagccta tacgagatac     180
tcgccatcat ttcaaggaca ggtcaccata agcgcggaca agagcataag caccgcatac     240
ctgcaatgga gctcgctgaa ggcatcggac accgccatgt attactgcac gcgactatgg     300
aggggaaata gctttgacta ttgggggcag ggtaccttag tcacggtctc gagc           354

<210> SEQ ID NO 139
<211> LENGTH: 339
<212> TYPE: DNA
<213> ORGANISM: Artificial Sequence
<220> FEATURE:
<223> OTHER INFORMATION: hGBA-7 VL Sequence

<400> SEQUENCE: 139
gatatagtaa tgactcaatc acccgatagc ttggctgtga gcctgggaga aagagctaca      60
atcaactgca agagctccca atcagtcctg aactctggga atcaaaagaa ttacctgaca     120
tggtatcaac aaaagcccgg acaaccgccg aagctgctga tctactgggc gagcacgagg     180
gagagcggag tcccggatcg attttctggc tccgggagcg aaccgactt cacactgact      240 attagctcgc tgcaagcgga ggacgtcgcc gtctactatt gccaaaatga ttattcatac     300
cccttcacat ttgggcaagg taccaaggtc gagatcaag                            339

<210> SEQ ID NO 140
<211> LENGTH: 354
<212> TYPE: DNA
<213> ORGANISM: Artificial Sequence
<220> FEATURE:
<223> OTHER INFORMATION: hGBA-8 VH Sequence

<400> SEQUENCE: 140
gaggtgcaac tagtgcaatc gggggccgaa gtgaagaaac ctgggaatc gctgaagata       60 tcatgcaagg ggagcggata ctcctttaca tcatattgga tcggatgggt caggcaaatg     120
ccggggaagg ggctggaatg gatgggaaac atatatccga gcgaatcata tacgaactac     180
gcgccgagct ttcaaggaca agtcacgata tccgcggata aatcgatatc gaccgcatac     240
ctgcaatgga gctcgctgaa ggcttccgac actgcgatgt attactgcac gaggctatgg     300 aggggggaata gcttcgacta ttgggggcag ggtaccctgg tgacggtctc gagc          354

<210> SEQ ID NO 141
<211> LENGTH: 354
<212> TYPE: DNA
<213> ORGANISM: Artificial Sequence
<220> FEATURE:
<223> OTHER INFORMATION: hGBA-9 VH Sequence

<400> SEQUENCE: 141
gaagtccaat tagtccaatc gggggccgag gtcaagaagc cggggggaatc gctcaagata      60 agctgcaagg gatcgggata tacattcacg agctactgga taggatgggt caggcaaatg     120
ccggggaagg ggctggaatg gatgggaatc atatatcctt ccgcggcata tacgcgatat     180
```

-continued

```
gcgccatcat ttcaaggaca ggtcacgata agcgccgaca agagcattag caccgcatac      240
ctgcaatggt cgagccttaa ggcatcggac accgcgatgt actactgcac gcggatgtgg      300
aggggaaata gctttgatta ctgggggcag ggtaccctag tcacggtctc gagc            354
```

```
<210> SEQ ID NO 142
<211> LENGTH: 339
<212> TYPE: DNA
<213> ORGANISM: Artificial Sequence
<220> FEATURE:
<223> OTHER INFORMATION: hGBA-9 VL Sequence

<400> SEQUENCE: 142
gacatcgtca tgacgcaaag cccggactcg ctggcggtct cgctggggga gcgggccaca       60
ataaattgca agagctcgca atcggtcctg aatagcggga accaaaagaa ttatctggcc      120
tggtatcaac aaaagccggg gcaaccaccg aagctgctaa tctattgggc gagcacgagg      180
gagagcggag tccccgatcg atttagcgga tcgggaagcg ggaccgattt cacgctgacg      240
atttcgagcc tacaagccga ggatgtggcg gtctattact gccaacaaga ctactcatac      300
ccatttacat ttggacaagg taccaaggtc gagatcaag                              339
```

```
<210> SEQ ID NO 143
<211> LENGTH: 7
<212> TYPE: PRT
<213> ORGANISM: Artificial Sequence
<220> FEATURE:
<223> OTHER INFORMATION: RLPXTGG tag
<220> FEATURE:
<221> NAME/KEY: MISC_FEATURE
<222> LOCATION: (4)..(4)
<223> OTHER INFORMATION: X is any of the 20 natural amino acids

<400> SEQUENCE: 143

Arg Leu Pro Xaa Thr Gly Gly
1               5
```

```
<210> SEQ ID NO 144
<211> LENGTH: 11
<212> TYPE: PRT
<213> ORGANISM: Artificial Sequence
<220> FEATURE:
<223> OTHER INFORMATION: GGGGSLPXTGG tag
<220> FEATURE:
<221> NAME/KEY: MISC_FEATURE
<222> LOCATION: (8)..(8)
<223> OTHER INFORMATION: X is any of the 20 natural amino acids

<400> SEQUENCE: 144

Gly Gly Gly Gly Ser Leu Pro Xaa Thr Gly Gly
1               5                   10
```